(12) United States Patent
Lehmann et al.

(10) Patent No.: US 9,388,206 B2
(45) Date of Patent: Jul. 12, 2016

(54) CHROMOPHORES WITH PERFLUOROALKYL SUBSTITUENTS

(75) Inventors: Urs Lehmann, Basel (CH); Daniel Heizler, Basel (CH)

(73) Assignee: BASF SE, Ludwigshafen (DE)

(*) Notice: Subject to any disclaimer, the term of this patent is extended or adjusted under 35 U.S.C. 154(b) by 269 days.

(21) Appl. No.: 14/115,878

(22) PCT Filed: Apr. 25, 2012

(86) PCT No.: PCT/EP2012/057522
§ 371 (c)(1),
(2), (4) Date: Nov. 6, 2013

(87) PCT Pub. No.: WO2012/152584
PCT Pub. Date: Nov. 15, 2012

(65) Prior Publication Data
US 2014/0103635 A1    Apr. 17, 2014

Related U.S. Application Data

(60) Provisional application No. 61/483,067, filed on May 6, 2011.

(30) Foreign Application Priority Data

May 6, 2011 (EP) .................... 11165036

(51) Int. Cl.
| C07F 15/00 | (2006.01) |
| C07F 15/04 | (2006.01) |
| A61K 8/49 | (2006.01) |
| A61K 8/69 | (2006.01) |
| A61Q 17/04 | (2006.01) |
| A61K 8/19 | (2006.01) |
| C09D 11/50 | (2014.01) |
| C07F 9/00 | (2006.01) |
| A61K 8/00 | (2006.01) |
| C09D 11/00 | (2014.01) |
| C09D 11/10 | (2014.01) |
| B42D 25/29 | (2014.01) |

(52) U.S. Cl.
CPC .......... *C07F 15/045* (2013.01); *A61K 8/00* (2013.01); *A61K 8/19* (2013.01); *A61K 8/49* (2013.01); *A61K 8/69* (2013.01); *A61Q 17/04* (2013.01); *B42D 25/29* (2014.10); *C07F 9/005* (2013.01); *C07F 15/00* (2013.01); *C07F 15/0066* (2013.01); *C07F 15/0093* (2013.01); *C07F 15/04* (2013.01); *C09D 11/00* (2013.01); *C09D 11/10* (2013.01); *C09D 11/50* (2013.01); *A61K 2800/522* (2013.01); *A61K 2800/524* (2013.01); *A61K 2800/58* (2013.01)

(58) Field of Classification Search
CPC . C07F 15/045; C07F 15/0066; C07F 15/0093
See application file for complete search history.

(56) References Cited

U.S. PATENT DOCUMENTS

| 2,862,974 | A | 12/1958 | Sieglitz et al. |
| 5,282,894 | A | 2/1994 | Albert et al. |
| 6,544,499 | B1 | 4/2003 | Glenn, Jr. et al. |
| 6,926,764 | B2 * | 8/2005 | Bleikolm ............ B41M 3/14 106/31.27 |
| 2008/0241492 | A1 | 10/2008 | Maeder et al. |
| 2010/0015411 | A1 | 1/2010 | Devonald |
| 2010/0021833 | A1 | 1/2010 | Lehmann et al. |
| 2012/0129090 | A1 | 5/2012 | Mamak et al. |
| 2012/0135459 | A1 | 5/2012 | Hell et al. |
| 2012/0229884 | A1 | 9/2012 | Hayoz et al. |
| 2013/0092874 | A1 | 4/2013 | Bacher et al. |
| 2013/0234427 | A1 | 9/2013 | Reichelt et al. |

FOREIGN PATENT DOCUMENTS

| EP | 2 643 416 A | 10/2013 |
| JP | 61-203446 A | 9/1986 |
| JP | 63-312364 A | 12/1988 |
| JP | 5-65423 A | 3/1993 |
| JP | 5-255602 A | 10/1993 |
| JP | 7-82496 A | 3/1995 |
| JP | 7-118550 A | 5/1995 |
| JP | 2001-347765 A | 12/2001 |
| JP | 2003-73589 A | 3/2003 |
| JP | 2003-262953 A | 9/2003 |
| JP | 2003262953 A * | 9/2003 |
| JP | 2004-045653 A | 2/2004 |
| JP | 2004-157455 A | 6/2004 |
| JP | 2005-099755 A | 4/2005 |
| JP | 2008-115225 A | 5/2008 |

(Continued)

OTHER PUBLICATIONS

International Search Report issued Jul. 19, 2012 in PCT/EP2012/057522.

Massimiliano Arca, et al., "Synthesis, X-ray crystal structure and spectroscopic characterization of the new dithiolene [Pd(Et2timdt02] and of its adduct with molecular diiodine [Pd(Et2timdt02]-I2-CHCl3 (Et2timdt=monoanion of 1,3-diethylimidazolidine-2,4,5-trithione)" J. Chem. Soc, Dalton Trans., 1998, pp. 3731-3736.

M. Carla Aragoni, et al., "NIR Dyes Based on [M(R,R'timdt)2] Metal-Dithiolenes: Additivity of M, R, and R' Contributions to Tune the NIR Absorption (M=Ni, Pd, Pt; R,R'timdt = Monoreduced Form of Disubstituted Imidazolidine-2,4,5-trithione)" Eur. J. Inorg. Chem, 2003, pp. 1939-1947.

*Primary Examiner* — Joseph Kosack
(74) *Attorney, Agent, or Firm* — Oblon, McClelland, Maier & Neustadt, L.L.P

(57) ABSTRACT

The present invention relates to specific metal complexes of dithiolenes with perfluoroalkyl substituted imidazolidine-2-chalcogenone-4,5-dithione ligands, a process for their preparation and their use as colourless IR absorbers, for optical filters application; especially for plasma display panels, or for laser welding of plastics. The compounds may be used in compositions for inks, paints and plastics, especially in a wide variety of printing systems and are particularly well-suited for security applications.

17 Claims, No Drawings

(56) References Cited

FOREIGN PATENT DOCUMENTS

| | | |
|---|---|---|
| JP | 2010-516823 A | 5/2010 |
| WO | WO 2006/015414 A1 | 2/2006 |
| WO | WO 2007/071550 A1 | 6/2007 |
| WO | WO 2007/091094 A1 | 8/2007 |
| WO | WO 2007/132214 A1 | 11/2007 |
| WO | WO 2008/047071 A1 | 4/2008 |
| WO | WO 2008/086931 A1 | 7/2008 |
| WO | WO 2010/046285 A2 | 4/2010 |
| WO | WO 2010/149190 A1 | 12/2010 |
| WO | WO 2012/069518 A1 | 5/2012 |

* cited by examiner

CHROMOPHORES WITH PERFLUOROALKYL SUBSTITUENTS

CROSS REFERENCE TO RELATED APPLICATIONS

The present application is a 35 U.S.C. §371 national stage patent application of International patent application PCT/EP2012/057522, filed on Apr. 25, 2012, published as WO/2012/152584 on Nov. 15, 2012, the text of which is incorporated by reference, and claims the benefit of the filing date of U.S. provisional application No. 61/483,067, filed on May 6, 2011, and EP application no. 11165036.2, filed on May 6, 2011, the text of both of which is also incorporated by reference.

The present invention relates to specific metal complexes of dithiolenes with perfluoroalkyl substituted imidazolidine-2-chalcogenone-4,5-dithione ligands, a process for their preparation and their use as colourless IR absorbers, for optical filters application; especially for plasma display panels, or for laser welding of plastics. The compounds may be used in compositions for inks, paints and plastics, especially in a wide variety of printing systems and are particularly well-suited for security applications.

DESCRIPTION OF THE RELATED ART

Colourless, or at least barely coloured, IR absorbers meet a significant technical need in a wide range of applications, such as security printing (bank notes, credit cards, identity cards, passports etc.), invisible and/or IR readable bar codes, the laser-welding of plastics, the curing of surface-coatings using IR radiators, the drying and curing of print, the fixing of toners on paper or plastics, optical filters for PDPs (plasma display panels), laser marking e.g. of paper or plastics, the heating of plastics preforms, heat shielding applications, etc.

A large number of organic and inorganic substances belonging to different compound classes and with a great variety of different structures are known for the application as IR absorbers. Notwithstanding that large numbers of known compound classes and structures, the provision of products with a complex profile of properties often presents difficulties. There is a continuing demand for IR absorber that are "colourlessness" (i.e. with the minimum possible inherent colour), and that simultaneously meet the technical stability requirements (chemical stability, heat stability and/or light stability).

A special field of application for colourless IR absorbers regards inks for printing processes which are used for printing currency and other security documents, also referred to as "security printing". Typical security printing processes are processes, wherein an ink composition is employed that is designed to selectively absorb radiation in parts of the "optical infrared" spectrum, whilst being transparent in other parts of it. IR absorbers for security printing are available, for example, from "American Dye Source", but virtually all of them have a noticeable absorption in the VIS range of the spectrum (from 400 to 700 nm).

WO2006/015414 describes IR-absorbing naphthalocyanine dyes for security printing.

US2008/0241492 describes an intaglio printing ink for a security printing process, wherein the ink comprises a polymeric organic binder and an infrared absorbing material that comprises transition element atoms or ions whose infrared absorption is a consequence of electronic transitions within the d-shell of the transition element. Suitable transition elements are Ti, V, Cr, Mn, Fe, Co, Ni, and Cu. In a suitable embodiment, the infrared absorbing material is a glass, in which there is a coordination of the transition element ions to phosphate and/or fluoride anions present in the glass. In a further suitable embodiment, the infrared absorbing material is an IR-absorbing transition element atom or ion bound to the polymer binder of the ink. In particular, the infrared absorbing material is an IR-absorbing complex of a transition element atom or ion and a binding site contained in the polymer, e.g. an organic thiourea-copper(II) complex dissolved in the polymeric binder.

U.S. Pat. No. 5,282,894 describes a liquid useful as printing ink that contains one or more dyes with their absorption maximum within the range from 700 to 1200 nm selected from phthalocyanines, naphthalocyanines, nickel-dithiolene complexes, aminium compounds of aromatic amines, methine dyes or azulenesquaric acid dyes, as well as solvent and binder.

WO2007/091094 describes an image article that comprises a substrate having a security image coated on at least a portion thereof, wherein the security image comprises a defined infrared-absorbing compound, for example Pigment Green 8, that does not create a strongly coloured security image. The disclosed infrared-absorbing compounds still have a noticeable absorption in the VIS range of the spectrum.

WO2007/132214 describes a composition comprising an ink and an infrared-absorbing material that comprises a metal, a metal salt, a metal oxide or metal nitride, wherein the metal is in particular selected from periods 4, 5 or the lanthanides. Also described is an article comprising a substrate having imaged thereon an infrared-absorbing material to form a security image, and a method of manufacture of such an article by image-wise application of a composition comprising such an infrared-absorbing material to a substrate.

M. Arca et al. describe in J. Chem. Soc., Dalton Trans. 1998, 3731-3736 metal dithiolenes belonging to the general class [M(R,R'timdt)₂] (M=Ni, Pd; (R,R' timdt)=monoanion of disubstituted imidazolidine-2,4,5-trithione; R and R'=ethyl or isopropyl). As those metal dithiolenes exhibit large π-electron delocalization they can also be characterized by the aromatic resonance structure on the right:

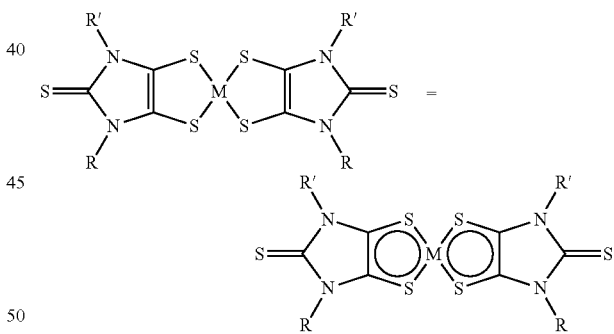

JP2003-262953A, JP2004-045653A and JP2005-99755A describe metal dithiolenes [M(R,R'timdt)₂], wherein R and R' are selected from unsubstituted and substituted alkyl, cycloalkyl and aryl groups.

M. C. Aragoni et al. describe in Eur. J. Inorg. Chem. 2003, 1939-1947 NIR dyes based on [M(R,R'timdt)₂] metal dithiolenes, wherein R and R' are inter alia selected from unsubstituted and substituted aryl groups.

WO2008/086931 teaches the use of dithiolene metal complexes [M(L)₂], wherein L is the monoanion of a disubstituted imidazolidine-2-chalcogenone-4,5-dithione and the chalcogene is O or S, as colourless IR absorbers. In all examples the nitrogen atoms bear only unsubstituted and substituted alkyl and alkenyl groups. Especially in respect of colourlessness, the compounds described in WO2008/086931 are superior to the IR absorbers known before, while simultaneously meeting other technical requirements, such as good fastness to light or good heat stability when incorporated into plastics material (e.g. for laser-welding). Nevertheless, for high-end applications the dithiolene metal complexes described in WO2008/086931 are still in need of improvement with regard to their fastness properties, e.g. fastness to chemicals and boiling water. Those properties are important in particular for applications in the field of security printing.

EP10192338.1 describes dithiolene metal complexes [M(L)$_2$], wherein L is selected from monoanions of a disubstituted imidazolidine-2-chalcogenone-4,5-dithione and the chalcogene is O or S, with N-aryl substituents or N-heteroaryl substituents instead of N-alkyl substituents, which exhibit high resistance against chemicals and solvents without loosing their other advantages like colourlessness, good light stability and good thermal stability.

DESCRIPTION OF THE INVENTION

It has now been found, surprisingly, that dithiolene metal complexes [M(L)$^2$], wherein L is selected from monoanions of a disubstituted imidazolidine-2-chalcogenone-4,5-dithione and the chalcogene is O or S, with N-perfluoroalkyl substituents instead of N-alkyl substituents, exhibit high resistance against chemicals and solvents without loosing their other advantages like colourlessness, good light stability and good thermal stability. They can be advantageously employed as IR absorbers for security printing and the laser-welding of plastics. Due to their unique application properties they are in particular suitable as IR absorbers for security printing, especially for bank notes.

In a first aspect, the invention provides metal dithiolene complexes of formula

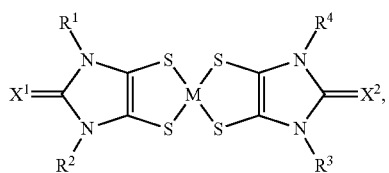

(I)

wherein
M is Ni, Pd, or Pt;
$X^1$ and $X^2$ are independently of each other sulphur, or oxygen;
at least one of the substituents $R^1$, $R^2$, $R^3$ and $R^4$ is a group —(CHR$^5$)$_n$—(CR$^6$F)$_m$—Z (R$_f$),
the substituents $R^1$, $R^2$, $R^3$ and $R^4$ are independently of each other a group R$_f$, an unsubstituted, or substituted alkyl group, or an unsubstituted, or substituted aryl group,
wherein the group R$_f$ may be interrupted by one, or more groups —O—, —NR$^8$—, —S—, —C(=O)—, —C(=O)O—, —C(=O)NR$^8$—, —S(=O)—, or —SO$_2$—;
Z is H, halogen, such as, for example, F, Cl, or Br, or

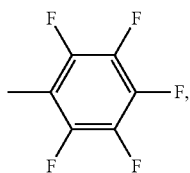

$R^5$ is H, CF$_3$, CH$_3$, or

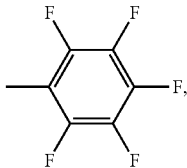

$R^6$ is F, CF$_3$, H, Cl, or Br,
if m is 2, groups —(CR$^6$F)— may be interrupted by CR$^9$H;
two groups R$^5$ together may form a double bond, or a group

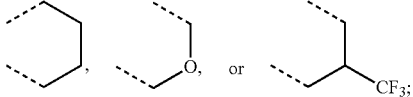

two groups R$^6$ together may form a double bond,
R$^5$ and R$^6$ together may form a double bond;
R$^6$ and Z together may form a double bond, or a group

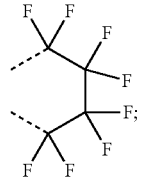

R$^9$ and R$^6$ together may form a double bond;
if two, or more groups R$^5$ are present within a group R$_f$, they can be the same, or different;
if two, or more groups R$^6$ are present within a group R$_f$, they can be the same, or different;
R$^8$ is a group R$_f$, H, an unsubstituted, or substituted alkyl group, especially a C$_1$-C$_{18}$alkyl group; or an unsubstituted, or substituted aryl group, especially an unsubstituted, or substituted phenyl group,
R$^9$ is H, or C$_1$-C$_4$alkyl;
m+n is an integer of 2 to 22,
n is 0, or an integer 1 to 7, and
m is an integer 1 to 15.

The metal dithiolene complexes of the general formula I may be used as colourless IR absorbers, for optical filters application; especially for plasma display panels, or for laser welding of plastics.

An especially suitable field of application is the use of the compounds of formula I in security printing and in the laser-welding of plastics material.

The compounds of the general formula I have at least one of the following advantageous properties:
good fastness to chemicals, in particular fastness to bleaching with hypochlorite and fastness to solvents (like toluene, acetone or dichloromethane),
good fastness to boiling water,
good fastness to light,
colourlessness (i.e. minimal absorption in the VIS range of the spectrum (from 400 to 700 nm))
good heat stability,
high compatibility with a multiplicity of formulations, in particular printing ink formulations used especially in security printing.

For definition and description of fastness requirements in banknote printing see e.g "Chemical and Physical Resistance" in "Extract of the ANNEX 13 of the Technical Specification for Euro banknote production" (European Central Bank; July 2004).

For illustration: nickel dithiolene complexes with simple alkyl substituents (like C-1, C-2, or C-3) are of high interest as colorless IR absorbers, but are of limited use for e.g. security printing due to their insufficient fastness against solvents like e.g. acetone, toluene, chlorobenzene, ethylacetate and 1,2-dichloroethane or against hypochlorite and boiling water.

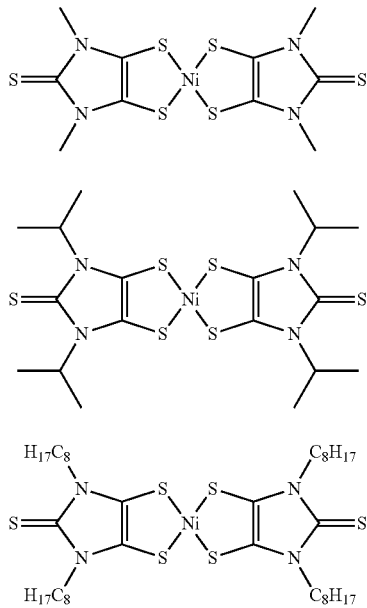

(C-1)

(C-2)

(C-3)

On the other hand nickel dithiolene complexes with perfluoro alkyl substituents like e.g. A-1, A-11, or A-24) exhibit very good resistance against the solvents mentioned above, hypochlorite and boiling water (cf. comparative example).

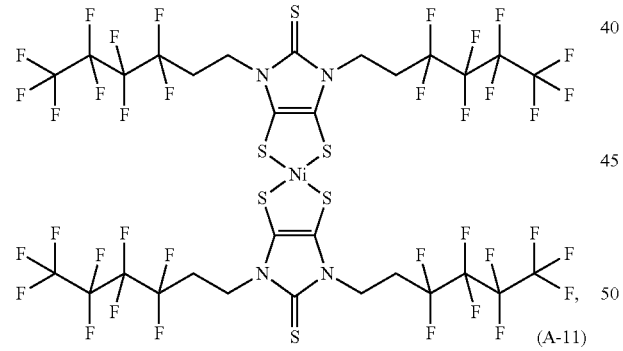

(A-1)

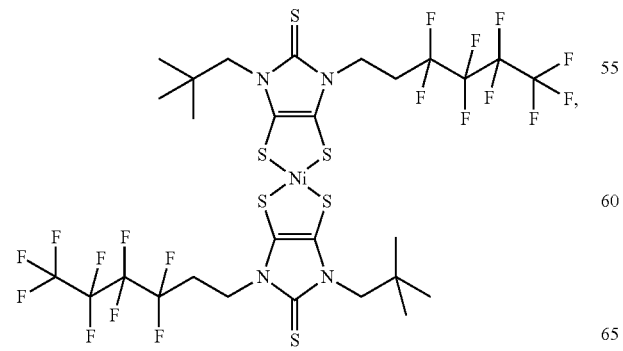

(A-11)

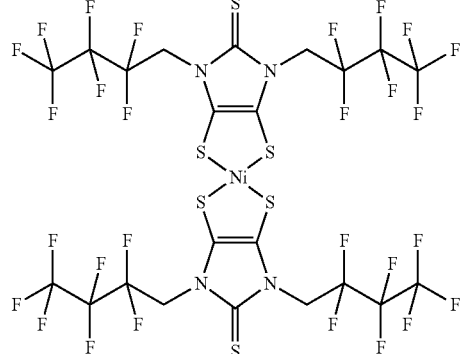

(A-24)

The compounds of general formula I can be used inter alia for security printing, invisible and/or IR readable bar codes, the laser-welding of plastics, the curing of surface-coatings using IR radiators, the drying and curing of print, the fixing of toners on paper or plastics, optical filters for plasma display panels, laser marking of paper or plastics, the heating of plastics preforms, and for heat shielding applications.

In a further aspect, the invention provides a printing ink formulation for security printing, comprising at least one compound of the formula X as defined below, especially at least one metal dithiolene complex of the general formula I as defined above and below.

In a further aspect, the invention provides a security document, comprising a substrate and at least one compound of the formula X as defined below, especially at least one metal dithiolene complex of the general formula I as defined above and below. The security document may be a bank note, a passport, a check, a voucher, an ID- or transaction card, a stamp and a tax label.

In a further aspect, the invention provides a security document, obtainable by a printing process, wherein a printing ink formulation is employed that comprises at least one compound of the formula X as defined below, especially at least one metal dithiolene complex of the general formula I as defined above and below.

$X^1$ and $X^2$ are independently of each other sulphur, or oxygen and are preferably sulphur.

The metal dithiolene complex is preferably a metal dithiolene complex of formula

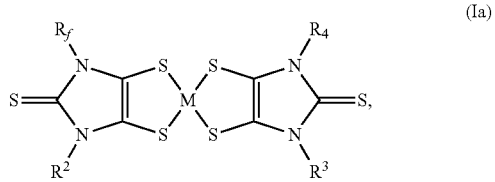

(Ia)

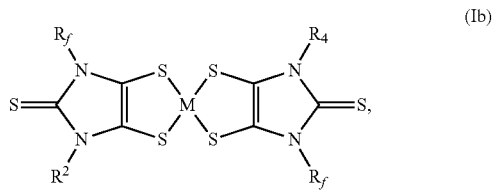

(Ib)

-continued

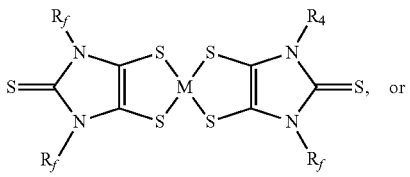
(Ic)

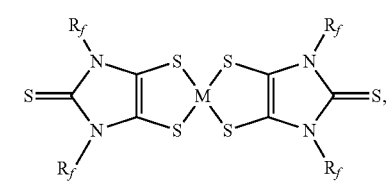
(Id)

wherein
M, $R_f$, $R^2$, $R^3$ and $R^4$ are as defined above. Metal dithiolene complexes of formula Ib and Id are more preferred.

The metal dithiolene complex of formula (Ib) can be present in form of two stereoisomers:

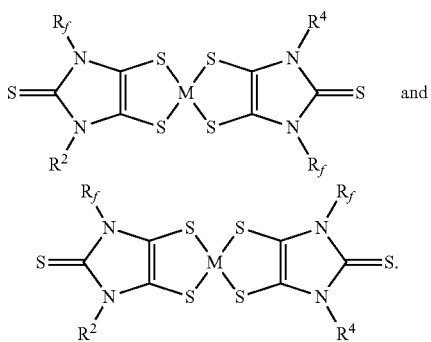

The notification

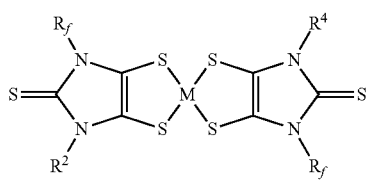

shall comprise both stereoisomers.

At least one of the substituents $R^1$, $R^2$, $R^3$ and $R^4$ is a group —$(CHR^5)_n$—$(CR^6F)_m$—Z ($R_f$). More preferred at least two of the substituents $R^1$, $R^2$, $R^3$ and $R^4$ are a group $R_f$, or all of the substituents $R^1$, $R^2$, $R^3$ and $R^4$ are a group $R_f$.

In a preferred embodiment the present invention is directed to metal dithiolene complexes of formula I, wherein two of the substituents $R^1$, $R^2$, $R^3$ and $R^4$ are a group $R_f$ and the other two of the substituents $R^1$, $R^2$, $R^3$ and $R^4$ are substituted or unsubstituted $C_1$-$C_{18}$alkyl radicals, including straight-chain and branched and also cyclic alkyl radicals; or all of the substituents $R^1$, $R^2$, $R^3$ and $R^4$ are a group $R_f$.

$R_f$ is preferably a group —$(CH_2)_n$—$(CF_2)_m$—F, wherein
n is an integer 1, or 2,
m is an integer 3 to 8, especially 3 to 5, and
m+n is an integer 4 to 10, especially 4 to 7.
Preferably, in the compounds of the general formula I M is Ni, Pd or Pt.

In particular, in the compounds of the general formula I M is Ni.
$R_f$ is a group —$(CHR^5)_n$—$(CR^6F)_m$—Z.
m+n is an integer of 2 to 22, n is 0, or an integer 1 to 7, and m is an integer 1 to 15.
Z is H, halogen, such as, for example, F, Cl, or Br, or

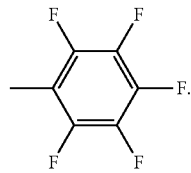

$R^5$ is H, $CF_3$, $CH_3$, or

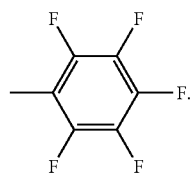

$R^6$ is F, $CF_3$, H, Cl, or Br.
The group $R_f$ may be interrupted by one, or more groups —O—, —$NR^8$—, —S—, —C(=O)—, —C(=O)O—, —C(=O)$NR^8$—, —S(=O), or —$SO_2$—. $R^8$ is a group $R_f$, H, an unsubstituted, or substituted alkyl group, or an unsubstituted, or substituted aryl group. $R^8$ is preferably a group $R_f$, or H.

If two, or more groups $R^5$ are present within a group $R_f$, they can be the same, or different.
If two, or more groups $R^6$ are present within a group $R_f$, they can be the same, or different.
If m is ≥2, groups —($CR^6F$)— may be interrupted by $CR^9H$. $R^9$ is H, or $C_1$-$C_4$alkyl.
Two groups $R^5$ together may form a double bond, or a group

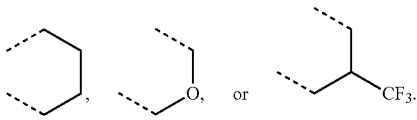

Two groups $R^6$ together may form a double bond. $R^5$ and $R^6$ together may form a double bond;
$R^6$ and Z together may form a double bond, or a group

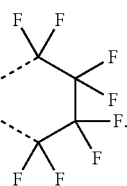

$R^9$ and $R^6$ together may form a double bond.
$R_f$ is preferably a group —$(CH_2)_n$—$(CF_2)_m$—Z, wherein Z is H, F, Cl, or Br, m+n is an integer of 2 to 22, n is 0, or an integer of 1 to 7, and m is an integer 1 to 15.

$R_f$ is more preferably a group $-(CH_2)_n-(CF_2)_m-F$, wherein m+n is an integer of 2 to 12, n is 0, or an integer of 1 to 5, and m is an integer of 2 to 12, especially m+n is an integer of 3 to 12, n is 0, 1, or 2, and m is an integer of 3 to 10.

Most preferred, $R_f$ is a group $-(CH_2)_n-(CF_2)_m-F$, wherein
n is an integer 1, or 2,
m is an integer 3 to 8, especially 3 to 5, and
m+n is an integer 4 to 10, especially 4 to 7.

The substituents $R_f$ can include olefinic double bonds and may be further substituted, branched, cyclic, or interrupted by e.g. $-O-$, $-NR^8-$, $-S-$, $-C(=O)-$, $-C(=O)O-$, $-C(=O)NR^8-$, $-S(=O)$, or $-SO_2-$. For $-(CF_2)_m-$ some fluorine atoms may be replaced by hydrogen, or other halogen atoms like chlorine and bromine.

Examples for $R_f$ are given for illustration below:

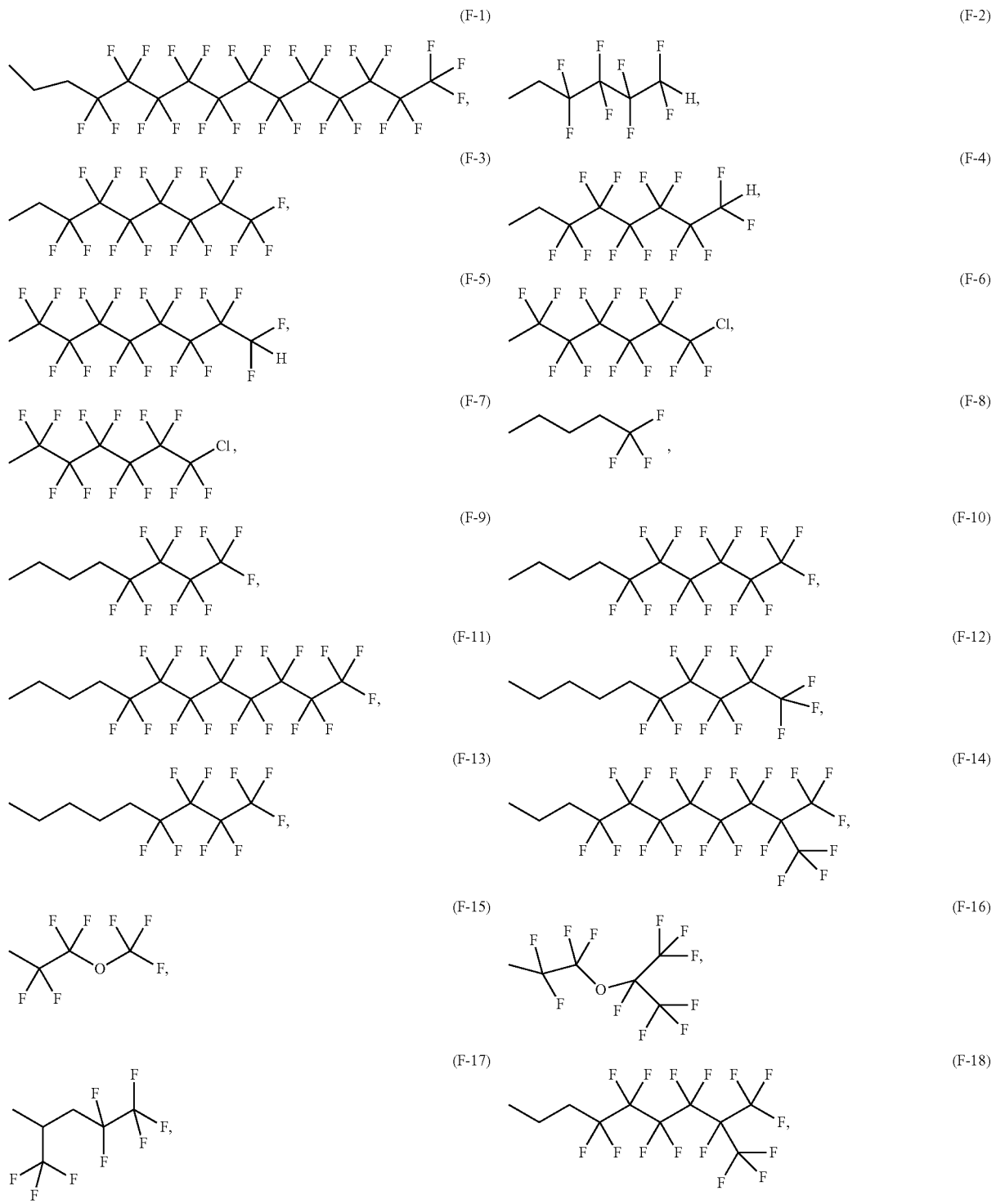

-continued
(F-19) 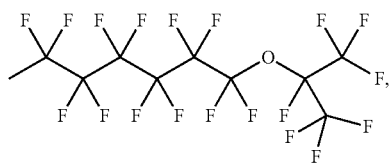
(F-20) 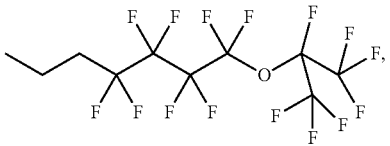
(F-21) 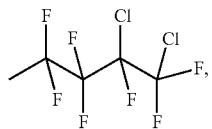
(F-22) 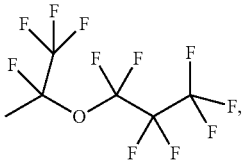
(F-23) 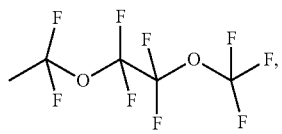
(F-24) 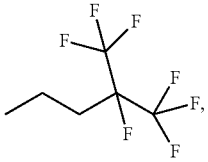
(F-25) 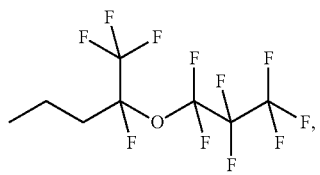
(F-26) 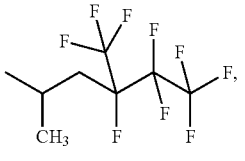
(F-27) 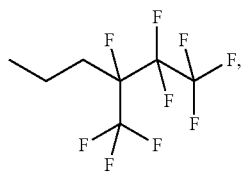
(F-28) 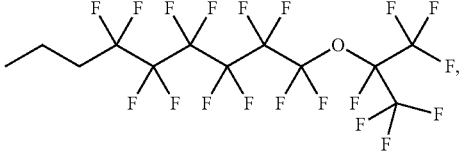
(F-29) 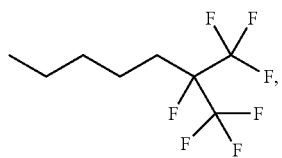
(F-30) 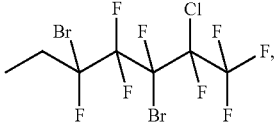
(F-31) 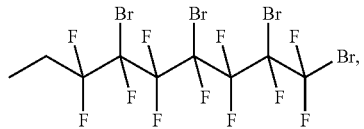
(F-32) 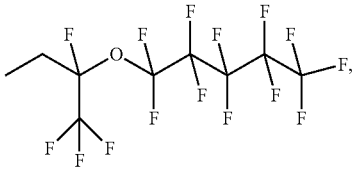
(F-33) 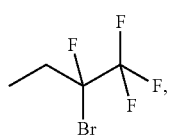
(F-34) 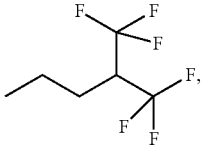
(F-35) 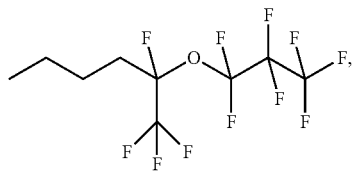
(F-36) 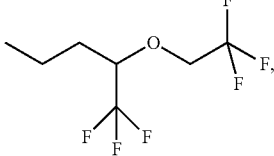

-continued
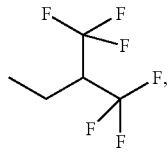
(F-37)
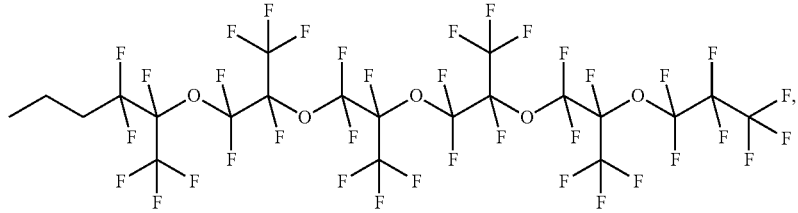
(F-38)
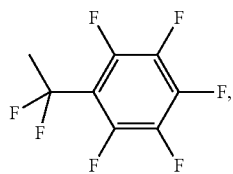
(F-39)
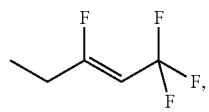
(F-40)
(F-41)
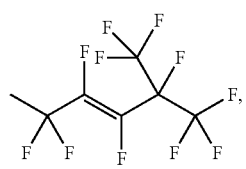
(F-42)
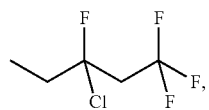
(F-43)
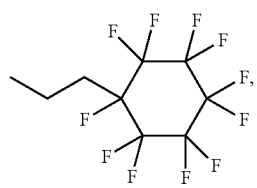
(F-44)
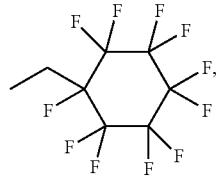
(F-45)
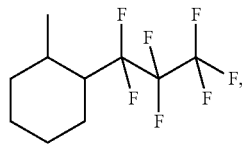
(F-46)
(F-47)
(F-48)
(F-49)
(F-50)

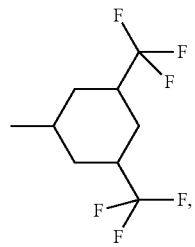

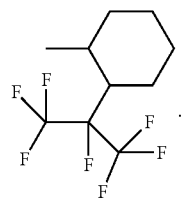

-continued

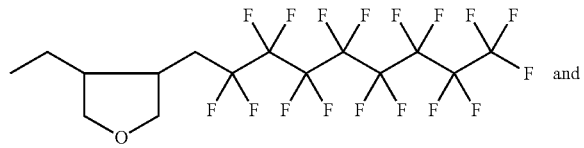
(F-51)

(F-52) and (F-53)

In a particularly preferred embodiment of the present invention two of the substituents $R^1$, $R^2$, $R^3$ and $R^4$ are a group —$(CH_2)_n$—$(CF_2)_m$—F, wherein m+n is an integer of 4 to 7, n is 1, or 2, m is an integer 3 to 5, and the other two of the substituents $R^1$, $R^2$, $R^3$ and $R^4$ are substituted or unsubstituted $C_1$-$C_{18}$ alkyl groups, including straight-chain and branched and also cyclic alkyl radicals; or all of the substituents $R^1$, $R^2$, $R^3$ and $R^4$ are a group —$(CH_2)_n$—$(CF_2)_m$—F.

The following may be mentioned as examples of $C_1$-$C_{18}$ alkyl groups: methyl, ethyl, propyl, isopropyl, n-butyl, sec-butyl, tert-butyl, neo-pentyl, n-hexyl, cyclopentyl, cyclohexyl, 2-ethylhexyl, n-dodecyl, n-hexadeyl and n-octadecyl.

Examples of the metal dithiolene complex of formula I are the metal dithiolene complexes A-1 to A-57. Reference is made to claim 6. Metal dithiolene complexes A-1 to A-5, A-8; A-11 to A-14, A-17 to A-19, A-24, A-25, A-28, A-29, A-35, A-36, A-39, A-42, A-56 and A-57 are preferred, metal dithiolene complexes A-1 to A-4, A-11 to A-13, A-17 to A-19, A-24, A-25, A-28, A-35 and A-36 are most preferred.

Metal dithiolene complexes of formula

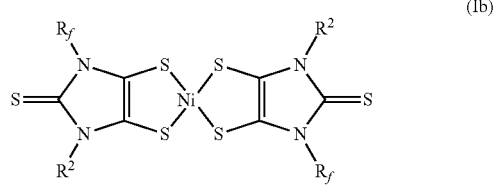
(Ib)

can be obtained by reacting a compound of formula

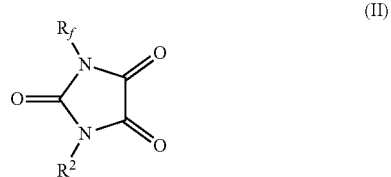
(II)

with metallic nickel and Lawesson's reagent

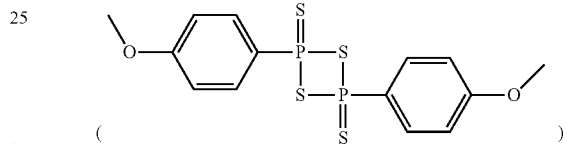

in a solvent, such as, for example, chlorobenzene under reflux conditions.

Metal dithiolene complexes of the general formula I, wherein $X^1$ is O and $X^2$ is S, can be obtained from the corresponding sulfur compounds ($X^1$, $X^2$=S) by oxidation in a suitable solvent. Suitable oxidation agents are oxygen and oxygen containing gas mixtures, in particular atmospheric oxygen. Suitable solvents are inert under the oxidation conditions. Preferred solvents are halogenated hydrocarbons, e.g. dichloromethane.

Metal dithiolene complexes of the general formula I, wherein $X^1$ is oxygen and $X^2$ is sulfur or oxygen can also be obtained from disubstituted imidazolidine-2,4,5-triones of the formula

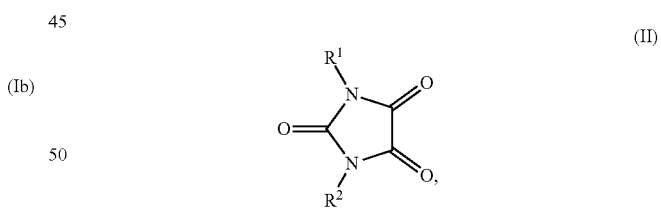
(II)

wherein $R^1$ and $R^2$ have one of the aforementioned meanings. Suitable methods are described in WO2008/086931 which is incorporated herein by reference.

Disubstituted imidazolidine-2,4,5-triones of the formula

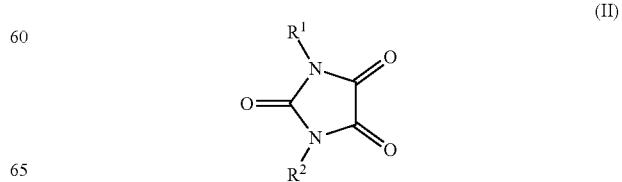
(II)

can be, for example, prepared by reacting an isothiocyanate R¹—N=C=S with an amine R²—NH₂, or stepwise addition of two different amines R¹—NH₂ and R²—NH₂ to CS₂; and then reacting the obtained intermediate with oxalyl chloride.

Disubstituted imidazolidine-2,4,5-triones of the formula

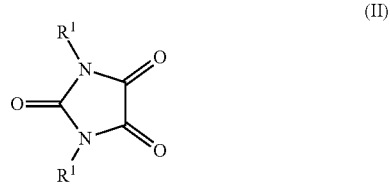

(II)

can be, for example, prepared by reacting carbondisulfide with an amine R¹—NH₂ and then reacting the obtained intermediate with oxalyl chloride.

In the context of the invention, the expression "halogen" denotes in each case fluorine, bromine, chlorine or iodine, preferably fluorine, chlorine or bromine, in particular fluorine or chlorine.

In the context of the present invention, the expression "alkyl" comprises straight-chain or branched alkyl groups. Alkyl is preferably $C_1$-$C_{30}$-alkyl, more preferably $C_1$-$C_{20}$-alkyl, most preferably $C_1$-$C_{12}$-alkyl, in particular $C_1$-$C_6$-alkyl. Examples of alkyl groups are especially methyl, ethyl, n-propyl, isopropyl, n-butyl, isobutyl, sec-butyl, tert-butyl, n-pentyl, neo-pentyl, n-hexyl, n-heptyl, n-octyl, n-nonyl, n-decyl, n-undecyl, n-dodecyl, n-tridecyl, n-tetradecyl, n-hexadecyl, n-octadecyl and n-eicosyl.

The expression alkyl also comprises alkyl radicals whose carbon chains may be interrupted by one or more groups which are independently selected from —O— and —S—.

Substituted alkyl groups may, depending on the length of the alkyl chain, have one or more (e.g. 1, 2, 3, 4, 5 or more than 5) substituents. These are preferably each independently selected from cycloalkyl, heterocycloalkyl, aryl, heteroaryl, fluorine, chlorine, bromine, hydroxyl, mercapto, cyano, nitro, nitroso, formyl, acyl, COOH, carboxylate, alkylcarbonyloxy, carbamoyl, alkylaminocarbonyl, (dialkylamino)carbonyl, $SO_3H$, sulfonate, sulfoamino, sulfamide, sulfamoyl, amidino, $NE^1E^2$ where $E^1$ and $E^2$ are each independently hydrogen, alkyl, cycloalkyl, heterocycloalkyl, aryl or heteroaryl. Cycloalkyl, heterocycloalkyl, aryl and heteroaryl substituents of the alkyl groups may in turn be unsubstituted or substituted; suitable substituents are the substituents mentioned below for these groups.

The expression substituted alkyl group also comprises alkyl radicals that have one or more (e.g. 1, 2, 3, 4, 5 or more than 5) substituents and whose carbon chains may be interrupted by one or more groups which are independently selected from —O— and —S—.

Carboxylate and sulfonate respectively represent a metal carboxylate or metal sulfonate, or a carboxylic ester function or sulfonic ester function.

The above remarks regarding alkyl also apply to the alkyl moiety in alkoxy, alkylthio (=alkylsulfanyl), monoalkylamino and dialkylamino.

In the context of the present invention, the term "cycloalkyl" denotes a mono-, bi- or tricyclic hydrocarbon radical having usually from 3 to 20, preferably 3 to 12, more preferably 5 to 12, carbon atoms such as cyclopropyl, cyclobutyl, cyclopentyl, cyclohexyl, cycloheptyl, cyclooctyl, cyclododecyl, cyclopentadecyl, norbornyl, bicyclo[2.2.2]octyl or adamantyl.

Substituted cycloalkyl groups may, depending on the ring size, have one or more (e.g. 1, 2, 3, 4, 5 or more than 5) substituents. These are preferably each independently selected from alkyl, alkoxy, alkylthio, cycloalkyl, heterocycloalkyl, aryl, heteroaryl, fluorine, chlorine, bromine, hydroxyl, mercapto, cyano, nitro, nitroso, formyl, acyl, COOH, carboxylate, alkylcarbonyloxy, carbamoyl, $SO_3H$, sulfonate, sulfamino, sulfamide, amidino, $NE^3E^4$ where $E^3$ and $E^4$ are each independently hydrogen, alkyl, cycloalkyl, heterocycloalkyl, aryl or heteroaryl. In the case of substitution, the cycloalkyl groups preferably bear one or more, for example one, two, three, four or five, $C_1$-$C_6$-alkyl groups. Examples of substituted cycloalkyl groups are especially 2- and 3-methylcyclopentyl, 2- and 3-ethylcyclopentyl, 2-, 3- and 4-methylcyclohexyl, 2-, 3- and 4-ethylcyclohexyl, 2-, 3- and 4-propylcyclohexyl, 2-, 3- and 4-isopropylcyclohexyl, 2-, 3- and 4-butylcyclohexyl, 2-, 3- and 4-sec.-butylcyclohexyl, 2-, 3- and 4-tert-butylcyclohexyl, 2-, 3- and 4-methylcycloheptyl, 2-, 3- and 4-ethylcycloheptyl, 2-, 3- and 4-propylcycloheptyl, 2-, 3- and 4-isopropylcycloheptyl, 2-, 3- and 4-butylcycloheptyl, 2-, 3- and 4-sec-butylcycloheptyl, 2-, 3- and 4-tert-butylcycloheptyl, 2-, 3-, 4- and 5-methylcyclooctyl, 2-, 3-, 4- and 5-ethylcyclooctyl, 2-, 3-, 4- and 5-propylcyclooctyl.

The above remarks regarding cycloalkyl also apply to the cycloalkyl moiety in cycloalkoxy, cycloalkylthio (=cycloalkylsulfanyl), monocycloalkylamino and dicycloalkylamino.

In the context of the present invention, the expression "heterocycloalkyl" comprises nonaromatic, unsaturated or fully saturated, cycloaliphatic groups having generally 5 to 8 ring atoms, preferably 5 or 6 ring atoms. In the heterocycloalkyl groups, compared to the corresponding cycloalkyl groups, 1, 2, 3, 4 or more than 4 of the ring carbon atoms are replaced by heteroatoms or heteroatom-containing groups. The heteroatoms or heteroatom-containing groups are preferably selected from —O—, —S—, —NR$^a$—, —C(=O)—, —S(=O)— and/or —S(=O)₂—. R$^a$ is preferably hydrogen, alkyl, cycloalkyl, heterocycloalkyl, aryl or heteroaryl. Examples of heterocycloalkyl groups are especially pyrrolidinyl, piperidinyl, imidazolidinyl, pyrazolidinyl, oxazolidinyl, morpholinyl, thiazolidinyl, isothiazolidinyl, isoxazolidinyl, piperazinyl, tetrahydrothiophenyl, dihydrothien-2-yl, tetrahydrofuranyl, dihydrofuran-2-yl, tetrahydropyranyl, 2-oxazolinyl, 3-oxazolinyl, 4-oxazolinyl and dioxanyl.

Substituted heterocycloalkyl groups may, depending on the ring size, have one or more (e.g. 1, 2, 3, 4, 5 or more than 5) substituents. These are preferably each independently selected from alkyl, alkoxy, alkylthio, cycloalkyl, heterocycloalkyl, aryl, heteroaryl, fluorine, chlorine, bromine, hydroxyl, mercapto, cyano, nitro, nitroso, formyl, acyl, COOH, carboxylate, alkylcarbonyloxy, carbamoyl, alkylaminocarbonyl, (dialkylamino)carbonyl, $SO_3H$, sulfonate, sulfoamino, sulfamide, sulfamoyl, amidino, $NE^5E^6$ where $E^5$ and $E^6$ are each independently hydrogen, alkyl, cycloalkyl, heterocycloalkyl, aryl or heteroaryl. In the case of substitution, the heterocycloalkyl groups preferably bear one or more, for example one, two, three, four or five, $C_1$-$C_6$-alkyl groups.

The above remarks regarding heterocycloalkyl also apply to the heterocycloalkyl moiety in heterocycloalkoxy, heterocycloalkylthio (=heterocycloalkylsulfanyl), (monoheterocycloalkyl)amino and (diheterocycloalkyl)amino.

In the context of the present invention, the term "aryl" refers to mono- or polycyclic aromatic hydrocarbon radicals. Suitable and preferred unsubstituted and substituted aryl groups are defined below.

In the context of the present invention, the term "heteroaryl" (hetaryl) refers to unsubstituted or substituted heteroaromatic, mono- or polycyclic groups. Suitable and preferred unsubstituted and substituted heteroaryl groups are defined below.

The unsubstituted or substituted aryl groups are independently selected from unsubstituted or substituted mono- or polycyclic aromatic hydrocarbon radicals, preferably having 6 to 24 carbon atoms, more preferably having 6 to 20 carbon atoms, especially having 6 to 14 carbon atoms as ring members.

The unsubstituted or substituted aryl groups are preferably selected from unsubstituted or substituted phenyl, unsubstituted or substituted naphthyl, unsubstituted or substituted indenyl, unsubstituted or substituted fluorenyl, unsubstituted or substituted anthracenyl, unsubstituted or substituted phenanthrenyl, unsubstituted or substituted naphthacenyl, unsubstituted or substituted chrysenyl, unsubstituted or substituted pyrenyl, unsubstituted or substituted coronenyl and unsubstituted or substituted perylenyl.

The unsubstituted or substituted aryl groups are more preferably selected from unsubstituted or substituted phenyl and unsubstituted or substituted naphthyl.

The unsubstituted or substituted aryl groups are in particular selected from unsubstituted or substituted phenyl.

The substituted aryl groups may, depending on the number and size of their ring systems, have one or more (e.g. 1, 2, 3, 4, 5 or more than 5) substituents. The substituents of the substituted aryl groups are preferably each independently selected from alkyl, alkoxy, alkylthio, cycloalkyl, heterocycloalkyl, aryl, heteroaryl, fluorine, chlorine, bromine, hydroxyl, mercapto, cyano, nitro, nitroso, formyl, acyl, COOH, carboxylate, alkylcarbonyloxy, carbamoyl, $SO_3H$, sulfonate, sulfamino, sulfamide, amidino, $NE^1E^2$ where $E^1$ and $E^2$ are each independently hydrogen, alkyl, cycloalkyl, heterocycloalkyl, aryl or heteroaryl. The alkyl, alkoxy, alkylamino, alkylthio, cycloalkyl, heterocycloalkyl, aryl and heteroaryl substituents on the substituted aryl groups may in turn be unsubstituted or substituted. Reference is made to the substituents mentioned for these groups above and in the following.

The substituents on the substituted aryl groups are preferably selected from alkyl; alkoxy; alkyl or alkoxy whose carbon chain is interrupted by one or more nonadjacent groups selected from —O—, —S—, —$NR^a$—, —C(=O)—, —S(=O)— and/or —$S(=O)_2$—, wherein $R^a$ is hydrogen, alkyl, cycloalkyl, heterocycloalkyl, aryl or heteroaryl; haloalkyl; haloalkoxy; cycloalkyl; fluorine; chlorine; bromine; cyano and nitro.

The substituted aryl groups are preferably substituted phenyl which bears 1, 2, 3, 4 or 5 substituents. The substituted aryl groups are more preferably substituted phenyl which bears preferably 1, 2 or 3 substituents.

The substituted aryl groups are preferably selected from aryl groups substituted by at least one alkyl group ("alkaryl", also referred to as alkylaryl). Alkaryl groups may, depending on the size of the aromatic ring system, have one or more (e.g. 1, 2, 3, 4, 5, 6, 7, 8, 9 or more than 9) alkyl substituents. The alkyl substituents on the alkaryl groups may be unsubstituted or substituted. In this regard, reference is made to the above statements regarding unsubstituted and substituted alkyl. In a preferred embodiment, the alkaryl groups have exclusively unsubstituted alkyl substituents. Alkaryl is preferably phenyl which bears 1, 2, 3, 4 or 5, preferably 1, 2 or 3, more preferably 1 or 2, alkyl substituents. The alkyl substituents on the alkaryl groups are preferably selected from $C_1$-$C_{20}$-alkyl, more preferably $C_1$-$C_{12}$-alkyl and most preferably $C_1$-$C_6$-alkyl. Examples of alkyl groups are especially methyl, ethyl, n-propyl, isopropyl, n-butyl, isobutyl, sec-butyl, tert-butyl, n-pentyl, neo-pentyl, n-hexyl, n-heptyl, n-octyl, n-nonyl, n-decyl, n-undecyl, n-dodecyl, n-tridecyl, n-tetradecyl, n-hexadecyl, n-octadecyl and n-eicosyl.

Unsubstituted or substituted heteroaryl groups are independently selected from unsubstituted or substituted heteroaromatic, mono- or polycyclic groups. In addition to the ring carbon atoms, these have 1, 2, 3, 4 or more than 4 heteroatoms as ring members. The heteroatoms are preferably selected from oxygen, nitrogen, selenium and sulfur. The heteroaryl groups have preferably 5 to 18, e.g. 5, 6, 8, 9, 10, 11, 12, 13 or 14, ring atoms.

Unsubstituted or substituted monocyclic heteroaryl groups are preferably selected from unsubstituted or substituted 5- or 6-membered heteroaryl groups, such as 2-furyl (furan-2-yl), 3-furyl (furan-3-yl), 2-thienyl (thiophen-2-yl), 3-thienyl (thiophen-3-yl), selenophen-2-yl, selenophen-3-yl, 1H-pyrrol-2-yl, 1H-pyrrol-3-yl, imidazol-4-yl, pyrazol-1-yl, pyrazol-3-yl, pyrazol-4-yl, pyrazol-5-yl, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 1,2,4-oxadiazol-3-yl, 1,2,4-oxadiazol-5-yl, 1,3,4-oxadiazol-2-yl, 1,2,4-thiadiazol-3-yl, 1,2,4-thiadiazol-5-yl, 1,3,4-thiadiazol-2-yl, 4H-[1,2,4]-triazol-3-yl, 1,3,4-triazol-2-yl, 1,2,3-triazol-1-yl, 1,2,4-triazol-1-yl, pyridin-2-yl, pyridin-3-yl, pyridin-4-yl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

Unsubstituted or substituted polycyclic heteroaryl groups preferably have 2, 3, 4 or more than 4 fused rings. The fused-on rings may be aromatic, saturated or partly unsaturated. Examples of polycyclic heteroaryl groups are quinolinyl, isoquinolinyl, indolyl, isoindolyl, indolizinyl, benzofuranyl, isobenzofuranyl, benzothiophenyl, benzoxazolyl, benzisoxazolyl, benzthiazolyl, benzoxadiazolyl, benzothiadiazolyl, benzoxazinyl, benzopyrazolyl, benzimidazolyl, benzotriazolyl, benzotriazinyl, benzoselenophenyl, thienothiophenyl, thienopyrimidyl, thiazolothiazolyl, dibenzopyrrolyl(carbazolyl), dibenzofuranyl, dibenzothiophenyl, naphtho[2,3-b]thiophenyl, naphtha[2,3-b]furyl, dihydroindolyl, dihydroindolizinyl, dihydroisoindolyl, dihydroquinolinyl and dihydroisoquinolinyl.

The substituted hetaryl groups may, depending on the number and size of their ring systems, have one or more (e.g. 1, 2, 3, 4, 5 or more than 5) substituents. These are preferably each independently selected from alkyl, alkoxy, alkylthio, cycloalkyl, heterocycloalkyl, aryl, heteroaryl, fluorine, chlorine, bromine, hydroxyl, mercapto, cyano, nitro, nitroso, formyl, acyl, COOH, carboxylate, alkylcarbonyloxy, carbamoyl, $SO_3H$, sulfonate, sulfamino, sulfamide, amidino, $NE^3E^4$ where $E^3$ and $E^4$ are each independently hydrogen, alkyl, cycloalkyl, heterocycloalkyl, aryl or heteroaryl. Halogen substituents are preferably fluorine, chlorine or bromine.

The substituents on the substituted hetaryl groups are preferably selected from alkyl; alkoxy; alkyl or alkoxy whose carbon chain is interrupted by one or more nonadjacent groups selected from —O—, —S—, —$NR^b$—, —C(=O)—, —S(=O)— and/or —$S(=O)_2$—, wherein $R^b$ is hydrogen, alkyl, cycloalkyl, heterocycloalkyl, aryl or heteroaryl; haloalkyl; haloalkoxy; cycloalkyl; fluorine; chlorine; bromine; cyano and nitro.

The substituted hetaryl groups are preferably selected from heteroaryl groups substituted by at least one alkyl group. Alkyl substituted heteroaryl groups may, depending on the size of the aromatic ring system, have one or more (e.g. 1, 2, 3, 4, 5, 6, 7, 8, 9 or more than 9) alkyl substituents. The alkyl substituents on the heteroaryl groups may be unsubstituted or substituted. In this regard, reference is made to the following statements regarding unsubstituted and substituted alkyl. In a preferred embodiment, the heteroaryl groups have exclusively unsubstituted alkyl substituents. The alkyl substituents on the hetaryl groups are preferably selected from $C_1$-$C_{20}$-alkyl, more preferably $C_1$-$C_{12}$-alkyl and most preferably $C_1$-$C_6$-alkyl. Examples of alkyl groups are especially methyl, ethyl, n-propyl, isopropyl, n-butyl, isobutyl, sec-butyl, tert-butyl, n-pentyl, neo-pentyl, n-hexyl, n-heptyl, n-octyl, n-nonyl, n-decyl, n-undecyl, n-dodecyl, n-tridecyl, n-tetradecyl, n-hexadecyl, n-octadecyl and n-eicosyl.

The IR absorbers of formula I can also be used in the form of a mixture, comprising at least one compound of the general formula I and at least one further IR absorber different from compounds of the general formula I. Suitable further IR absorbers are in principle all known classes of IR absorbers that are compatible with the compounds of the general formula I. Preferred further IR absorbers are selected from polymethines, phthalocyanines, naphthalocyanines, quinone-diimmonium salts, aminium salts, rylenes, inorganic IR absorbers and mixtures thereof. Further polymethine IR absorbers are preferably selected from cyanines, squaraines, croconaines and mixtures thereof. Further inorganic IR absorbers are preferably selected from indium tin oxide, antimony tin oxide, lanthanum hexaboride, tungsten bronzes, copper salts etc.

The IR absorbers can be generally used in a concentration of from 10 ppm to 25%, preferably 100 ppm to 10%, depending on the chosen application.

The afore-mentioned IR absorbers of the general formula I and IR absorber mixtures are especially suitable for laser welding of plastics.

The laser welding is preferably carried out using an ND:YAG laser at 1064 nm or using a diode laser at 980 nm or 940 nm. The concentration of the IR absorber of the general formula I or an IR absorber mixtures is e.g. from 5 to 500 ppm, preferably from 10 to 200 ppm.

In laser welding, plastics components are welded to one another. The plastics components to be fused may have any shape. For example, at least one of the plastics components may be a film.

The metal dithiolene complexes of the general formula I according to the invention are suitable for welding transparent at least translucent plastics materials. The employed plastics materials may be colourless or coloured. In principle, the plastics components to be fused may be composed of the same polymer or of different polymers. Preferably, the plastics components employed for laser welding are selected from thermoplastic polymers. However, it is also possible that neither of the plastics components to be fused is composed of thermoplastic; however, a coating of at least one part with a thermoplastic comprising at least one metal dithiolene complex of the general formula I is required.

The plastics components employed for laser welding preferably comprise or consist of at least one polymer selected from polyolefins, polyolefin copolymers, polytetrafluoroethylenes, ethylene-tetrafluoroethylene copolymers, polyvinyl chlorides, polyvinylidene chlorides, polyvinyl alcohols, polyvinyl esters, polyvinyl alkanals, polyvinyl ketals, polyamides, polyimides, polycarbonates, polycarbonate blends, polyesters, polyester blends, poly(meth)acrylates, poly(meth)acrylate-styrene copolymer blends, poly(meth)acrylatepolyvinylidene difluoride blends, polyurethanes, polystyrenes, styrene copolymers, polyethers, polyether ketones and polysulfones and mixtures thereof.

Preference is given to matrix polymers from the group of the polyolefins, polyolefin copolymers, polyvinyl alkanals, polyamides, polycarbonates, polycarbonate-polyester blends, polycarbonate-styrene copolymer blends, polyesters, polyester blends, poly(meth)acrylates, poly(meth)acrylate-styrene copolymer blends, poly(meth)acrylatepolyvinylidene difluoride blends, styrene copolymers and polysulfones and mixtures thereof.

Particularly preferred polymers are transparent or at least translucent. Examples include: polypropylene, polyvinylbutyral, nylon-[6], nylon-[6,6], polycarbonate, polycarbonate-polyethylene terephthalate blends, polycarbonate-polybutylene terephthalate blends, polycarbonate-acrylonitrile/styrene/acrylonitrile copolymer blends, polycarbonateacrylonitrile/butadiene/styrene copolymer blends, polymethyl methacrylateacrylonitrile/butadiene/styrene copolymer blends (MABS), polyethylene terephthalate, polybutylene terephthalate, polymethyl methacrylate, impact-modified polymethyl methacrylate, polybutyl acrylate, polymethyl methacrylate-polyvinylidene difluoride blends, acrylonitrile/butadiene/styrene copolymers (ABS), styrene/acrylonitrile copolymers (SAN), polyphenylenesulfone and mixtures comprising 2 or more (e.g. 2, 3, 4, 5) of the afore-mentioned polymers.

Suitable polymer preparations for laser welding comprise
A) a thermoplastic matrix polymer suitable for forming the plastics parts,
B) at least one metal dithiolene complex of the general formula I as defined before,
C) optionally at least one further additive.

Those polymer preparations for laser welding are likewise in accordance with the invention and are suitable for producing fusion-bonded plastics parts with the aid of laser radiation whose wavelength is outside the visible region.

Polymer preparations for laser welding may advantageously be produced by a conventional extrusion or kneading process. The components B), and, if present, C) may be mixed from the outset, in the weight ratio corresponding to the desired end concentration, with the matrix polymer A) (direct compounding), or a distinctly higher concentration of B) and, if present, C) may initially be selected and the concentrate formed (masterbatch) subsequently diluted with further matrix polymer A) in the course of the manufacture of the parts to be fused.

Suitable additives C) are UV stabilizers, antioxidants, processing plasticizers, etc.

In addition, the polymer preparations for laser welding may comprise at least one colorant for establishing a desired hue as additive, especially transparent organic pigments and in particular dyes, for example C.I. Pigment Yellow 138, 139, 147, 183, 185 192 and 196, C.I. Pigment Orange 70, C.I. Pigment Red 149, 178 and 179, 181, 263, C.I. Pigment Violet 19 and 29, C.I. Pigment Blue 15, 15:1, 15:3 and 15:4, C.I. Pigment Green 7 and 36, C.I. Solvent Yellow 14, 21, 93, 130, 133, 145, 163, C.I. Solvent Red 52, 135, 195, 213, 214 and 225, C.I. Solvent Blue 35, 45, 67, 68, 97, 104, 122, 132, C.I. Solvent Violet 13, 46, 49, C.I. Solvent Green 3, 5 and 28, C.I. Solvent Orange 47, 60, 86, 114, and 163, C.I. Solvent Brown 35, 53, and also C.I. Disperse Yellow 54, 87, 201, C.I. Disperse Orange 30, C.I. Disperse Red 60 and C.I. Disperse Violet 57

A further possible additive group is that of additives which likewise modify the visual appearance, the mechanical properties or else the tactile properties, for example matting agents, such as titanium dioxide, chalk, barium sulfate, zinc sulfide, fillers, such as nano-particulate silicon dioxide, aluminium hydroxide, clay and other sheet silicates, glass fibers and glass spheres.

The afore-mentioned IR absorbers of the general formula I and IR absorber mixtures are also especially suitable for security printing.

Security printing is the field that deals with the printing of items such as currency, passports, tamper-evident labels, stock certificates, postage stamps, identity cards, etc. The main goal of security printing is to prevent forgery, tampering or counterfeiting.

In the field of automated banknote processing, IR-absorption plays an important role. Most of the actually circulating currency carries not only visibly coloured printings, but also specific features which are only detectable in the infrared part of the spectrum. Generally, these IR-features are implemented for use by automatic currency processing equipment, in banking and vending applications (automatic teller machines, automatic vending machines, etc.), in order to recognize a determined currency bill and to verify its authenticity, in particular to discriminate it from replicas made by colour copiers.

All security documents are required to have good stability and durability. In the case of bank notes, these requirements are extreme, as bank notes are subjected to toughest use conditions by the public—they are subjected to material stress by folding, crumpling etc., subjected to abrasion, exposed to weather, exposed to bodily fluids such as perspiration, laundered, dry-cleaned, ironed etc.—and, after having been subjected to this, are expected to be as legible as when they started. Furthermore, it is essential that the documents nevertheless should have a reasonable life time, ideally of some years, despite suffering the afore-mentioned conditions. During this time, the documents, and thus the inks on them (including invisible security markings), should be resistant to fading or colour change. Hence, any ink used in a security printing process should, when cured, be robust, water-resistant, resistant to various chemicals and flexible. Moreover, as certain states are moving away from the use of paper as the substrate for bank notes, the employed printing ink formulations should be useable on plastics as well as paper.

In a further aspect the present invention is directed to the use of compounds of the formula $Ch-[(L)_y-(R_f)]_x$ (X), especially the metal dithiolene complexes of formula I for security printing, especially security printing of bank notes. The compounds of formula X exhibit improved resistance against chemicals and solvents when bearing perfluoroalkyl substituents.

Colorants with perfluoro substituents have been described in several patent applications.

U.S. Pat. No. 3,281,426 describes the preparation of perfluoroalkylated copper phthalocyanine and vat dyes.

U.S. Pat. Nos. 5,932,721 and 6,043,355 claim novel phthalocyanine compounds with fluorine-atom substituted alkyl groups which can be employed as a dye for optical recording, for color filter application or as a material for use in photoelectric conversion device, electrophotographic photoconductor, organic semiconductor device, catalysts and gas sensor.

U.S. Pat. No. 7,390,901 (cf. WO2005/017046) relate to novel fluorinated colorants having high solubility and low viscosity in halogenated, especially fluorinated solvents. The colorants of this invention show improved performance for electrophoretic displays. The following chromophores are mentioned: phthalocyanine, naphthalocyanine, anthraquinone, perylene, quinacridone, diketopyrrolopyrrole, porphyrin and naphthalimide.

Phthalo- and naphthalocyanines with perfluoroalkyl substituents for application in electrophoretic display fluids are disclosed in WO2004/027506.

Rylene type dyes with perfluoroalkyl substituents have been described too for use in electrophoretic displays (WO2008/128934).

WO2009/000756 claims the use of specific perylenes with perfluoroalkyl substituents as charge transport materials or exciton transport materials in exitonic solar cells and electron conductors in organic solar cells.

WO2006/086349 describes coating compositions comprising perfluoroalkyl perfluoro phthalocyanines for use as functional coating(s). These functional coatings advantageously exhibit one or more of the following properties: variable optical, electrical and/or magnetic properties, enhanced durability, and/or enhanced resistance to chemical and/or biological surface contamination.

JP07246775 claims phthalocyanines with fluorine-substituted alkoxy groups for optical information recording and finally RU2033572 discloses fluorine substituted diphthalocyanines as optical filters.

EP1088559 claims galenic formulations of perfluoroalkyl dyes (especially cyanine dyes) for diagnostic applications.

Azo dyes with perfluoroalkyl substituents for use as e.g. functional colorant for LCD device or heat sensitive recording material have been disclosed in JP05255221.

EP499281 describes soluble dyes for polyfluoro-polyoxyalkylenes with chromophores bonded to perfluoro-oxyalkylene chain.

Anthraquinone dyes with fluoroalkyl (JP05246933) or fluoroalkoxy groups have been claimed for dyeing or as recording material.

Novel yellow to red dyes with fluoroaliphatic groups have been described in U.S. Pat. Nos. 3,933,914 and 4,018,810 and reactive dyes with fluorinated side chains have been described in 2 patent applications (GB1238913, FR1582620).

It has now been found that compounds of the formula X, especially the metal dithiolene complexes of formula I, because of their unique application properties are especially suitable for printing ink formulations that are employed for security printing and in particular for bank notes.

That is, not only IR absorbers (chromophores absorbing radiation in the infra red spectral range) but also chromophores absorbing in the visible range of the spectrum (dyes) or in the ultraviolet range (UV absorbers, optical brighteners) exhibit improved resistance against chemicals and solvents when bearing perfluoroalkyl substituents.

In addition, chromophores with perfluoroalkyl substituents are also of interest for cosmetic applications e.g. for lipsticks. They show higher resistance against aqueous as well as lipophilic media. UV absorbers with perfluoroalkyl substituents are of special interest for cosmetic applications like e.g. for sun cream ("day-long" effect).

Accordingly, the present invention is also directed to the use of compounds of the formula $Ch-[(L)_y-(R_f)]_x(X)$, especially the metal dithiolene complexes of formula I according to any of claims 1 to 6, for security printing, especially security printing of bank notes, wherein Ch is a chromophore,
x is an integer 1 to 20;
y is 0, or 1;
L is —O—, —S—, —NH—, —NR$_f$—, —SO$_2$—, —SO$_2$NH—, —SO$_2$NR$_f$—, —C(=O)—, —C(=O)O—, —C(=O)NH—, —NHC(=O)—, —C(=O)NR$_f$—, —OC(=O)O—, —OC(=O)NH—,

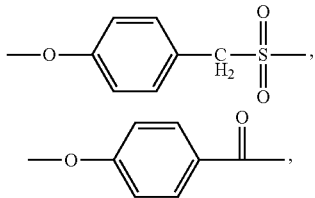

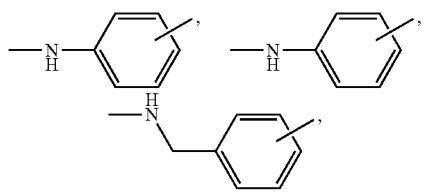

—O—(CH$_2$)$_p$—OC(=O)O—, —(CH$_2$)$_p$—OC(=O)NR$_f$—, —N—[(CH$_2$)$_p$—OC(=O)O]$_2$—,

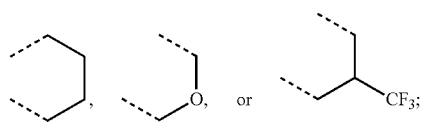

or —OC(=O)NR$_f$—,
p is an integer of 1 to 4,
R$_f$ is a group —(CHR$^5$)$_n$—(CR$^6$F)$_m$—Z,
wherein the group R$_f$ may be interrupted by one, or more groups —O—, —NR$^8$—, —S—, —C(=O)—, —C(=O)O—, —C(=O)NR$^8$—, —S(=O)—, or —SO$_2$—;
Z is H, halogen, such as, for example, F, Cl, or Br, or

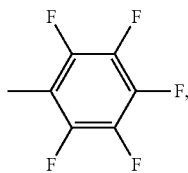

R$^5$ is H, CF$_3$, CH$_3$, or

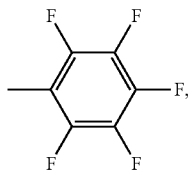

R$^6$ is F, CF$_3$, H, Cl, or Br,
groups —(CR$^6$F)— may be interrupted by CR$^9$H;
two groups R$^5$ together may form a double bond, or a group

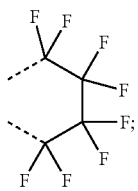

two groups R$^6$ together may form a double bond,
R$^5$ and R$^6$ together may form a double bond;
R$^6$ and Z together may form a double bond, or a group

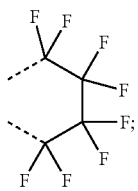

R$^9$ and R$^6$ together may form a double bond;
if two, or more groups R$^5$ are present within a group R$_f$, they can be the same, or different;
if two, or more groups R$^6$ are present within a group R$_f$, they can be the same, or different;
R$^8$ is H, or
R$^9$ is H;
m+n is an integer of 2 to 22,
n is 0, or an integer 1 to 7, and
m is an integer 2 to 15.

Preferred are compounds of formula X, wherein x is an integer 1 to 16; y is 0, or 1; L is —O—, —S—, —NH—, —SO$_2$NH—, or —C(=O)NH, especially —O—, —S—, —NH—, or —SO$_2$NH—.

The present invention is directed to chromophores (absorbing electromagnetic radiation in the ultraviolet, visible and infrared range of the spectrum from 300 nm to 1500 nm) with perfluoro alkyl chains in general for printing applications. Chromophores can be e.g. from the following classes:

Polymethine and their aza analogs like cyanine, merocyanine, styryl, croconaine and squaraine, naphtholactams;

Di- and triarylmethane and their aza analogs incl. phenazine, oxazine, thiazine, dioxazine, xanthene and fluorane;

Phthalocyanine and naphthalocyanine;

Azo and azo metalcomplexes;

Carbonyl chromophores like anthraquinone, indigoid, rylene, coumarine, benzodifuranone and vat dyes;

Dithiolenes;

Quinone-diimmonium salts;

Stilbenes;

UV-absorbers, especially heterocyclic UV-absorbers; and

Optical brighteners.

The chromophores Ch can have from 1 to 20 perfluoro alkyl groups R$_f$. Preferences for the groups R$_f$ have been explained above with respect to metal complexes of formula I:

R$_f$ is preferably a group —(CH$_2$)$_n$—(CF$_2$)$_m$—Z, wherein Z is H, F, Cl, or Br, m+n is an integer of 2 to 22, n is 0, or an integer of 1 to 7, and m is an integer 2 to 15.

R$_f$ is more preferably a group —(CH$_2$)$_n$—(CF$_2$)$_m$—F, wherein m+n is an integer of 2 to 12, n is 0, or an integer of 1 to 5, and m is an integer of 2 to 12, especially m+n is an integer of 3 to 12, n is 0, 1, or 2, and m is an integer of 3 to 10.

Most preferred, R$_f$ is a group —(CH$_2$)$_n$—(CF$_2$)$_m$—F, wherein
n is an integer 1, or 2,
m is an integer 3 to 8, especially 3 to 5, and
m+n is an integer 4 to 10, especially 4 to 7.

The following structures are given for illustration:
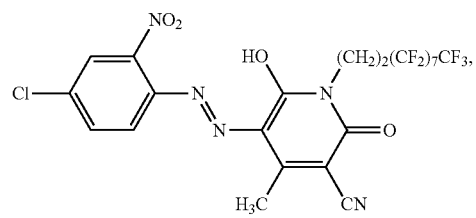
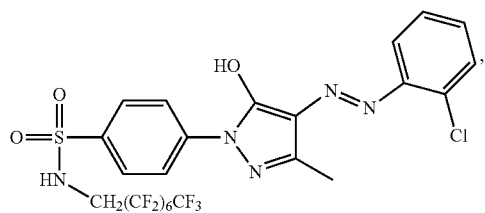
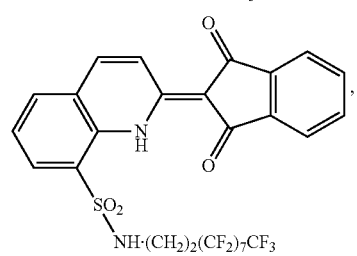
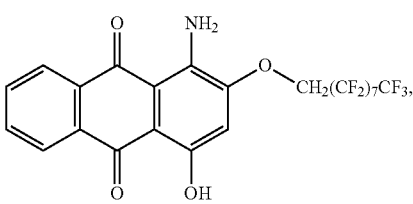
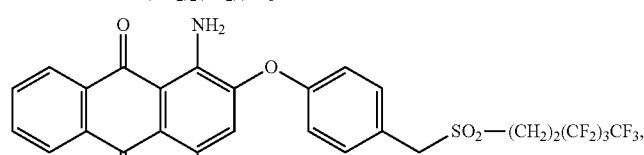
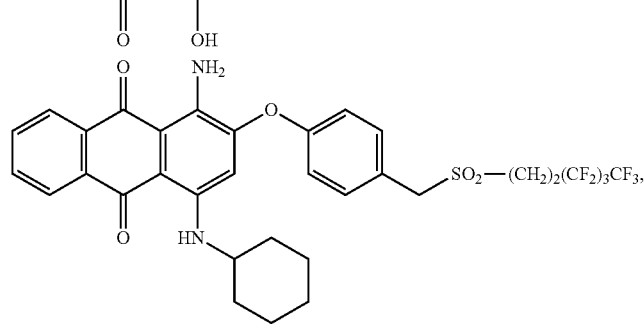
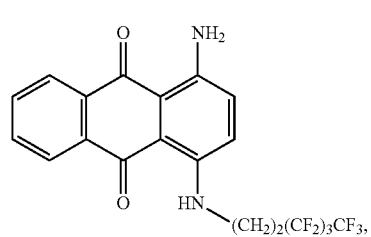
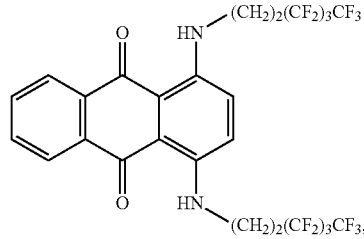
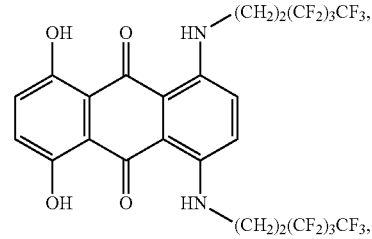
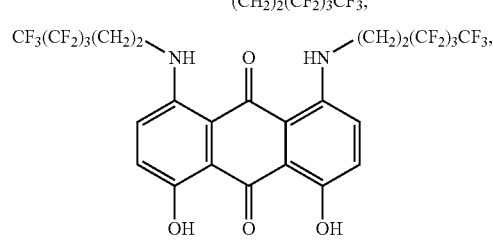
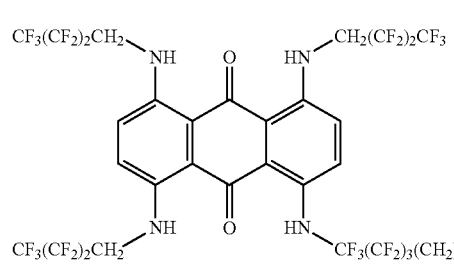
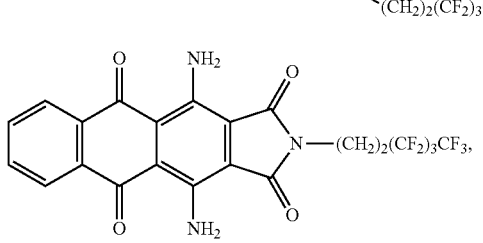

-continued
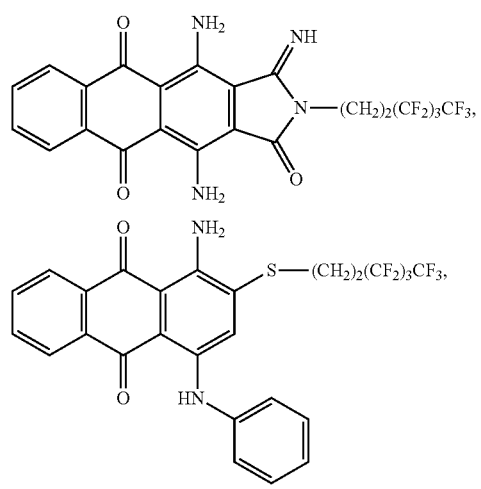
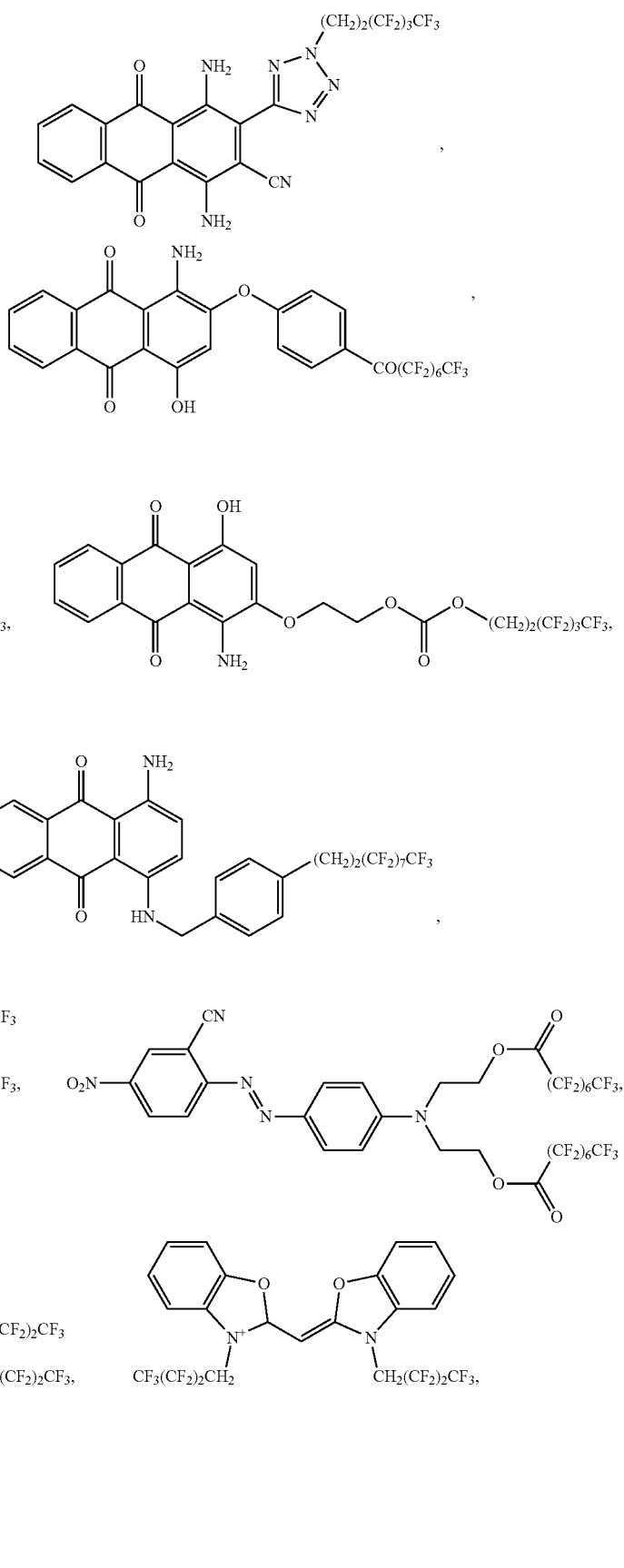

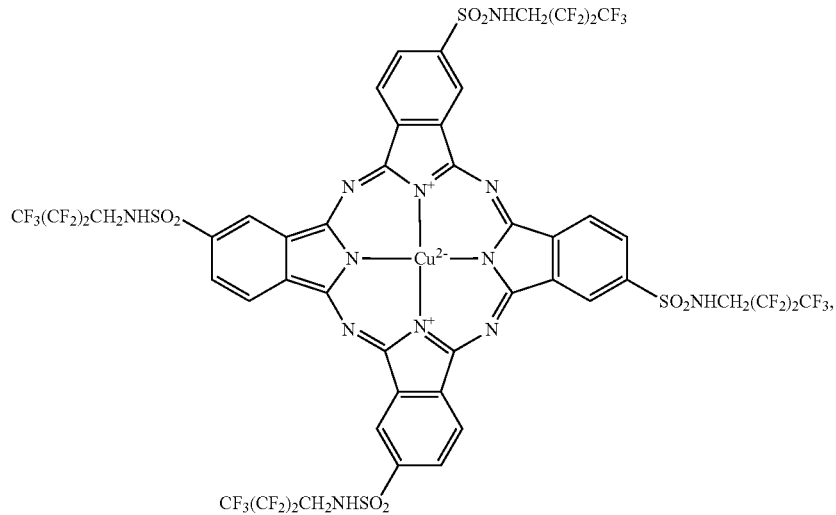
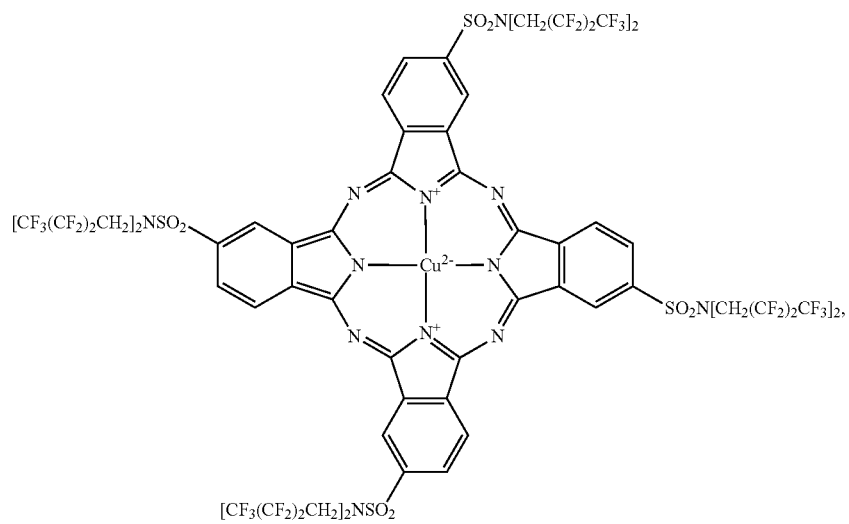
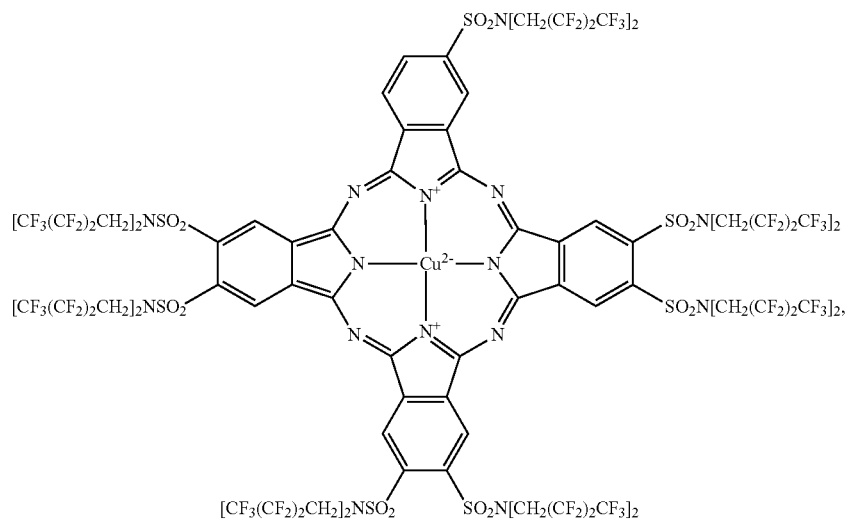

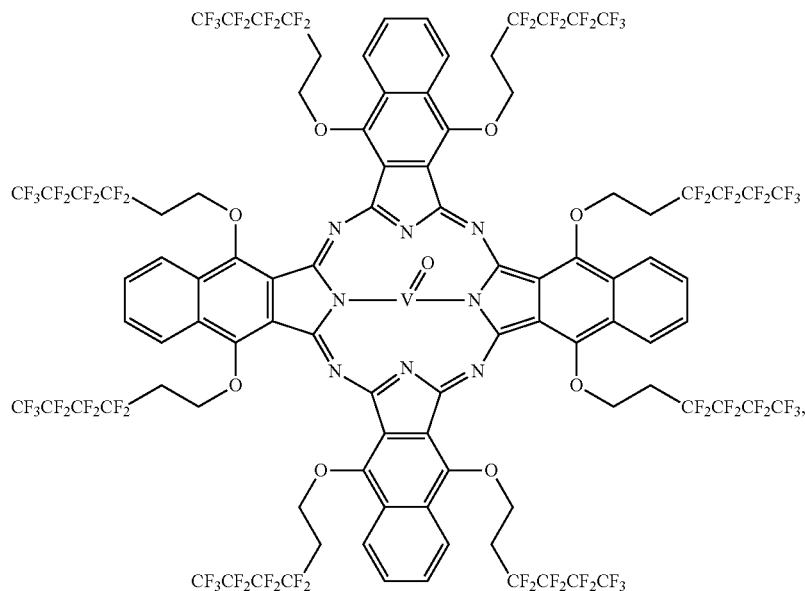
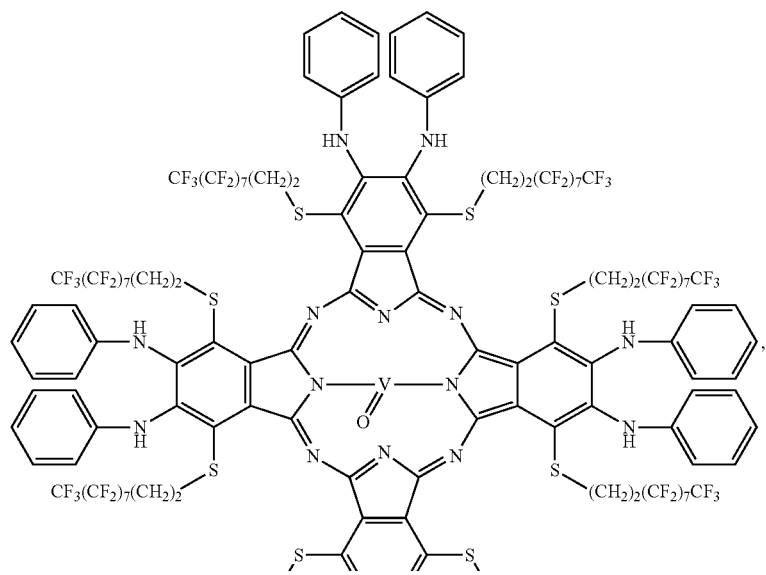
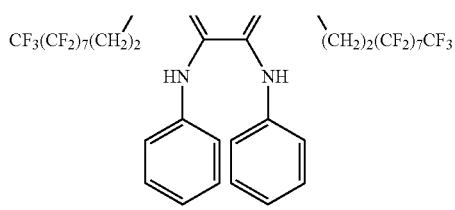

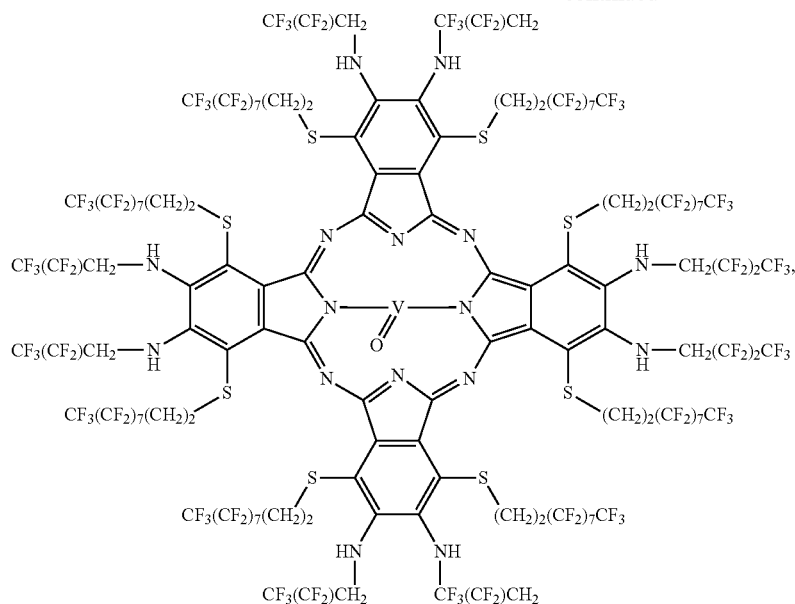
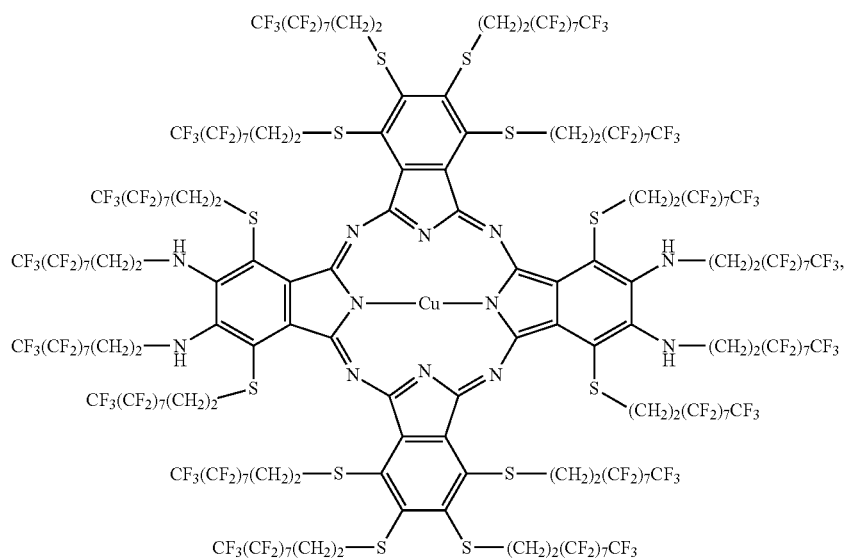
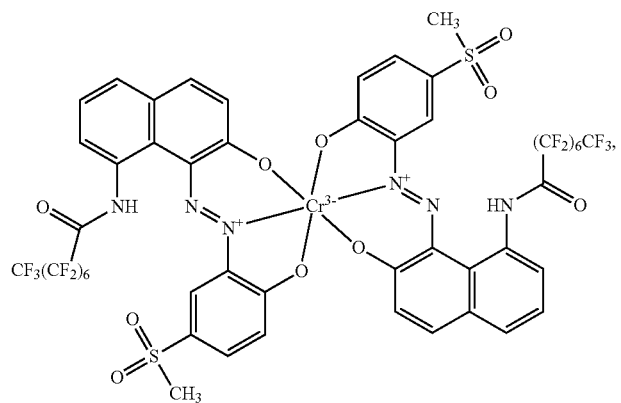

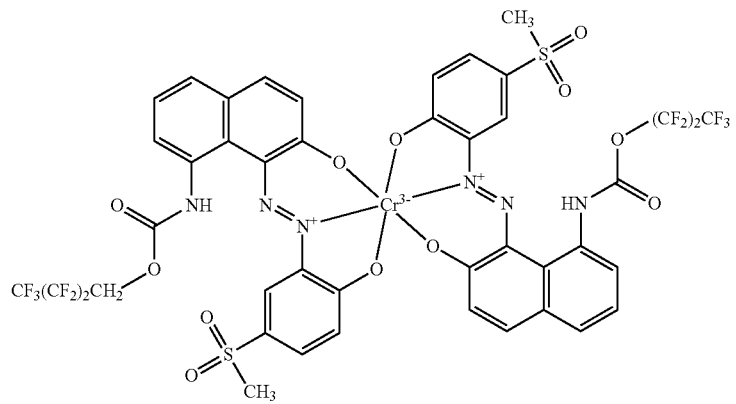
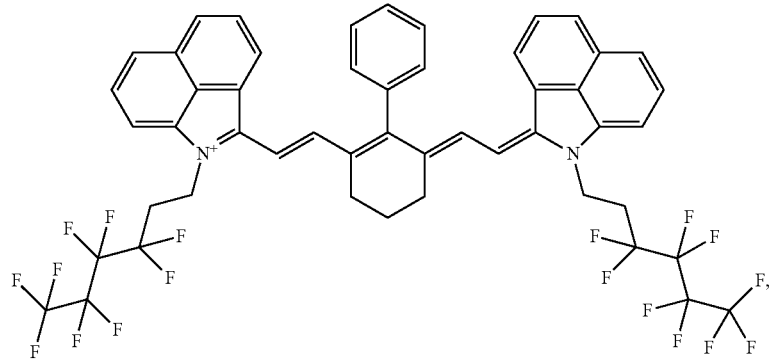
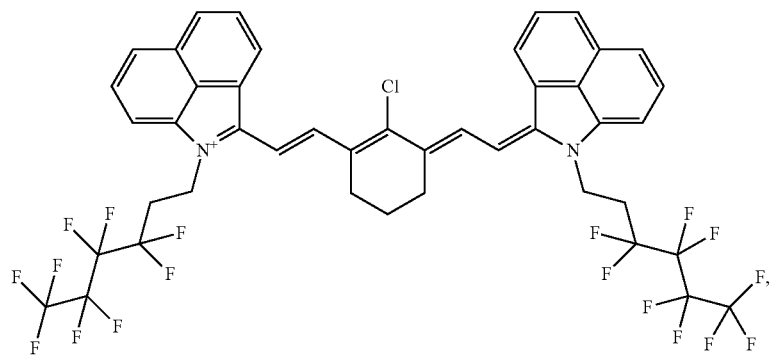
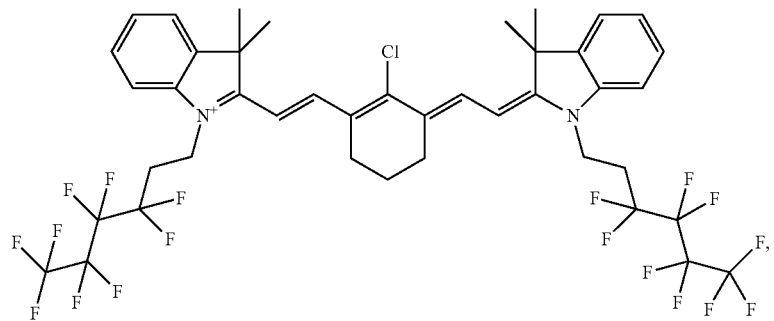

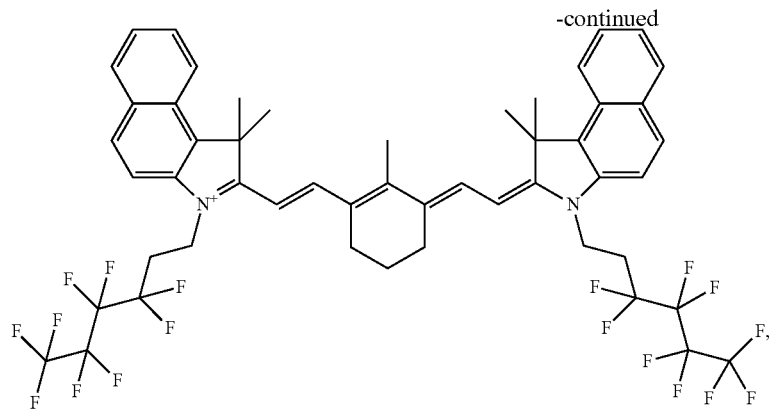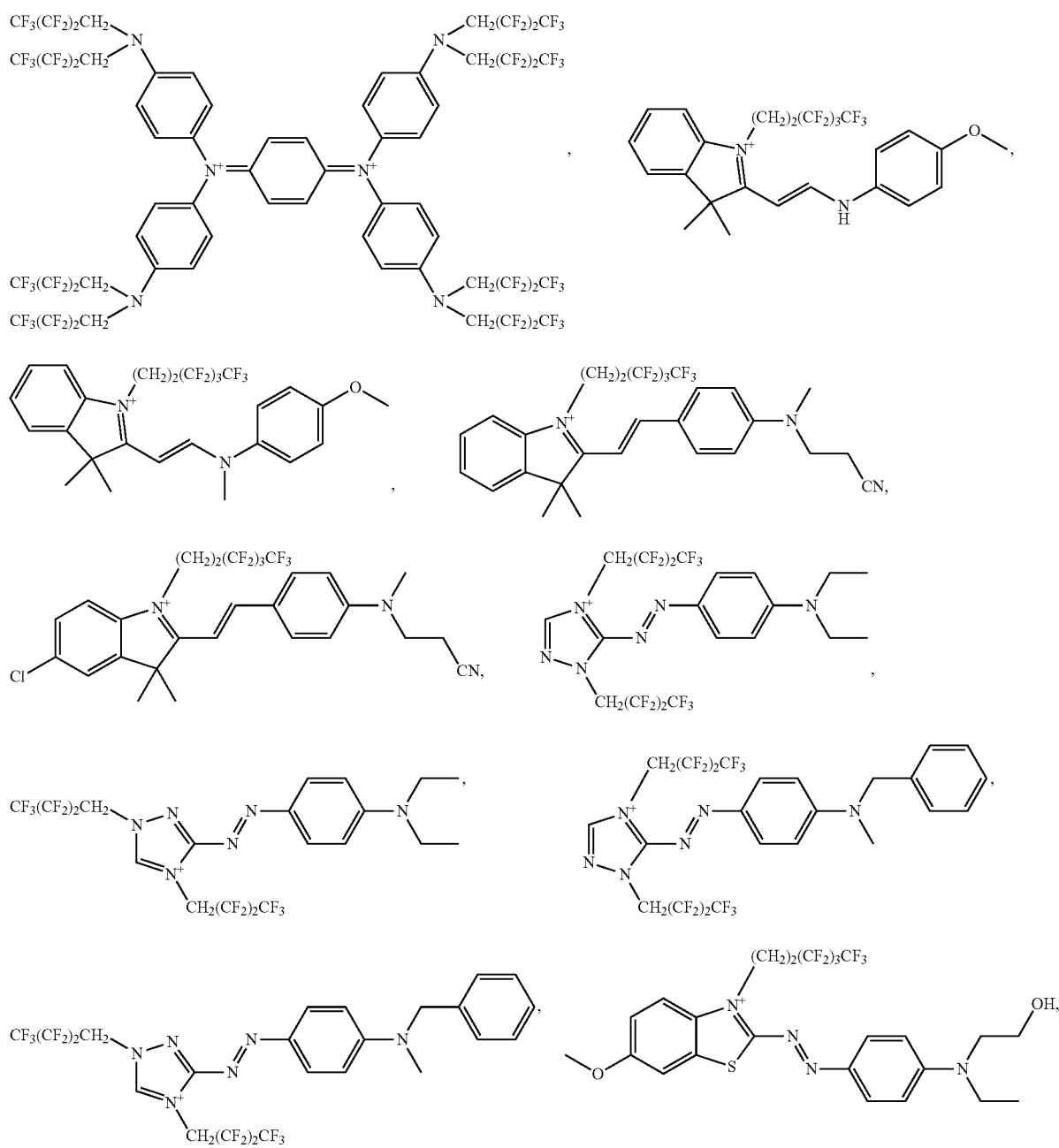

41
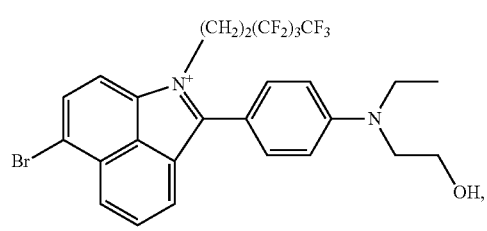
-continued
42
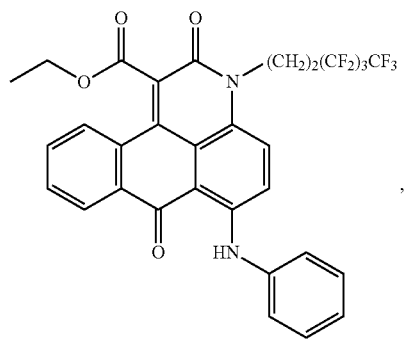
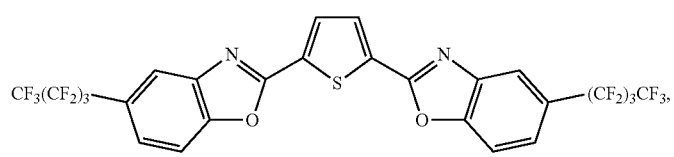
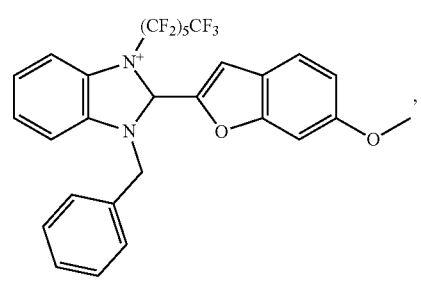
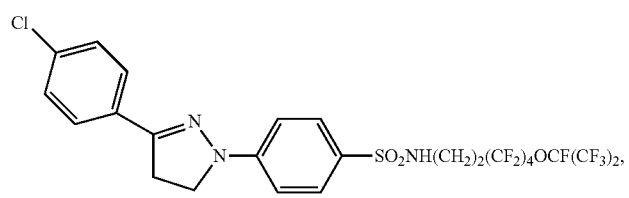
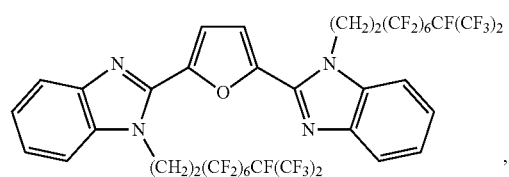
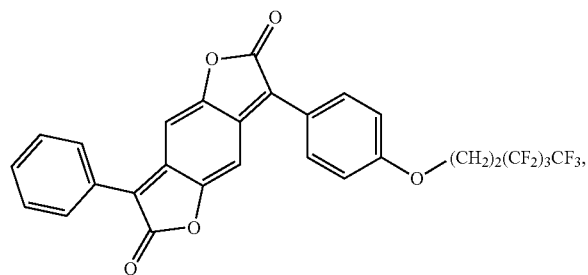
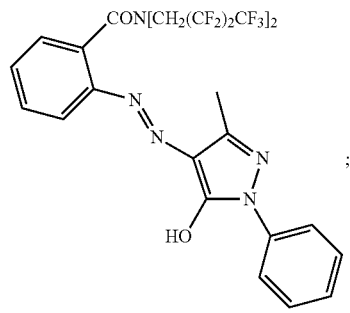
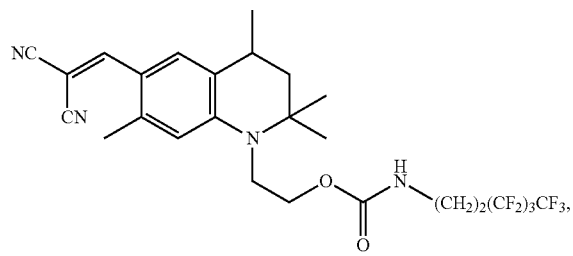
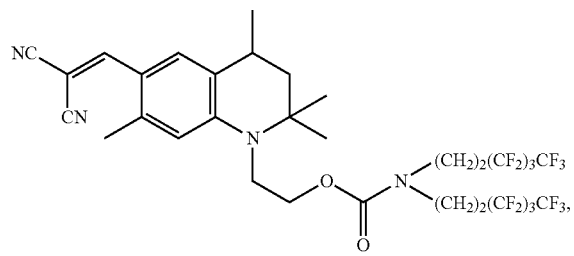
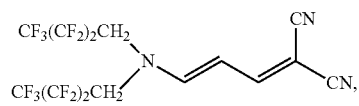
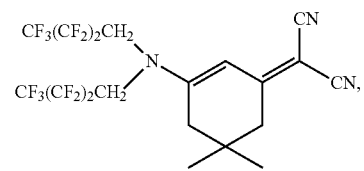
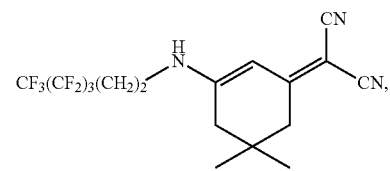

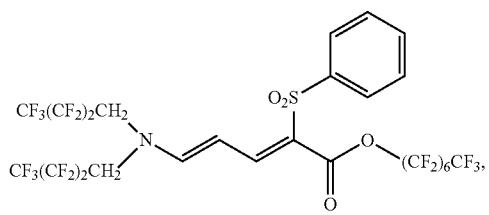

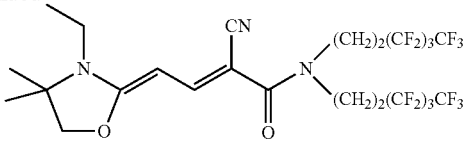

Advantageously, the compounds of the formula X, especially the metal dithiolene complexes of formula I according to any of claims 1 to 6, may be used in a printing ink formulation for security printing to improve the fastness properties of the obtained print, in particular to improve the fastness to chemicals, solvents and/or boiling water.

In security printing, the compound of formula X, especially the metal dithiolene complex of formula I, is added to a printing ink formulation. Suitable printing inks are water-based, oil-based or solvent-based printing inks, based on pigment or dye, for inkjet printing, flexographic printing, screen printing, intaglio printing, offset printing, laser printing or letterpress printing and for use in electrophotography. Printing inks for these printing processes usually comprise solvents, binders, and also various additives, such as plasticizers, antistatic agents or waxes. Printing inks for offset printing and letterpress printing are usually formulated as high-viscosity paste printing inks, whereas printing inks for flexographic printing and intaglio printing are usually formulated as liquid printing inks with comparatively low viscosity.

In the context of the present invention, the expression "printing ink" also encompasses formulations that in addition to at least one IR absorber of the general formula I comprise a colorant. The expression "printing ink" also encompasses printing lacquers that comprise no colorant.

The printing ink formulation for security printing according to the invention preferably comprises
  a) at least one compound of the formula X as defined in claim 7, especially at least one metal dithiolene complex of the general formula I as defined in any of claims 1 to 6,
  b) a polymeric binder,
  c) a solvent,
  d) optionally at least one colorant, and
  e) optionally at least one further additive.

Suitable components of printing inks are conventional and are well known to those skilled in the art. Examples of such components are described in "Printing Ink Manual", fourth edition, Leach R. H. et al. (eds.), Van Nostrand Reinhold, Wokingham, (1988). Details of printing inks and their formulation are also disclosed in "Printing Inks"—Ullmann's Encyclopedia of Industrial Chemistry, Sixth Edition, 1999 Electronic Release. A formulation of an IR-absorbing intaglio ink formulation is described in US 20080241492 A1. The disclosure of the afore-mentioned documents is incorporated herein by reference.

The printing ink formulation according to the invention contains in general from 0.0001 to 25% by weight, preferably from 0.001 to 15% by weight, in particular from 0.01 to 5% by weight, based on the total weight of the printing ink formulation, of component a).

The compounds of formula X, especially the metal dithiolene complex of formula I, are present in the printing ink formulation in dissolved form or in solid form (in a finely divided state).

The printing ink formulation according to the invention contains in general from 5 to 74% by weight, preferably from 10 to 60% by weight, more preferably from 15 to 40% by weight, based on the total weight of the printing ink formulation, of component b).

Suitable polymeric binders b) for the printing ink formulation according to the invention are for example selected from natural resins, phenol resin, phenol-modified resins, alkyd resins, polystyrene homo- and copolymers, terpene resins, silicone resins, polyurethane resins, urea-formaldehyde resins, melamine resins, polyamide resins, polyacrylates, polymethacrylates, chlorinated rubber, vinyl ester resins, acrylic resins, epoxy resins, nitrocellulose, hydrocarbon resins, cellulose acetate, and mixtures thereof.

The printing ink formulation according to the invention can also comprise components that form a polymeric binder by a curing process. Thus, the printing ink formulation according to the invention can also be formulated to be energy-curable, e.g. able to be cured by UV light or EB (electron beam) radiation. In this embodiment, the binder comprises one or more curable monomers and/oligomers. Corresponding formulations are known in the art and can be found in standard textbooks such as the series "Chemistry & Technology of UV & EB Formulation for Coatings, Inks & Paints", published in 7 volumes in 1997-1998 by John Wiley & Sons in association with SITA Technology Limited.

Suitable monomers and oligomers (also referred to as prepolymers) include epoxy acrylates, acrylated oils, urethane acrylates, polyester acrylates, silicone acrylates, acrylated amines, and acrylic saturated resins. Further details and examples are given in "Chemistry & Technology of UV & EB Formulation for Coatings, Inks & Paints", Volume II: Prepolymers & Reactive Diluents, edited by G Webster.

If a curable polymeric binder is employed, it may contain reactive diluents, i.e. monomers which act as a solvent and which upon curing are incorporated into the polymeric binder. Reactive monomers are typically chosen from acrylates or methacrylates, and can be monofunctional or multifunctional. Examples of multifunctional monomers include polyester acrylates or methacrylates, polyol acrylates or methacrylates, and polyether acrylates or methacrylates.

In the case of printing ink formulations to be cured by UV radiation, it is usually necessary to include at least one photoinitiator to initiate the curing reaction of the monomers upon exposure to UV radiation. Examples of useful photoinitiators can be found in standard textbooks such as "Chemistry & Technology of UV & EB Formulation for Coatings, Inks & Paints", Volume III, "Photoinitiators for Free Radical Cationic and Anionic Polymerisation", 2nd edition, by J. V. Crivello & K. Dietliker, edited by G. Bradley and published in 1998 by John Wiley & Sons in association with SITA Technology Limited. It may also be advantageous to include a sensitizer in conjunction with the photoinitiator in order to achieve efficient curing.

The printing ink formulation according to the invention contains in general from 1 to 94.9999% by weight, preferably from 5 to 90% by weight, in particular from 10 to 85% by weight, based on the total weight of the printing ink formulation, of a solvent c).

Suitable solvents are selected from water, organic solvents and mixtures thereof. For the purpose of the invention, reactive monomers which also act as solvents are regarded as part of the afore-mentioned binder component b).

Examples of solvents comprise water; alcohols, e.g. ethanol, 1-propanol, 2-propanol, ethylene glycol, propylene glycol, diethylene glycol and ethoxy propanol; esters, e.g. ethyl acetate, isopropyl acetate, n-propyl acetate and n-butyl acetate; hydrocarbons, e.g. toluene, xylene, mineral oils and vegetable oils, and mixtures thereof.

The printing ink formulation according to the invention may contain an additional colorant d). Preferably, the printing ink formulation contains from 0 to 25% by weight, more preferably from 0.1 to 20% by weight, in particular from 1 to 15% by weight, based on the total weight of the printing ink formulation, of a colorant d).

Suitable colorants d) are selected conventional dyes and in particular conventional pigments. The term "pigment" is used in the context of this invention comprehensively to identify all pigments and fillers, examples being colour pigments, white pigments, and inorganic fillers. These include inorganic white pigments, such as titanium dioxide, preferably in the rutile form, barium sulfate, zinc oxide, zinc sulfide, basic lead carbonate, antimony trioxide, lithopones (zinc sulfide+barium sulfate), or coloured pigments, examples being iron oxides, carbon black, graphite, zinc yellow, zinc green, ultramarine, manganese black, antimony black, manganese violet, Paris blue or Schweinfurt green. Besides the inorganic pigments the printing ink formulation of the invention may also comprise organic colour pigments, examples being sepia, gamboge, Cassel brown, toluidine red, para red, Hansa yellow, indigo, azo dyes, anthraquinonoid and indigoid dyes, and also dioxazine, quinacridone, phthalocyanine, isoindolinone, and metal complex pigments. Also suitable are synthetic white pigments with air inclusions to increase the light scattering, such as the Rhopaque® dispersions. Suitable fillers are, for example, aluminosilicates, such as feldspars, silicates, such as kaolin, talc, mica, magnesite, alkaline earth metal carbonates, such as calcium carbonate, in the form for example of calcite or chalk, magnesium carbonate, dolomite, alkaline earth metal sulfates, such as calcium sulfate, silicon dioxide, etc.

The printing ink formulation according to the invention may contain at least one additive e). Preferably, the printing ink formulation contains from 0 to 25% by weight, more preferably from 0.1 to 20% by weight, in particular from 1 to 15% by weight, based on the total weight of the printing ink formulation, of at least one component e).

Suitable additives (component e)) are selected from plasticizers, waxes, siccatives, antistatic agents, chelators, antioxidants, stabilizers, adhesion promoters, surfactants, flow control agents, defoamers, biocides, thickeners, etc. and combinations thereof. These additives serve in particular for fine adjustment of the application-related properties of the printing ink, examples being adhesion, abrasion resistance, drying rate, or slip.

In particular, the printing ink formulation for security printing according to the invention preferably contains
a) 0.0001 to 25% by weight of at least one compound of the formula X as defined in claim 7, especially at least one metal dithiolene complex of the general formula I as defined in any of claims 1 to 6, b) 5 to 74% by weight of at least one polymeric binder,
c) 1 to 94.9999% by weight of at least one a solvent,
d) 0 to 25% by weight of at least one colorant, and
e) 0 to 25% by weight of at least one further additive,
wherein the sum of components a) to e) adds up to 100%.

The printing ink formulations according to the invention are advantageously prepared in a conventional manner, for example by mixing the individual components. As mentioned earlier, the compound of formula X, especially the dithiolene complex of formula I is present in the printing ink formulations in a dissolved or finely divided solid form. Additional colorants may be employed in the printing ink formulation of the invention or in a separate ink formulation. When additional colorants are to be employed in a separate formulation, the time of application of the printing ink formulation according to the invention is usually immaterial. The printing ink formulation according to the invention can for example be applied first and then be overprinted with conventional printing inks. But it is also possible to reverse this sequence or, alternatively, to apply the printing ink formulation according to the invention in a mixture with conventional printing inks. In every case the prints are readable with suitable light sources.

Primers can be applied prior to the printing ink formulation according to the invention. By way of example, the primers are applied in order to improve adhesion to the substrate. It is also possible to apply additional printing lacquers, e.g. in the form of a covering to protect the printed image. Additional printing lacquers may also be applied to serve aesthetic purposes, or serve to control application-related properties. By way of example, suitably formulated additional printing lacquers can be used to influence the roughness of the surface of the substrate, the electrical properties, or the water-vapour-condensation properties. Printing lacquers are usually applied in-line by means of a lacquering system on the printing machine employed for printing the printing ink formulation according to the invention.

The printing ink formulations according to the invention are also suitable for use in multilayer materials. Multilayer materials are e.g. composed of two or more plastics foils, such as polyolefin foils, metal foils, or metallised plastics foils, which are bonded to one another, by way of example, via lamination or with the aid of suitable laminating adhesives. These composites may also comprise other functional layers, such as odour-barrier layers or water-vapour barriers.

Chromophores with perfluoroalkyl substituents are also of interest for cosmetic applications e.g. for lipsticks. They show higher resistance against aqueous as well as lipophilic media. UV absorbers with perfluoroalkyl substituents are of special interest for cosmetic applications like e.g. for sun cream ("day-long" effect).

Accordingly, the present invention is also directed to cosmetic preparations or formulations, comprising UV absorbers of the formula X as defined above, such as, for example

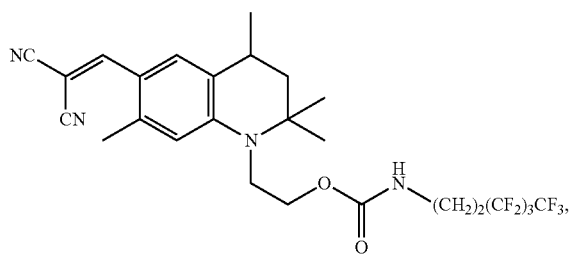

-continued

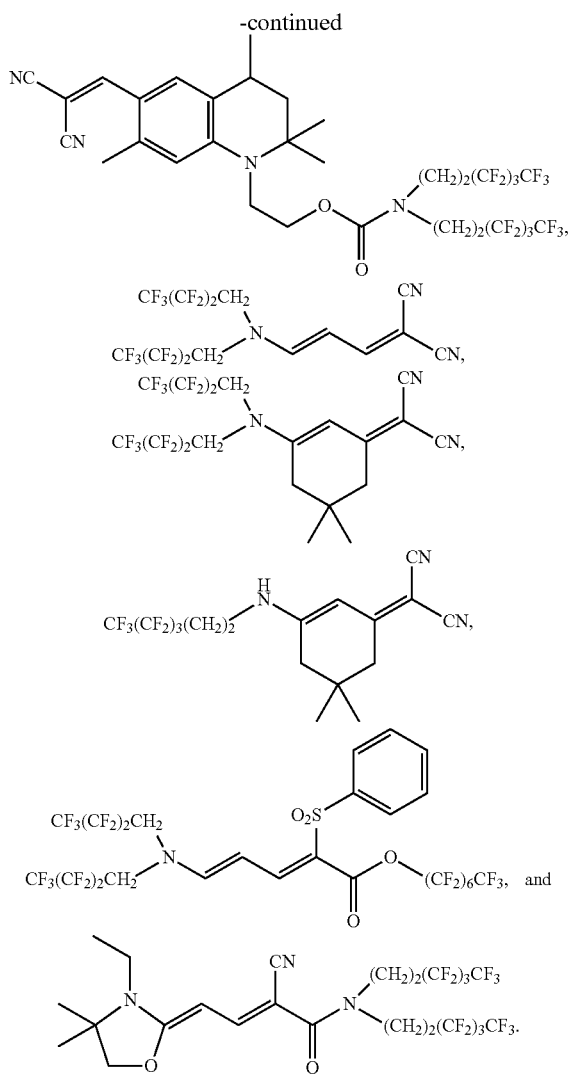

The cosmetic preparation or formulation comprises from 0.0001 to 90% by weight of a compound of the formula X and from 10 to 99.9999% of a cosmetically suitable carrier material, based on the total weight of the cosmetic preparation or formulation.

The cosmetic preparations and formulations according to the invention preferably contain the compound of the formula X in an amount from 0.005 to 50% by weight, based on the total weight of the preparation.

Suitable carrier materials for the cosmetic preparations and formulations according to the invention include the customary materials used in such compositions.

The cosmetic preparations and formulations according to the invention may be in the form of, for example, sticks, ointments, creams, emulsions, suspensions, dispersions, powders or solutions. They are, for example, lipsticks, mascara preparations, blushers, eye-shadows, foundations, eyeliners, powder or nail varnishes.

If the preparations are in the form of sticks, for example lipsticks, eye-shadows, blushers or foundations, the preparations consist for a considerable part of fatty components, which may consist of one or more waxes, for example ozokerite, lanolin, lanolin alcohol, hydrogenated lanolin, acetylated lanolin, lanolin wax, beeswax, candelilla wax, microcrystalline wax, carnauba wax, cetyl alcohol, stearyl alcohol, cocoa butter, lanolin fatty acids, petrolatum, petroleum jelly, mono-, di- or tri-glycerides or fatty esters thereof that are solid at 25° C., silicone waxes, such as methyloctadecaneoxypolysiloxane and poly(dimethylsiloxy)stearoxysiloxane, stearic acid monoethanolamine, colophane and derivatives thereof, such as glycol abietates and glycerol abietates, hydrogenated oils that are solid at 25° C., sugar glycerides and oleates, myristates, lanolates, stearates and dihydroxystearates of calcium, magnesium, zirconium and aluminium.

The fatty component may also consist of a mixture of at least one wax and at least one oil, in which case the following oils, for example, are suitable: paraffin oil, purcelline oil, perhydrosqualene, sweet almond oil, avocado oil, calophyllum oil, castor oil, sesame oil, jojoba oil, mineral oils having a boiling point of about from 310 to 410° C., silicone oils, such as dimethylpolysiloxane, linoleyl alcohol, linolenyl alcohol, oleyl alcohol, cereal grain oils, such as wheatgerm oil, isopropyl lanolate, isopropyl palmitate, isopropyl myristate, butyl myristate, cetyl myristate, hexadecyl stearate, butyl stearate, decyl oleate, acetyl glycerides, octanoates and decanoates of alcohols and polyalcohols, for example of glycol and glycerol, ricinoleates of alcohols and polyalcohols, for example of cetyl alcohol, isostearyl alcohol, isocetyl lanolate, isopropyl adipate, hexyl laurate and octyl dodecanol.

The fatty components in such preparations in the form of sticks may generally constitute up to 99.91% by weight of the total weight of the preparation.

The cosmetic preparations and formulations according to the invention may additionally comprise further constituents, such as, for example, glycols, polyethylene glycols, polypropylene glycols, monoalkanolamides, non-coloured polymeric, inorganic or organic fillers, preservatives, UV filters or other adjuvants and additives customary in cosmetics, for example a natural or synthetic or partially synthetic di- or tri-glyceride, a mineral oil, a silicone oil, a wax, a fatty alcohol, a Guerbet alcohol or ester thereof, a lipophilic functional cosmetic active ingredient, including sun-protection filters, or a mixture of such substances.

The preparations in stick form are preferably anhydrous but may in certain cases comprise a certain amount of water which, however, in general does not exceed 40% by weight, based on the total weight of the cosmetic preparation.

If the cosmetic preparations and formulations according to the invention are in the form of semi-solid products, that is to say in the form of ointments or creams, they may likewise be anhydrous or aqueous. Such preparations and formulations are, for example, mascaras, eyeliners, foundations, blushers, eye-shadows, or compositions for treating rings under the eyes.

If, on the other hand, such ointments or creams are aqueous, they are especially emulsions of the water-in-oil type or of the oil-in-water type that comprise, apart from the pigment, from 1 to 98.8% by weight of the fatty phase, from 1 to 98.8% by weight of the aqueous phase and from 0.2 to 30% by weight of an emulsifier.

Such ointments and creams may also comprise further conventional additives, such as, for example, perfumes, antioxidants, preservatives, gel-forming agents, UV filters, colorants, pigments, pearlescent agents, non-coloured polymers as well as inorganic or organic fillers. If the preparations are in the form of a powder, they consist substantially of a mineral or inorganic or organic filler such as, for example, talcum, kaolin, starch, polyethylene powder or polyamide powder, as well as adjuvants such as binders, colorants etc.

Such preparations may likewise comprise various adjuvants conventionally employed in cosmetics, such as fragrances, antioxidants, preservatives etc.

If the cosmetic preparations and formulations according to the invention are nail varnishes, they consist essentially of nitrocellulose and a natural or synthetic polymer in the form of a solution in a solvent system, it being possible for the solution to comprise other adjuvants, for example pearlescent agents.

In that embodiment, the coloured polymer is present in an amount of approximately from 0.1 to 5% by weight.

The cosmetic preparations and formulations according to the invention are prepared in conventional manner, for example by mixing or stirring the components together, optionally with heating so that the mixtures melt.

UV absorbers of formula X are particularly suitable as UV filters, i.e. for protecting ultraviolet-sensitive organic materials, in particular the skin and hair of humans and animals, from the harmful effects of UV radiation. These compounds are therefore suitable as sunscreens in cosmetic, pharmaceutical and veterinary medical preparations. These compounds can be used both in dissolved form and in the micronized state.

Besides the UV absorbers according to the invention, the cosmetic compositions can additionally contain one or more further UV-protective substances, e.g. triazines, oxanilides, triazoles or amides containing vinyl groups or cinnamides. Such protective substances are described, for example, in GB-A-2,286,774 or alternatively are known from Cosmetics & Toiletries (107), 50 et seq. (1992).

The cosmetic preparations or formulations contain 0.1 to 15, preferably 0.5 to 10% by weight, based on the total weight of the composition, of a UV absorber or of a mixture of UV absorbers and a cosmetically compatible auxiliary.

The cosmetic preparations or formulations can be prepared by physical mixing of the UV absorber(s) with the auxiliary by the usual methods, such as, for example, by simply stirring the individual components together.

The cosmetic preparations or formulations can be formulated as a water-in-oil or oil-in-water emulsion, as an oil-in-alcohol lotion, as a vesicular dispersion of an ionic or nonionic amphiphilic lipid, as a gel, solid stick or as an aerosol formulation.

As a water-in-oil or oil-in-water emulsion, the cosmetically compatible auxiliary preferably contains 5 to 50% of an oil phase, 5 to 20% of an emulsifier and 30 to 90% of water. The oil phase can in this case contain any oil suitable for cosmetic formulations, e.g. one or more hydrocarbon oils, a wax, a natural oil, a silicone oil, a fatty acid ester or a fatty alcohol. Preferred mono- or polyols are ethanol, isopropanol, propylene glycol, hexylene glycol, glycerol and sorbitol.

Any emulsifier which can be employed conventionally can be used for the cosmetic preparations or formulations, e.g. one or more ethoxylated esters of natural derivatives, e.g. polyethoxylated esters of hydrogenated castor oil; or a silicone emulsifier such as silicone polyol; a free or ethoxylated fatty acid soap; an ethoxylated fatty alcohol; a free or ethoxylated sorbitan ester, an ethoxylated fatty acid; or an ethoxylated glyceride.

The cosmetic preparations or formulations can also contain further components such as emollients, emulsion stabilizers, skin moisturizers, skin bronzing accelerators, thickeners such as xanthan, moisture retention agents such as glycerol, preservatives, fragrances and colourants.

Various features and aspects of the present invention are illustrated further in the examples that follow. While these examples are presented to show one skilled in the art how to operate within the scope of this invention, they are not to serve as a limitation on the scope of the invention where such scope is only defined in the claims. Unless otherwise indicated in the following examples and elsewhere in the specification and claims, all parts and percentages are by weight, temperatures are in degrees centigrade and pressures are at or near atmospheric.

EXAMPLES

Example 1 a) 21.47 parts 3,3,4,4,5,5,6,6,6-nonafluoro-hexyl-1-amine are heated to 110° C. and 3.06 parts carbondisulfide are slowly added under stirring within 15 minutes. After stirring for further 90 minutes the reaction mass is poured into a beaker. The solidified product is crunched, dried in vacuo at 40° C. for 2 hours and dissolved in 900 parts dichloromethane. To this solution 5.14 parts oxalyl chloride are added at room temperature under stirring. After 60 minutes the solvent is distilled off by a rotary evaporator and the oily residue is dried under stirring in vacuo at 40° C. for 30 minutes. The resulting oil is dissolved in 30 parts 2-propanol and 1000 parts ligroin (boiling point 100-140° C.) are added. Fine yellow needles are formed after standing overnight and cooling to 5° C. The crystals are filtered off, washed with ligroin and dried in vacuo at 40° C. for 1 hour: 16.0 parts compound 1a are obtained.

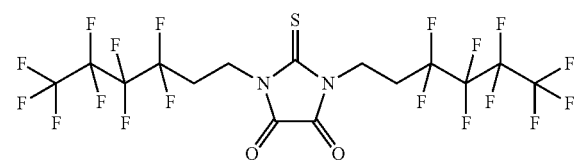

(1a)

b) 8.71 parts compound 1a, 0.41 parts nickel powder and 6.07 Lawesson's reagent are heated in 550 parts chlorobenzene under nitrogen atmosphere and intense stirring to 132° C. After 2 hours at reflux temperature the reaction mixture is cooled to room temperature, the resulting precipitate is filtered off and washed with acetone. After drying 6.80 parts dark crystals are obtained which are recrystallized from boiling chlorobenzene under nitrogen: 6.50 parts nickel dithiolene complex A-1 (absorption maximum: 994 nm; absorbance coefficient: 65,800).

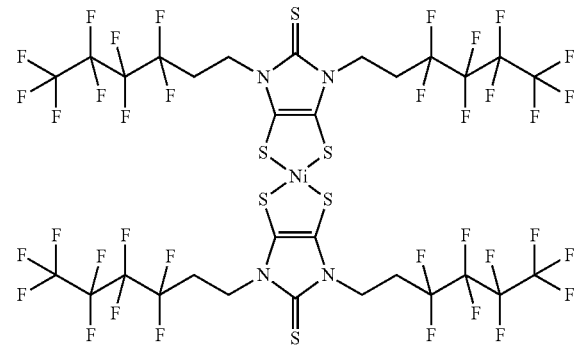

(A-1)

Example 2

By proceeding as described in Example 1b) but using palladium(II) chloride instead of nickel powder palladium dithiolene complex A-2 is obtained (absorption maximum: 1004 nm; absorbance coefficient: 47,500).

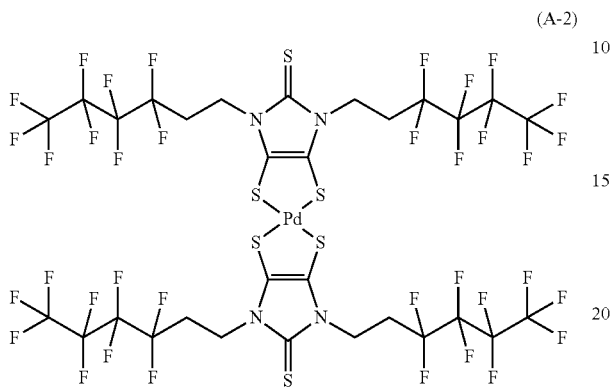
(A-2)

Example 3

By proceeding as described in Example 1b) but using platinum (II) chloride instead of nickel powder platinum dithiolene complex A-3 is obtained.

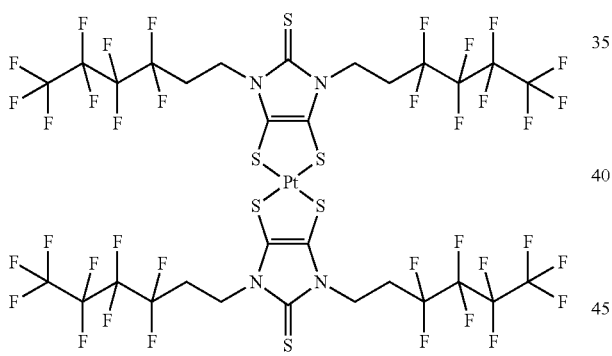
(A-3)

Example 4

By proceeding as described in Example 1a) but using an equimolar amount of 3,3,4,4,5,5,5-heptafluoro-pentyl-1-amine instead of 3,3,4,4,5,5,6,6,6-nonafluoro-hexyl-1-amine and continuing as indicated in Example 1b) nickel dithiolene complex A-4 is obtained.

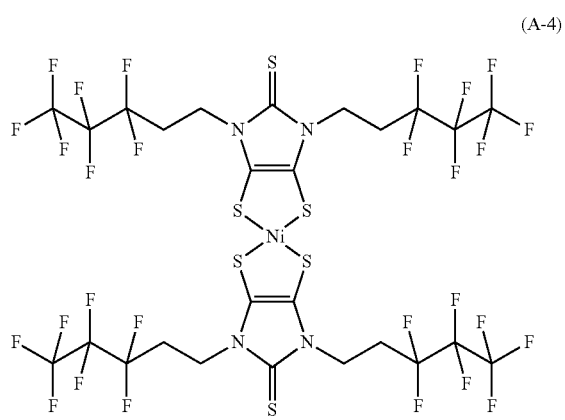
(A-4)

Example 5

By proceeding as described in Example 1a) but using an equimolar amount of 3,3,4,4,5,5,6,6,7,7,8,8,9,9,10,10,10-heptadecafluoro-decyl-1-amine instead of 3,3,4,4,5,5,6,6,6-nonafluoro-hexyl-1-amine and continuing as indicated in Example 1b) nickel dithiolene complex A-5 is obtained.

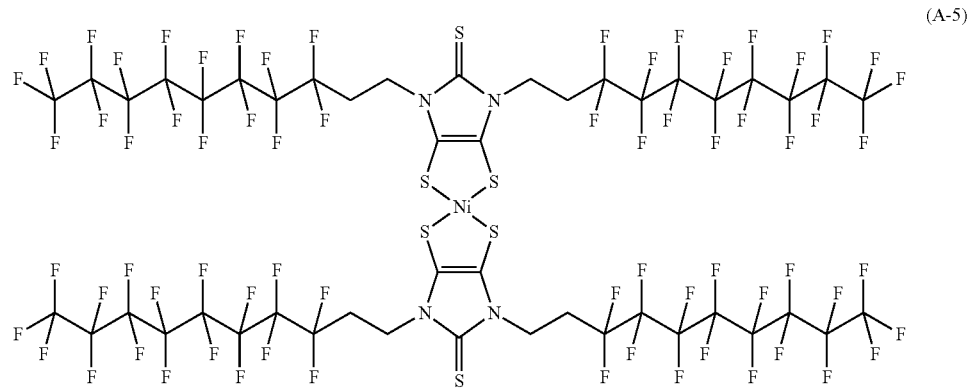
(A-5)

Examples 6 to 10
By proceeding analogously to Example 1a) and 1b) but using the respective fluoroalkyl amines instead of 3,3,4,4,5,5,6,6,6-nonafluoro-hexyl-1-amine the nickel dithiolene complexes A-6, A-7, A-8, A-9 and A-10 are obtained.
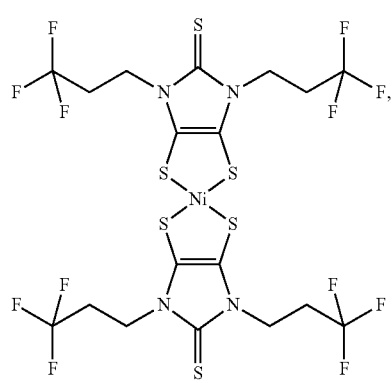
(A-6)
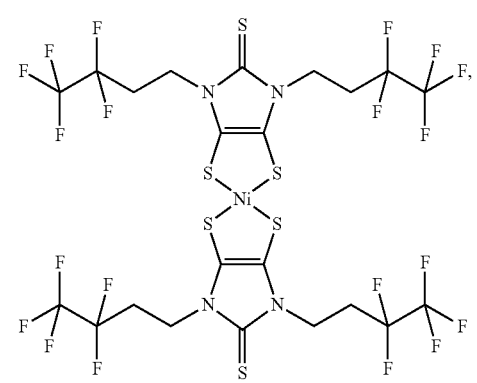
(A-7)
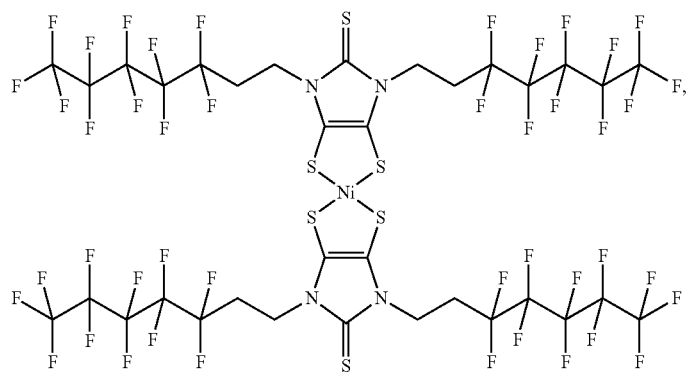
(A-8)
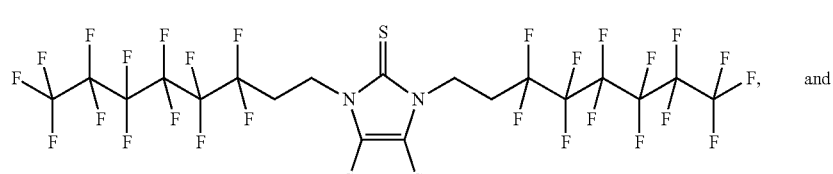
(A-9) and
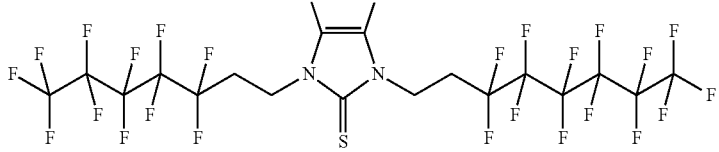
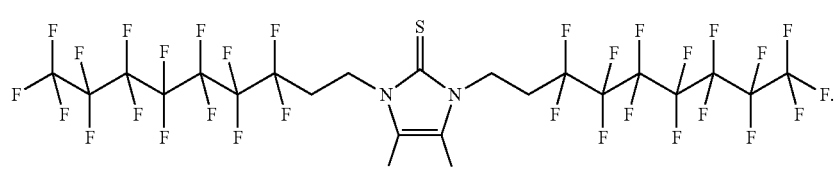
(A-10)
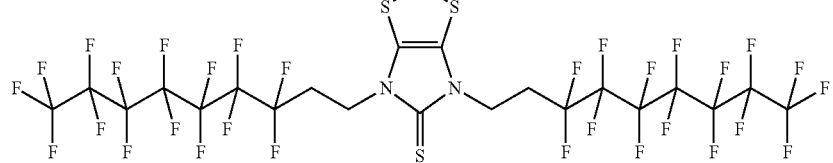

Example 11a a) To 38.05 parts carbondisulfide dissolved in 300 parts chlorobenzene a solution of 9.17 parts 1-amino-2,2-dimethyl-propane in 30 parts chlorobenzene is added at room temperature over 30 minutes. After stirring for further 10 minutes at room temperature the precipitate formed is filtered off, washed with some acetone and dried in vacuo at 30° C. The resulting 11.6 parts are dissolved in 400 parts chlorobenzene, 22.43 parts 3,3,4,4,5,5,6,6,6-nonafluoro-hexyl-1-amine are added and the reaction mixture is heated to 132° C. within 30 minutes. After 45 minutes at reflux temperature the solvent is distilled off by a rotary evaporator and the oily residue is dried in vacuo at 50° C. The resulting intermediate is dissolved in 500 parts dichloromethane and 9.1 parts oxalyl chloride are added within 10 minutes at room temperature. After 30 minutes stirring the reaction mixture is evaporated and dried further in vacuo at 50° C. After cooling the residue solidifies (slightly yellowish aspect): 14.7 parts of compound 11a.

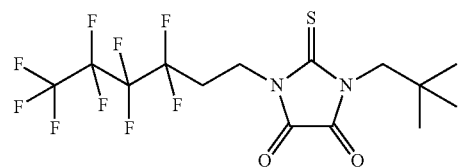
(11a)

b) 13.90 parts compound 11a, 0.91 parts nickel powder and 13.43 parts Lawesson's reagent are heated in 300 parts chlorobenzene under nitrogen to 132° C. After 2 hours at reflux temperature the reaction mixture is cooled to 5° C., the precipitate is filtered off, washed with acetone and dried. The crude nickel dithiolene complex A-11 is recrystallized from dichlorobenzene, filtered, washed with acetone and dried in vacuo at 50° C.

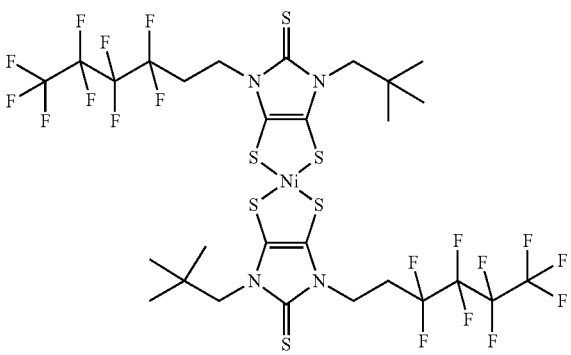
(A-11)

Examples 12 to 16

By proceeding as outlined in Example 11a) but replacing 3,3,4,4,5,5,6,6,6-nonafluoro-hexyl-1-amine by the respective fluoroalkyl amines and continuing according to Example 11b) nickel dithiolene complexes A-12 to A-16 are obtained.

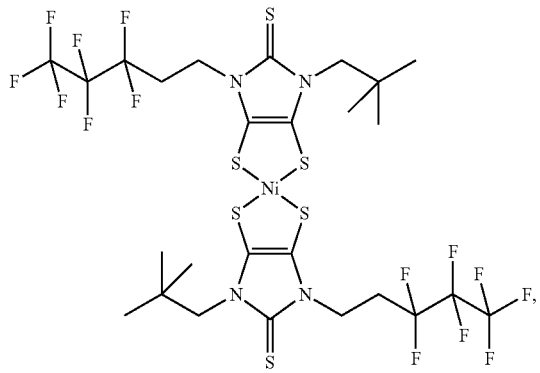
(A-12)

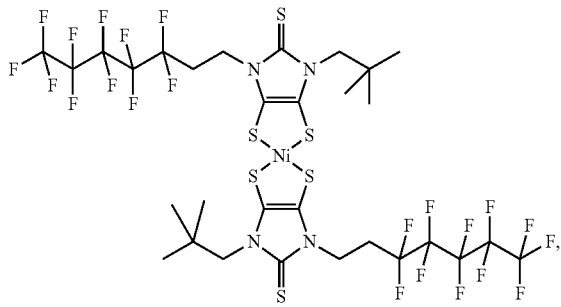
(A-13)

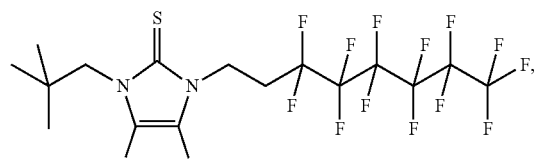
(A-14)

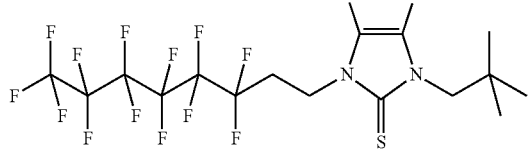

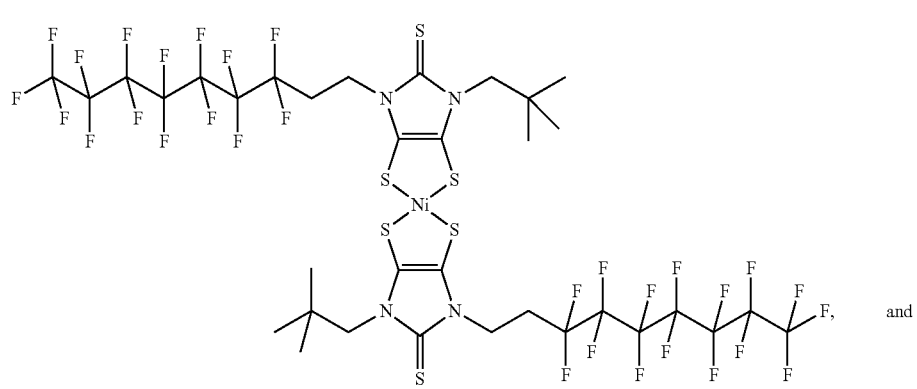

(A-15)

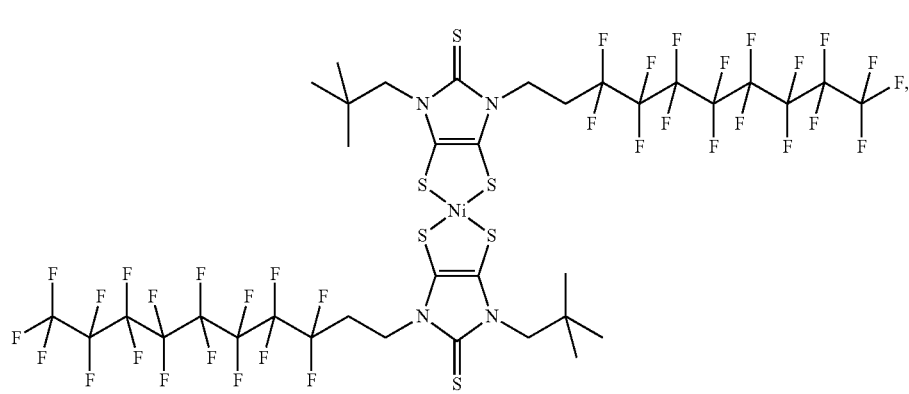

(A-16)

Example 17a a) 3.13 parts isopropyl isothiocyanate are added to 7.90 parts 3,3,4,4,5,5,6,6,6-nonafluoro-hexyl-1-amine at 100° C. within 3 minutes and reacted for 45 minutes. After cooling the reaction mass is dissolved in 900 parts dichloromethane and 4.98 parts oxalyl chloride are added. After 60 minutes the solvent is evaporated by a rotary evaporator and the oily residue is dissolved in 200 parts of hexane. Overnight crystalline needles are formed which are filtered off and dried: 3.3 parts compound 17a.

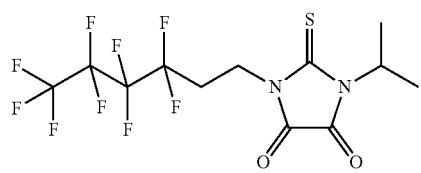

(17a)

b) 0.84 parts compound 17a, 0.06 parts nickel powder and 0.87 parts Lawesson's reagent are heated in 80 parts chlorobenzene under nitrogen to 132° C. and kept at reflux temperature for 90 minutes. After cooling to room temperature the precipitate is filtered off and recrystallized from chlorobenzene: 0.43 parts nickel dithiolene complex A-17.

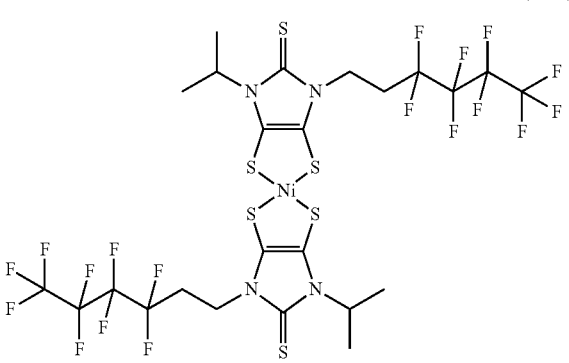

(A-17)

Examples 18 to 22

By proceeding as indicated in Example 17a) but 3,3,4,4,5,5,6,6,6-nonafluoro-hexyl-1-amine is replaced by the respective fluoroalkyl amines and continuing according to Example 17b) the nickel dithiolene complexes A-18 to A-22 are obtained:

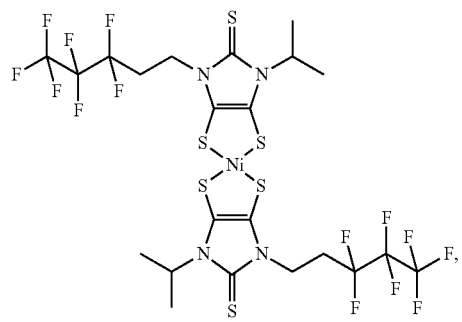 (A-18)

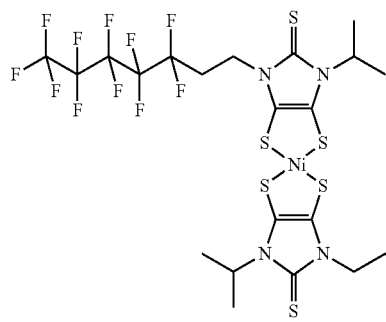 (A-19)

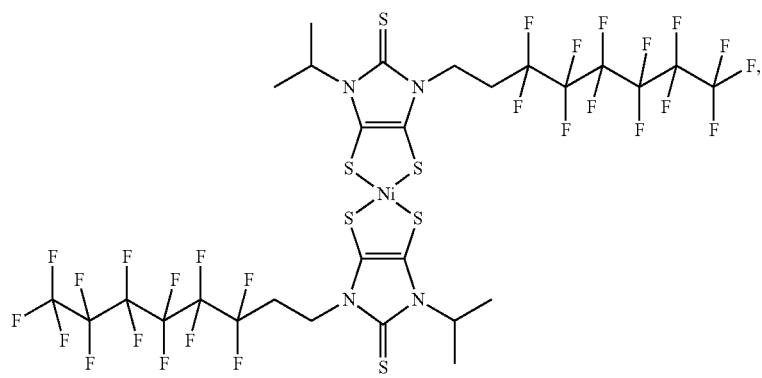 (A-20)

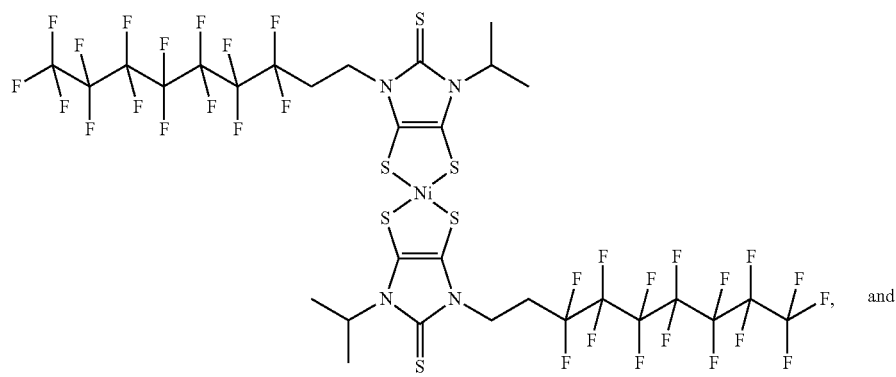 (A-21)

and

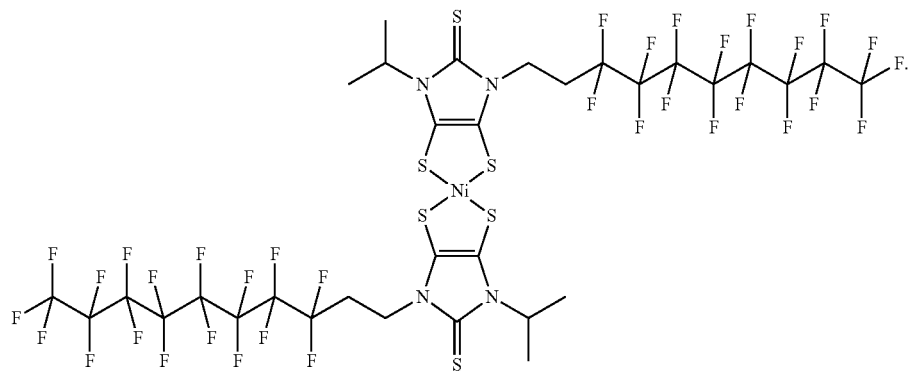 (A-22)

Example 23 a) To 230 parts carbondisulfide dissolved in 500 parts dichloromethane a solution of 7.90 parts 3,3,4,4,5,5,6,6,6-nonafluoro-hexyl-1-amine in 50 parts dichloromethane is added within 60 minutes at room temperature. The white precipitate is filtered off and dried. 2.89 parts of this solid and 2.27 parts octadecylamine are heated together to 110° C. for 2 hours. After cooling to room temperature the solid is dried in vacuo: 7.78 parts compound 23a.

(23a)

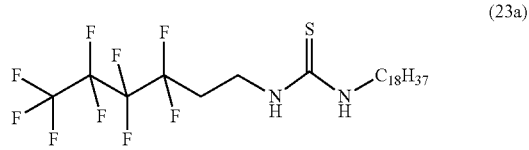

b) 3.80 parts compound 23a are dispersed in 400 parts dichloromethane and 400 parts hexane. Then 1.7 parts oxalyl chloride are added at room temperature. After stirring overnight the clear yellowish solution is evaporated to dryness and the crude compound 23b is recrystallized from hexane.

(23b)

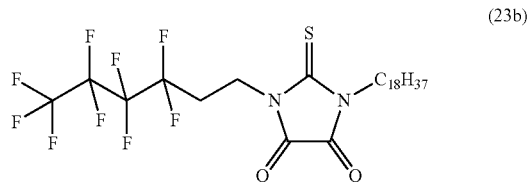

c) 1.0 parts compound 23b, 0.05 parts nickel powder and 0.70 parts Lawesson's reagent are heated in 70 parts chlorobenzene to 132° C. under nitrogen for 2 hours. After cooling to room temperature the precipitate formed is filtered off and recrystallized from chlorobenzene: 0.4 parts nickel dithiolene complex A-23.

(A-23)

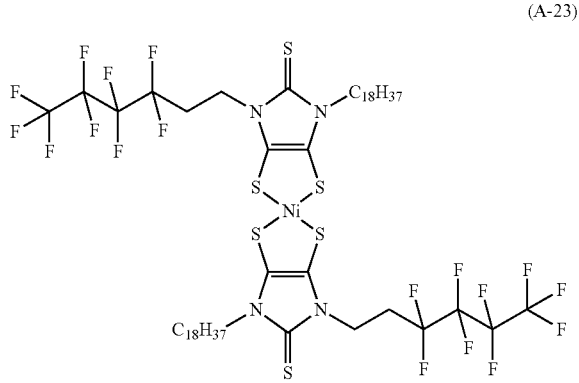

Example 24 a) 20.52 parts 2,2,3,3,4,4,4-heptafluoro-butyl-1-amine and 3.82 parts carbon disulfide are heated in a steel autoclave (100 ml) for 2 hours at 110° C. (pressure rises to about 10 bar). After cooling to room temperature the reaction mass is dried in vacuo at 50° C. The resulting 16.2 parts of a white solid are dissolved in 800 parts dichloromethane and 4.72 parts oxalyl chloride are added at room temperature. After 30 minutes stirring at room temperature the solvent is evaporated and the residue is dissolved in 30 parts 2-propanol. Upon addition of 700 parts hexane the product 24a precipitates overnight (16.25 parts).

(24a)

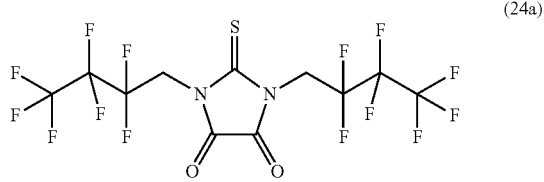 [SMILES: O=C1C(=O)N(CC(F)(F)C(F)(F)C(F)(F)F)C(=S)N1CC(F)(F)C(F)(F)C(F)(F)F]

b) 9.89 parts compound 24a, 0.59 parts nickel powder and 8.70 parts Lawesson's reagent are heated in 400 parts chlorobenzene under nitrogen to 132° C. After 2.5 hours at reflux temperature the reaction mixture is cooled to room temperature and filtered. The residue is recrystallized from dichlorobenzene and washed with acetone. After drying 4.4 parts nickel dithiolene complex A-24 are obtained.

(A-24)

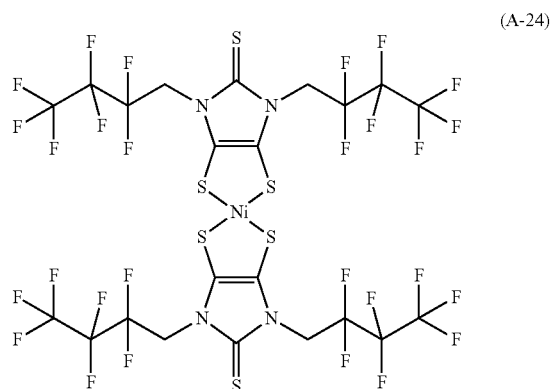

Example 25 a) 0.76 parts carbondisulfide are added to 5.0 parts 2,2,3,3,4,4,5,5,5-nonafluoro-pentyl-1-amine and the reaction mixture is heated to 70° C. overnight and subsequently to 100° C. for 5 hours. After cooling to room temperature the solidified reaction mass is dissolved in 500 parts dichloromethane and 0.67 parts oxalyl chloride are added. After 30 minutes the solvent is evaporated by a rotary evaporator and the residue is dissolved in 30 parts hot 2-propanol. Upon addition of 300 parts heptane and standing overnight a precipitate is formed which is filtered off and dried: 1.6 parts compound 25a.

(25a)

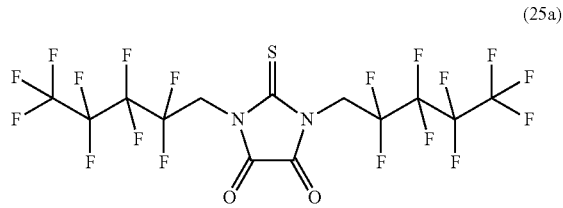 [SMILES: O=C1C(=O)N(CC(F)(F)C(F)(F)C(F)(F)C(F)(F)F)C(=S)N1CC(F)(F)C(F)(F)C(F)(F)C(F)(F)F]

b) 1.6 parts compound 25a, 0.08 parts nickel powder and 1.20 parts Lawesson's reagent are heated under nitrogen in chlorobenzene to 132° C. and kept at reflux temperature for 3.5 hours. After cooling the precipitate is filtered off, recrystallized from chlorobenzene and dried in vacuo: 0.28 parts nickel dithiolene complex A-25 are obtained.

(A-25)

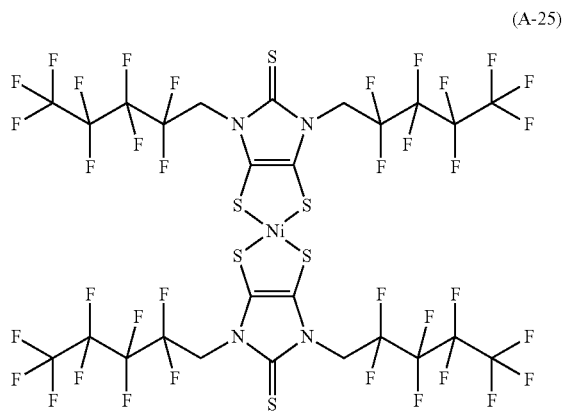

Examples 26 to 33
By proceeding as described in Example 24a) but using instead of 2,2,3,3,4,4,4-heptafluoro-butyl-1-amine the respective fluoroalkyl amines and continuing as indicated in Example 24b) nickel dithiolene complexes A-26 to A-33 are obtained.
(A-26, absorption maximum: 969 nm)
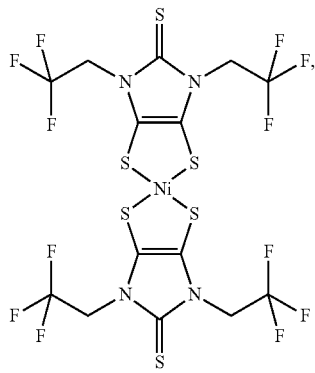
(A-27)
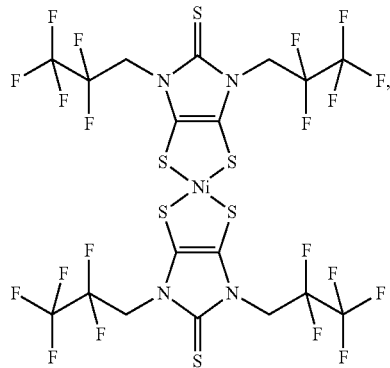
(A-28)
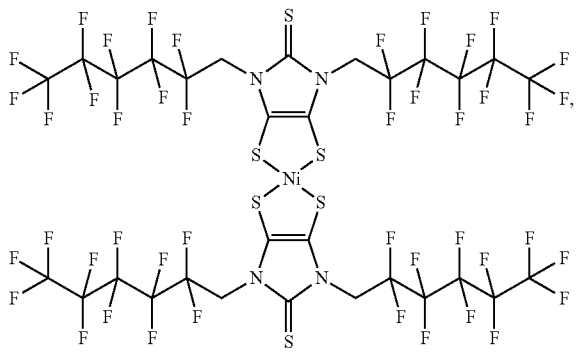
(A-29)
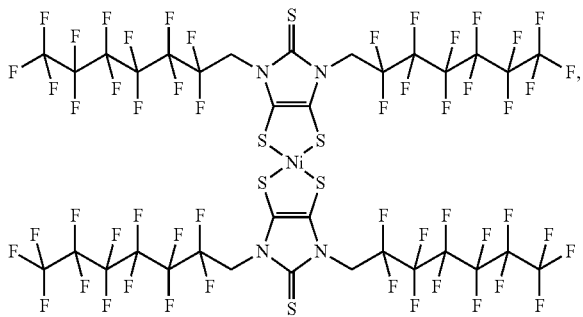

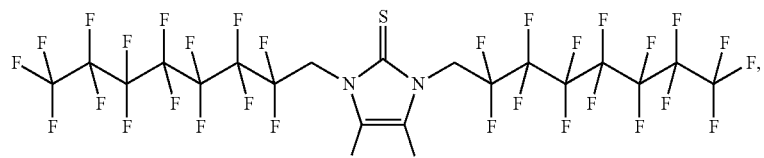
(A-30)

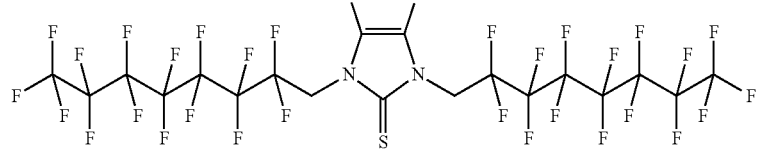
(A-31)

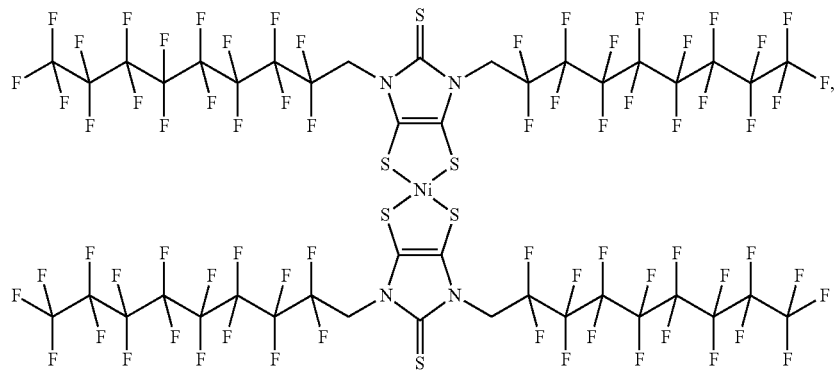
(A-32)

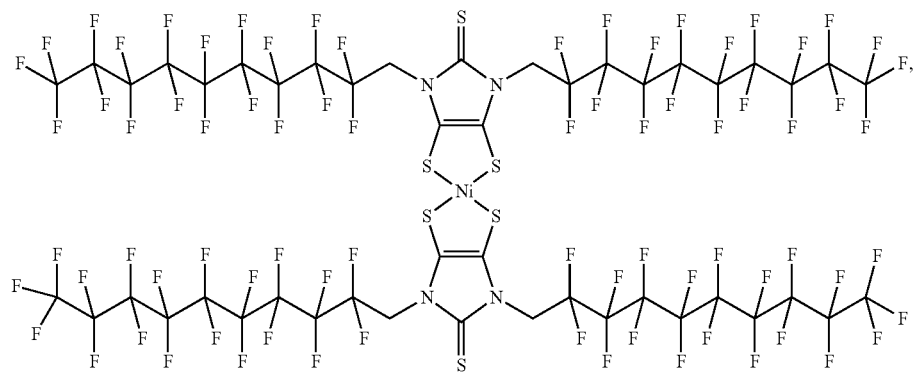
(A-33)

Example 34 a) 5.40 parts 2,2,3,3,4,4,5,5,6,6,7,7,7-tridecafluoro-heptyl-1-amine are dissolved in 100 parts dichloromethane. This solution is cooled to 0° C., 29.3 parts NaOH (6 M) and subsequently 1.51 parts triphosgen dissolved in 20 parts dichloromethane are added over 30 minutes. After stirring overnight at room temperature and cooling to 0° C. again the precipitate is filtered off and recrystallized from ethylacetate.

Further reaction with oxalyl chloride (analog to e.g. Example 25a)) yields 5.8 parts compound 34a.

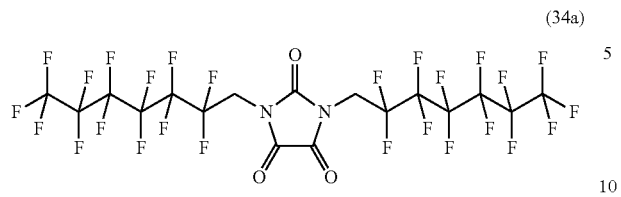
(34a)

b) 1.56 parts compound 34a, 0.06 parts nickel powder and 1.30 parts Lawesson's reagent are heated in 100 parts anisole to 140° C. for 18 hours. After cooling the precipitate is suspended in hot DMF, filtered again, washed with acetone and dried. The product is nickel dithiolene complex A-34 (absorption maximum: 880 nm (DMF).

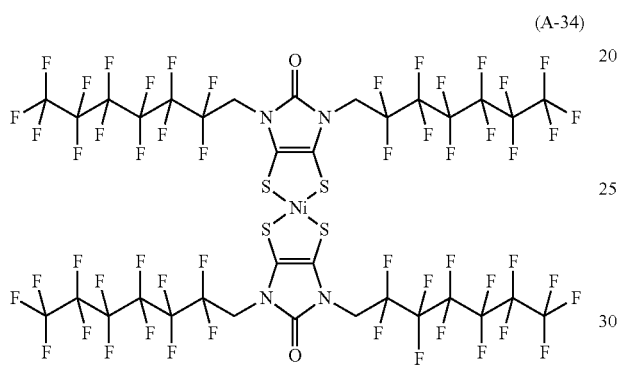
(A-34)

Example 35 a) To 3.81 parts carbondisulfide dissolved in 30 parts chlorobenzene a solution of 0.92 parts 1-amino-2,2-dimethyl-propane in 3 parts chlorobenzene are added at room temperature over 30 minutes. After further stirring for 10 minutes at room temperature the precipitate is filtered off, washed with some acetone and dried in vacuo at 30° C. The resulting 1.16 parts intermediate and 2.6 parts 2,2,3,3,4,4,5,5,5-nonafluoro-pentyl-1-amine are heated to 110° C. in a steel autoclave for 2 hours. After cooling to room temperature the reaction mass is dried in vacuo at 50° C. and redissolved in dichloromethane. Subsequently 1.14 parts oxalyl chloride are added within 10 minutes at room temperature. After 30 minutes stirring the reaction mixture is evaporated by a rotary evaporator and dried further in vacuo at 50° C.: 3.88 parts compound 35a.

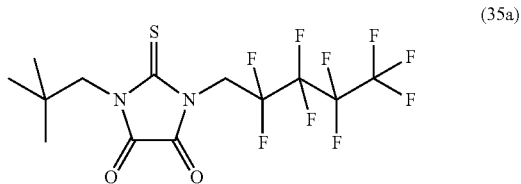 [SMILES: CC(C)(C)CN1C(=O)C(=O)N(CC(F)(F)C(F)(F)C(F)(F)C(F)(F)F)C1=S]
(35a)

b) 3.88 parts compound 35a, 0.26 parts nickel powder and 3.80 parts Lawesson's reagent are heated under nitrogen in 175 parts chlorobenzene to 132° C. After 2 hours at reflux temperature the reaction solution is quickly cooled to room temperature and the resulting precipitate of compound A-35 is filtered off and washed with acetone.

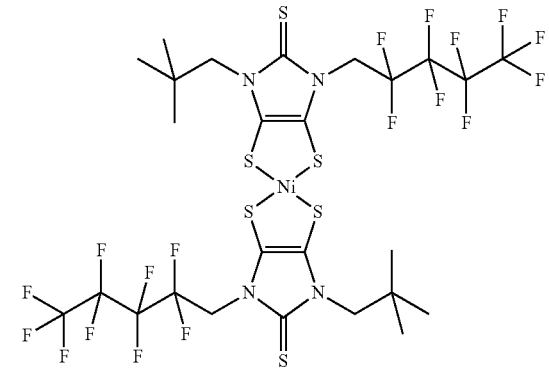
(A-35)

Example 36

2.08 parts isopropyl isothiocyanate are slowly added over 30 minutes to 5.0 parts 2,2,3,3,4,4,5,5,5-nonafluoro-pentyl-1-amine at 100° C. After stirring at 100° C. for further 2 hours the reaction mixture is cooled to room temperature. The solidified reaction mass is dissolved in 700 parts dichloromethane and 2.4 parts oxalyl chloride are added. After 15 minutes the solvent is evaporated with a rotary evaporator and the residue is dissolved in 20 parts 2-propanol. Upon addition of 700 parts ligroin (100-140° C.) and standing overnight crystalline needles are formed. After filtration the crystals are washed with ligroin and dried: 6.15 parts compound 36a.

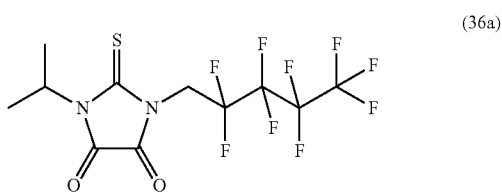 [SMILES: CC(C)N1C(=O)C(=O)N(CC(F)(F)C(F)(F)C(F)(F)C(F)(F)F)C1=S]
(36a)

b) Compound 36a is reacted with nickel powder and Lawesson's reagent according to example 1b to yield nickel dithiolene complex A-36.

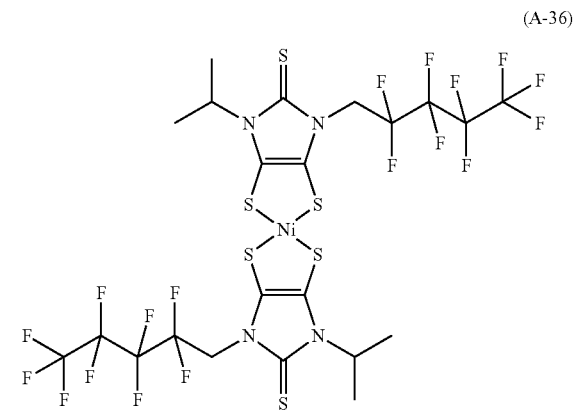
(A-36)

Example 37 to 54

By proceeding as described in Examples 35a), or 36a) but using instead of 2,2,3,3,4,4,5,5,5-nonafluoro-pentyl-1-amine the respective fluoroalkyl amines and continuing further as indicated in Examples 35b), or 36b) nickel dithiolene complexes A-37 to A-54 are obtained.

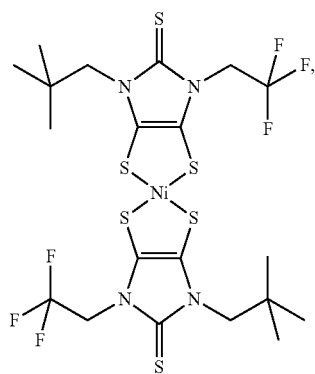 (A-37)
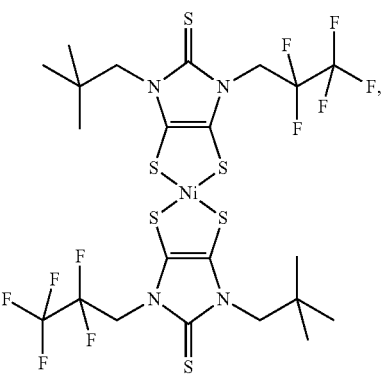 (A-38)
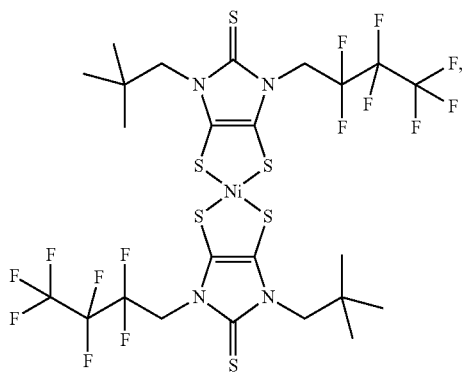 (A-39)
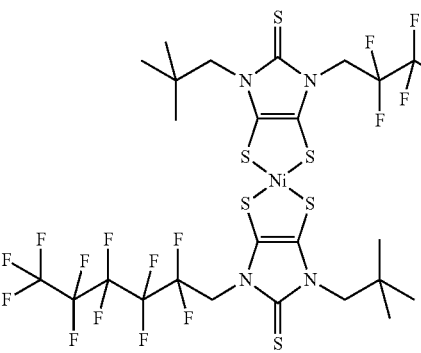 (A-40)
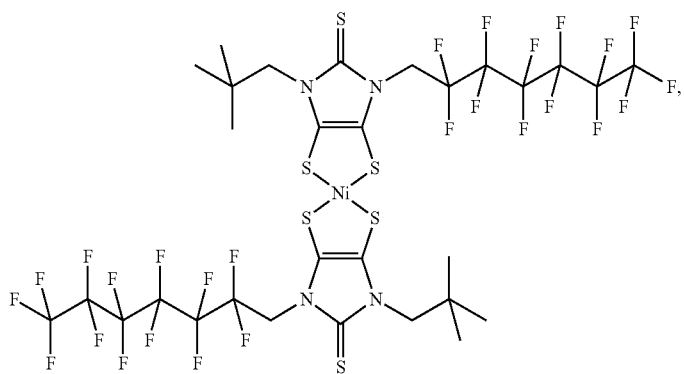 (A-41)
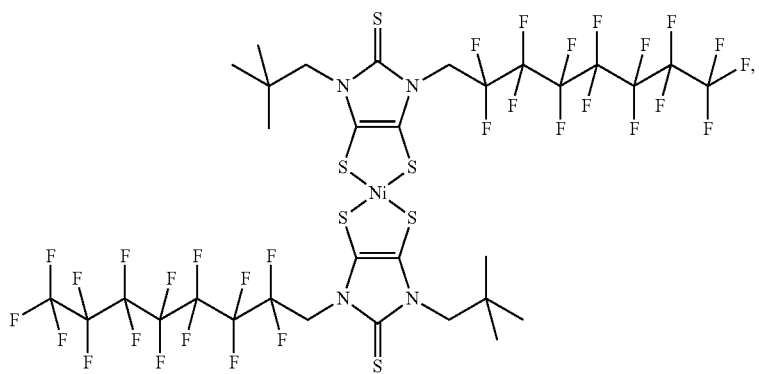 (A-42)

-continued
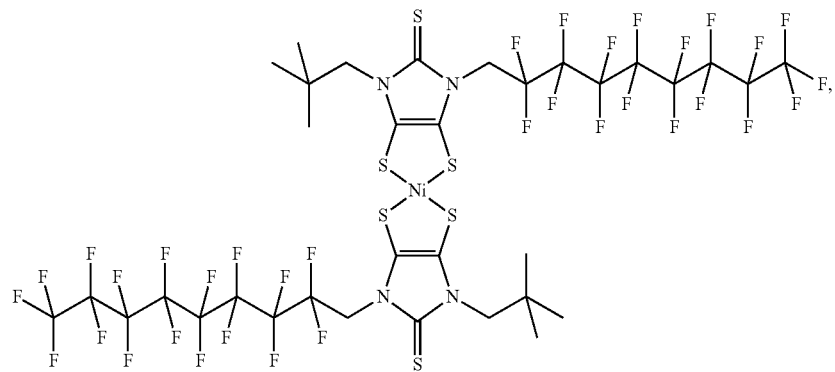
(A-43)
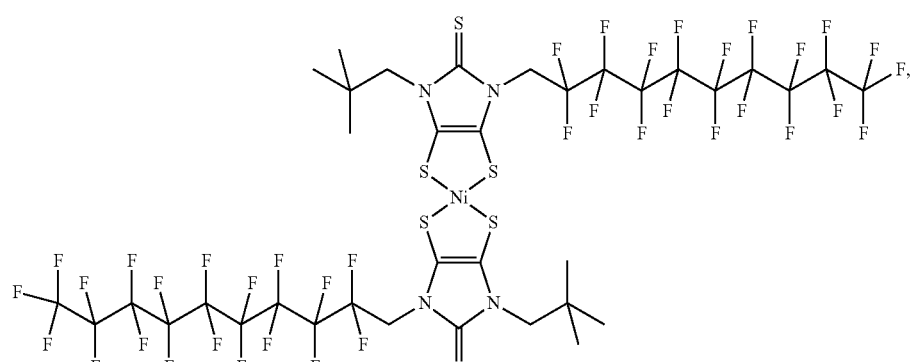
(A-44)
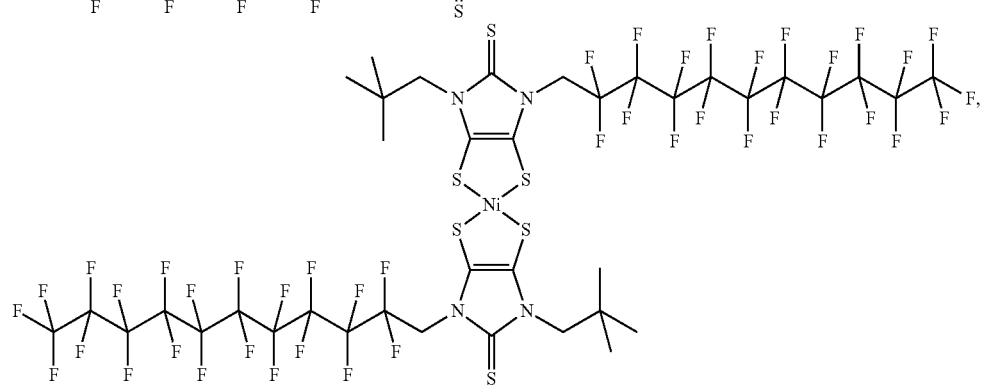
(A-45)

-continued
(A-46)
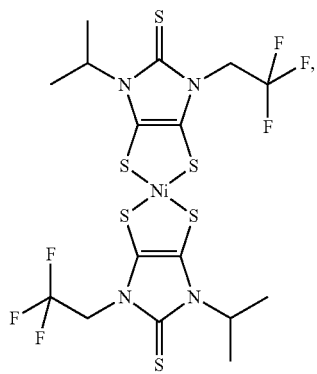
(A-47)
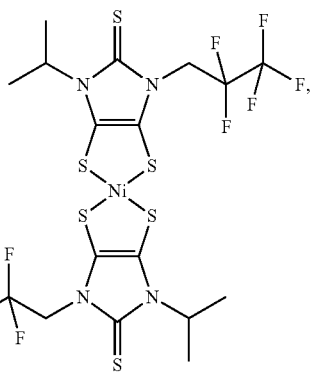
(A-48)
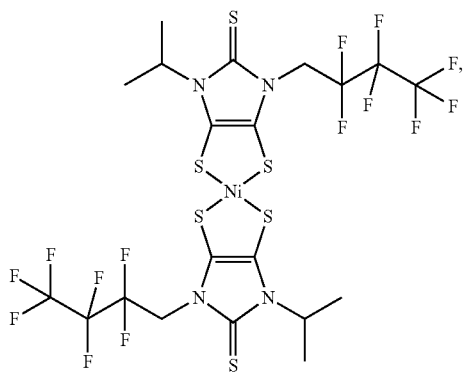
(A-49)
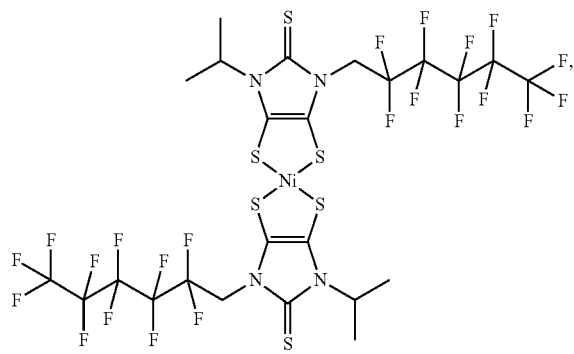
(A-50)
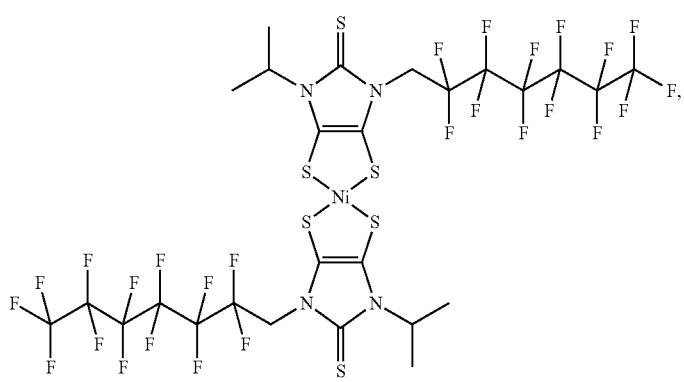
(A-51)
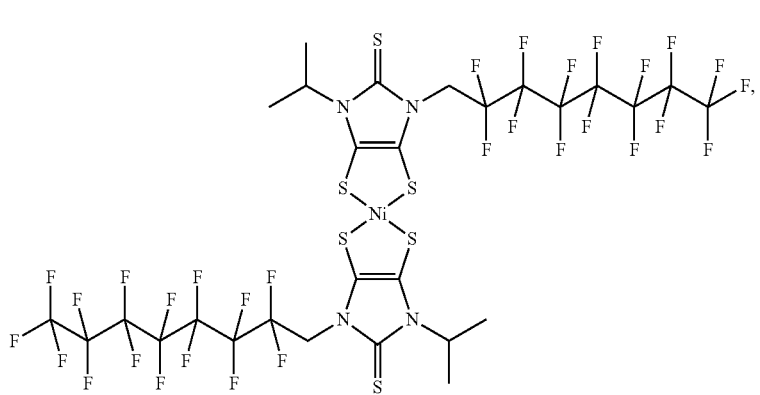

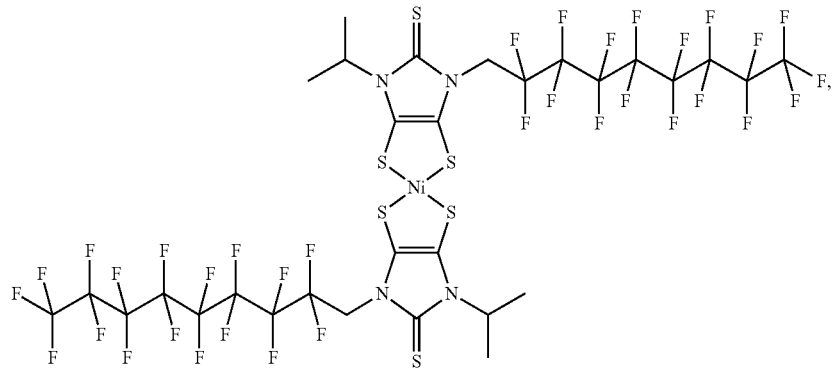
(A-52)
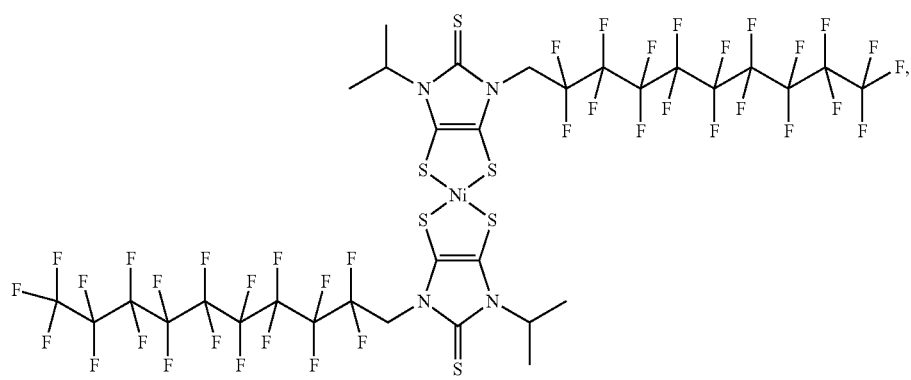
(A-53)
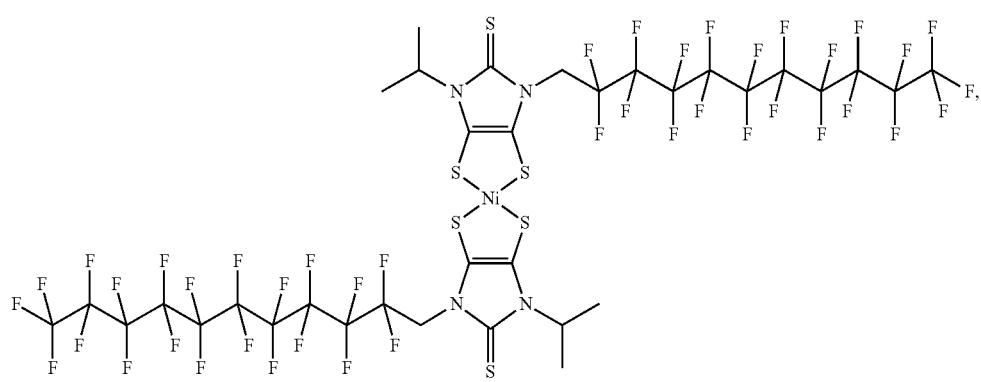
(A-54)

Example 55

6.36 parts of 4,4,4-trifluoro-butyl-1-amine and 1.91 parts carbondisulfide are reacted together in 400 parts dichloromethane at reflux temperature for 22 hours. Subsequently 4.75 parts oxalyl chloride are added in 3 portions over 2 hours. The solvent is then evaporated by a rotary evaporator. The solid residue is dissolved in chlorobenzene and reacted with nickel powder and Lawesson's reagent analogously to example 1b yielding nickel dithiolene complex A-55 (absorption maximum: 996 nm; absorbance coefficient: 70,500).

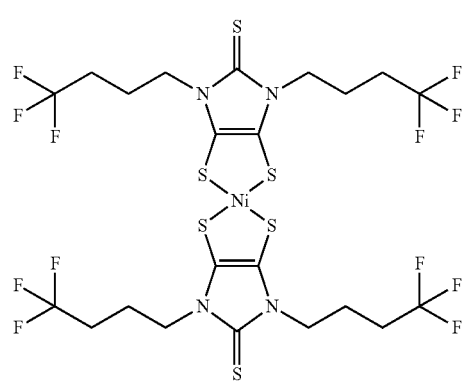

(A-55)

Example 56

By proceeding as described in example 34a but using 3,3,4,4,5,5,6,6,6-nonafluoro-hexyl-1-amine instead of 2,2,3,3,4,4,5,5,6,6,7,7,7-tridecafluoro-heptyl-1-amine and proceeding further as described in example 34b nickel dithiolene complex A-56 is obtained.

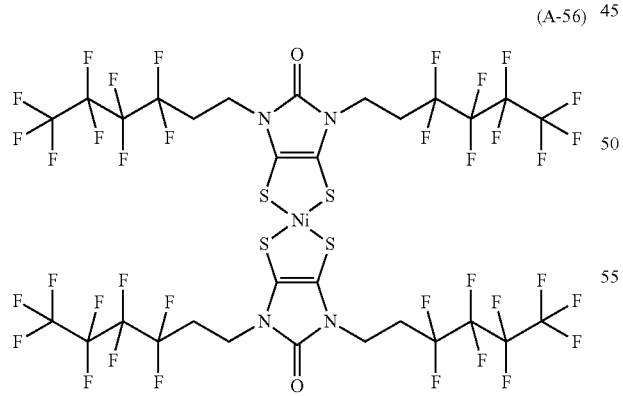

(A-56)

Example 57

By proceeding as described in Example 1b) but using a mixture of compounds 1a and 11a then a mixture of nickel dithiolene complexes A-1, A-11 and A-57 is obtained.

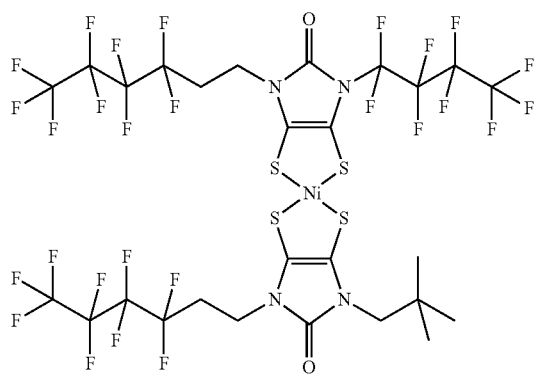

(A-57)

Example 58 a) 22 parts 2,3-dicyano-1,4-dibutoxynaphthalene are dissolved in 250 parts NMP while heating to 80° C. 50 parts potassium carbonate are added and subsequently 90 parts 3,3,4,4,5,5,6,6,6-nonafluoro-1-iodo-hexane. The reaction mixture is kept at 80° C. for 18 hours. Then 400 parts water are added over 1 hour and after cooling to room temperature the crystals formed are collected by filtration and dried in vacuo at 50 to 60° C.: 41.3 parts compound 58a.

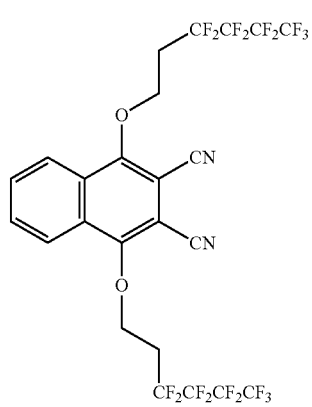

(58a)

b) 2.5 parts compound 58a, 25 parts urea, 0.1 parts ammonium molybdate and 0.25 parts vanadium (III) chloride are mixed thoroughly in a mortar and then heated to 190° C. for 1 hour. The reaction mixture is dissolved in 200 parts dichloromethane and extracted with 100 parts water. The dichloromethane solution is evaporated by a rotary evaporator to dryness. The dark solid is dissolved in toluene, filtered over silica and the filtrate is evaporated to dryness: 1.6 parts naphthalocyanine A-58 (absorption maximum 915 nm).

(A-58)

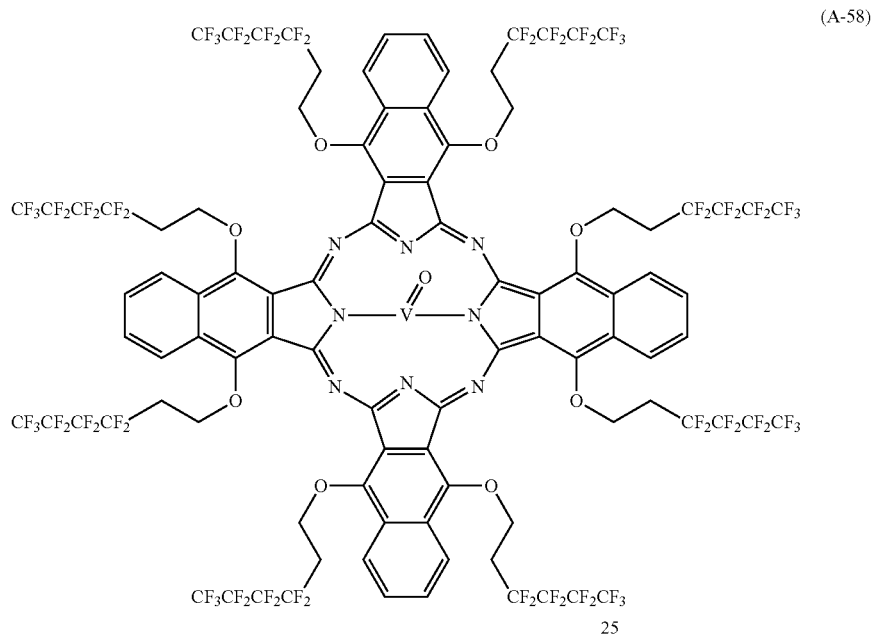

Example 59

1.67 parts 2-methyl-benzo[c,d]indole (A) and 4.86 parts 3,3,4,4,5,5,6,6,6-nonafluoro-1-iodo-hexane are heated in 100 parts chlorobenzene at reflux temperature for 5 h. After cooling the reaction mixture is evaporated partially and filtered.

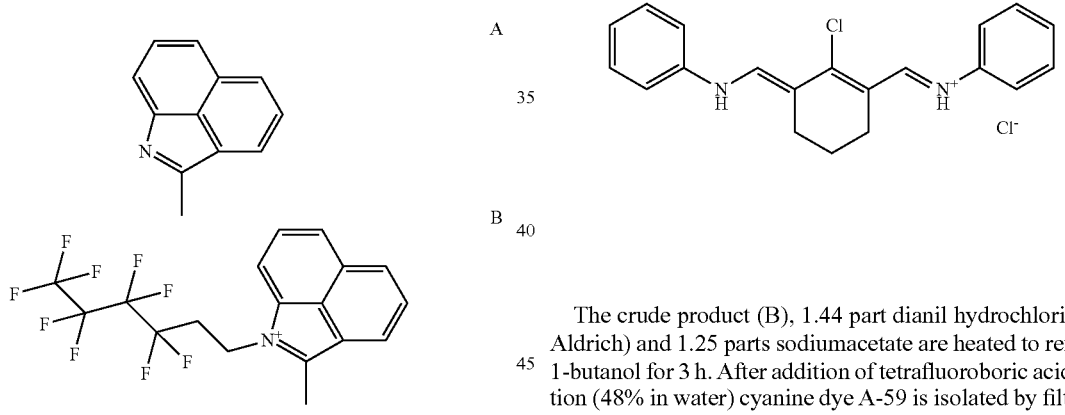

A

B

C

The crude product (B), 1.44 part dianil hydrochloride (C; Aldrich) and 1.25 parts sodiumacetate are heated to reflux in 1-butanol for 3 h. After addition of tetrafluoroboric acid solution (48% in water) cyanine dye A-59 is isolated by filtration (3.41 parts; 1019 nm).

A-59

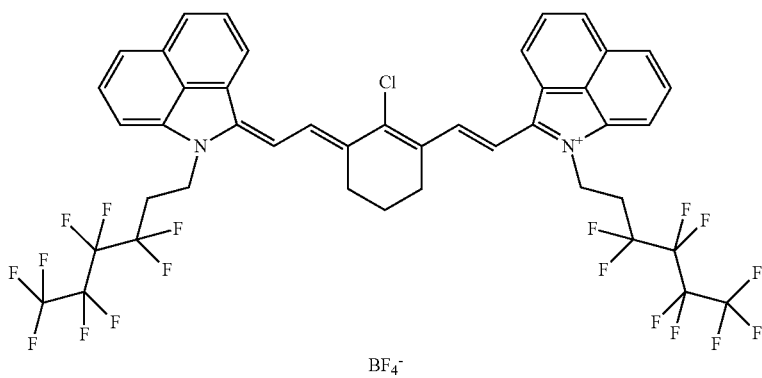

$BF_4^-$

Examples 60 to 65
Proceeding analog to example 59 the following cyanine dyes are prepared:
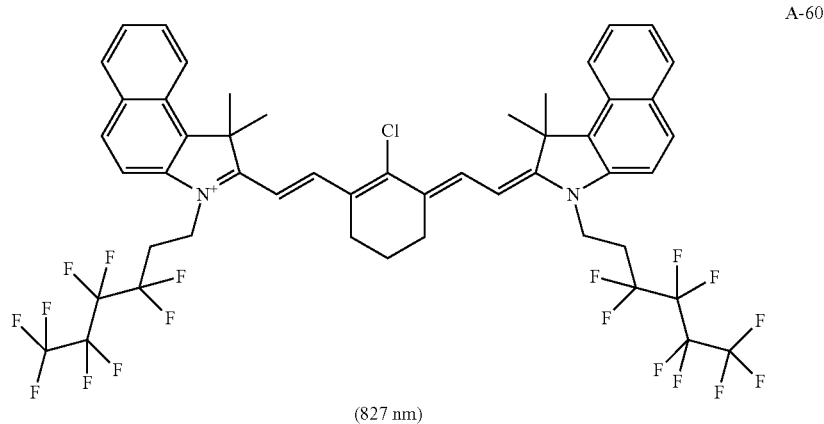
A-60
(827 nm)
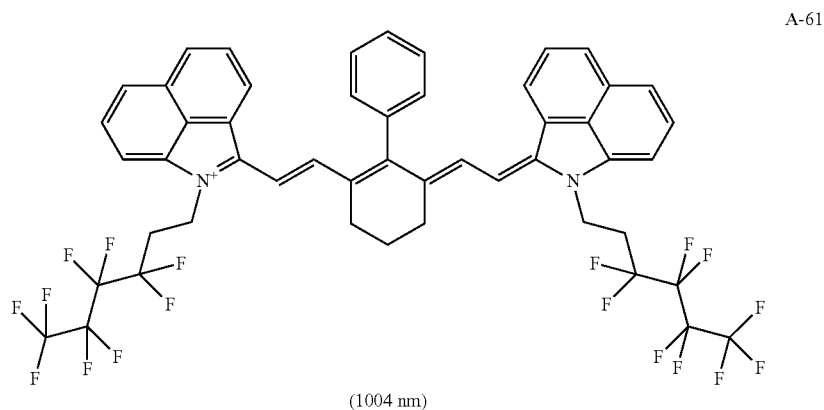
A-61
(1004 nm)
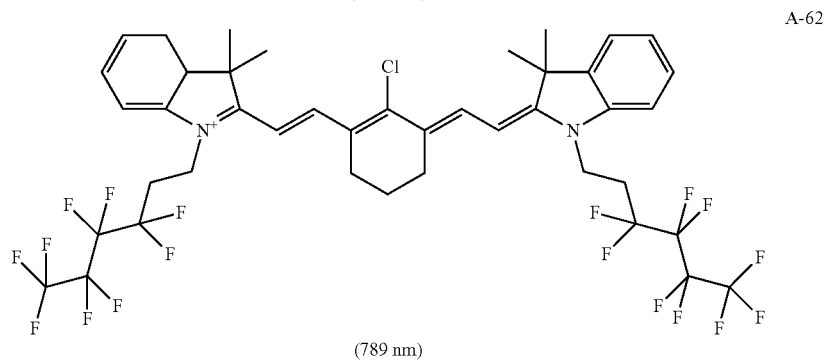
A-62
(789 nm)
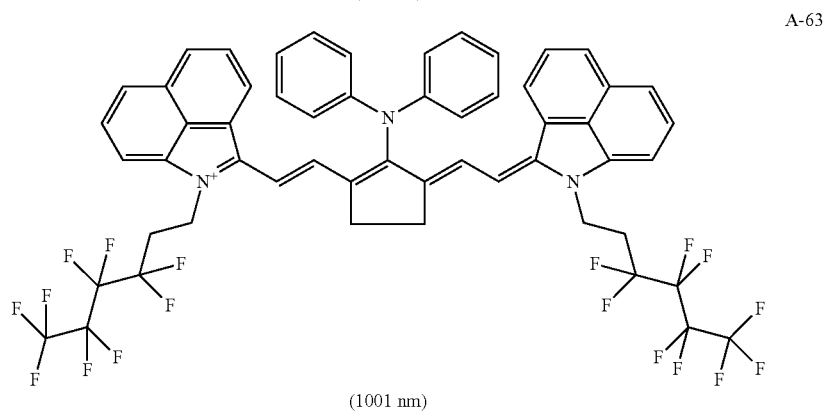
A-63
(1001 nm)

A-64

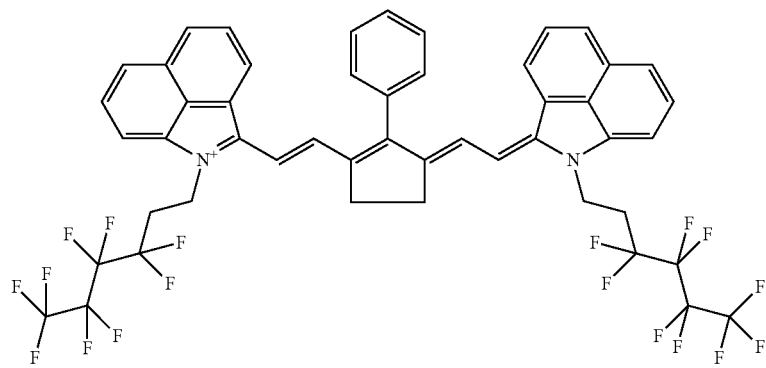

(1031 nm)

A-65

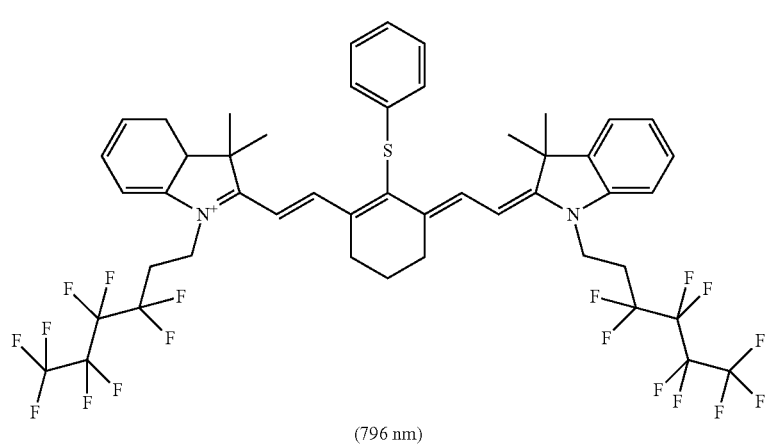

(796 nm)

APPLICATION EXAMPLES

Application Example 1 (Printing)

11.9 parts of vinyl chloride, 2.1 parts of vinyl acetate, 10 parts of ethoxypropanol, 75.5 parts of methyl ethyl ketone and 1.0 parts of the product from Example 1 (Cpd. A-1) are shaken together with 150 parts of glass beads for 30 minutes in a Skandex mixer.

The resulting printing ink is applied to contrast paper using a doctor blade (film thickness when damp: 6 μm). The print is visually colorless, but is clearly visible in the IR range using an IR-viewing device (cut-off filter 715 nm). The fastness to light, chemical agents and solvents is excellent.

Application Example 2 (Printing)

By proceeding as indicated in Example A1 but using the IR absorber from Example 11 (Cpd. A-11), there accordingly is likewise obtained a colorless print having excellent fastness to light, which is clearly visible in the infrared range using an IR-viewing device. Resistance against chemicals and solvents is excellent too.

Application Example 3 (Printing)

An offset ink absorbing IR radiation is prepared containing 2.5 weight percent on solids of the compound from Example 1 (Cpd. A-1). The ink is prepared on a 3-roll mill and comprises 10 weight percent of high tack varnish (CAS 68458-35-5, alkyd resin), 84 weight percent of a commercial offset varnish and 1 weigh percent of a drying agent (based on CAS 136-52-7; cobalt bis(2-ethylhexanoate) and oleic acid, CAS 112-80-1). The ink is printed by an offset printing equipment to banknote paper. The print is visually almost colorless, but is clearly visible in the IR range using an IR-viewing device (cut-off filter 715 nm). The print exhibits excellent light fastness and very good resistance against solvents, acids, bases, hydrogen peroxide, hypochlorite, sodium sulfite, boiling water etc. (cf. comparative example below).

Application Example 4 (Printing)

By proceeding as indicated in Application Example 3 but using the IR absorber from Example 11 (Cpd. A-11), there accordingly is likewise obtained a colorless offset print having excellent fastness to light, which is clearly visible in the infrared range using an IR-viewing device. Resistance against solvents, acids, bases, hydrogen peroxide, hypochlorite, sodium sulfite, boiling water etc. is excellent (cf. comparative example below).

Application Example 5 (Printing)

By proceeding as indicated in Application Example 3 but using the IR absorber from Example 24 (Cpd. A-24), there accordingly is likewise obtained a colorless offset print having excellent fastness to light, which is clearly visible in the infrared range using an IR-viewing device. Resistance against solvents, acids, bases, hydrogen peroxide, hypochlorite, sodium sulfite, boiling water etc. is excellent (cf. comparative example below).

Comparative Application Example (Printing)

By proceeding as indicated in Application Example 3, but using 2 weight percent on solids (corrected for molecular weight relation) IR absorber from Example 1 of WO2008/086931 with the structure indicated below there accordingly is likewise obtained a colorless offset print having excellent fastness to light which is clearly visible in the infrared range using an IR-viewing device.

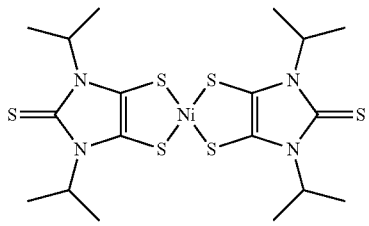

Resistance against solvents like ethanol, white spirit, acids, bases, hydrogen peroxide synthetic sweat and detergents is excellent. But resistance against solvents like toluene, acetone, boiling water or against aggressive chemicals like hypochlorite is not sufficient for banknote printing.

For testing procedure cf. "Chemical and Physical Resistance" in "Extract of the ANNEX 13 of the Technical Specification for Euro banknote production" (European Central Bank; July 2004).

In the following table the test results of the critical fastnesses are given for Application Example 3, 4, 5 and the present Comparative Application Example.

| Resistance against: | Appl. Example 3 | Appl. Example 4 | Appl. Example 5 | Comparative Example |
|---|---|---|---|---|
| Acetone | 3-4 | 4 | 3 | 1 |
| Toluene | 4 | 3-4 | 4 | 1 |
| Hypochlorite (5%) | 3-4 | 3-4 | 3-4 | 1 |
| Boiling Water | 4 | 3 | 4 | 1-2 |

Evaluation by IR camera with cut-off filter (715 nm)
Ranking list according to the European Central Bank
4: no change or minor changes not visible with naked eyes
3: minor change
2: considerable change; less than 50% damaged
1: major change; more than 50% damaged
0: element disappeared Application Example 6 (Printing)

When proceeding analog to application example 3, but applying the cyanine dye from example 59 prints are obtained which exhibit distinctly better resistance against boiling water, hypochlorite and solvents in comparison to corresponding prints with the commercial dye S 0734 (FEW Chemicals, Germany).

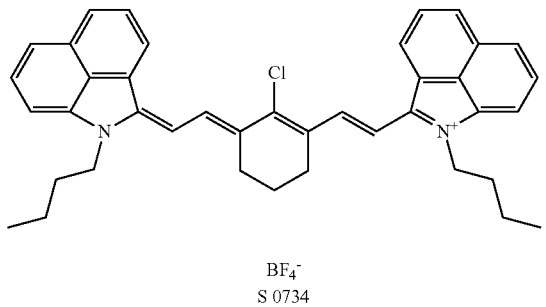 [SMILES: CCCCn1/c(=C/C=C2\CCCC(/C=C/C3=[N+](CCCC)c4cccc5cccc3c45)=C2Cl)c2cccc3cccc1c32 ; "BF4-S 0734"]

BF$_4^-$
S 0734

Application Example 7 (Laser-Welding of Plastics)

Using an injection-moulding machine, the IR absorber from Example 1 (Cpd. A-1) is incorporated into a polycarbonate disc having a thickness of 2 mm (concentration: 100 ppm). Using an Nd:YAG laser, the resulting, virtually colorless disc is welded at a power of 30 watt and a rate of advance of 20 mm/s to a second 1 mm-thick pure polycarbonate disc not containing IR absorber. The resulting weld is characterised by an excellent bond, unchanged transparency, no melt irruptions and no bubbling. Under heavy mechanical loading, breakage of the discs does not occur at the welded seam.

Application Example 8 (Laser-Welding of Plastics)

By proceeding as indicated in Application Example 6 but using the IR absorber from Example 3 (Cpd. A-3), a virtually colorless polycarbonate disc is likewise obtained which has excellent welding properties. The resulting weld has unchanged transparency, the welding leaves no melt irruptions or bubbling and the strength of the weld is excellent.

Application Example 9

By proceeding as indicated in Application Examples 6 and 7 but, instead of using an Nd:YAG laser (1064 nm), using a diode laser having an emission wavelength of 980 nm, similarly good results to those described in Application Examples 5 and 6 are obtained.

Application Example 10 and 11

By proceeding as indicated in Application Examples 6 and 7 but, instead of using an Nd:YAG laser (1064 nm), using a diode laser having an emission wavelength of 940 nm, a comparably good weld is obtained at a laser power of 80 watt.

Application Example 12

By proceeding as indicated in Application Example 6, but using polypropylene discs having a thickness of 1.5 mm, the welds obtained are likewise very good.

The invention claimed is:

1. A metal dithiolene complex of formula (I)

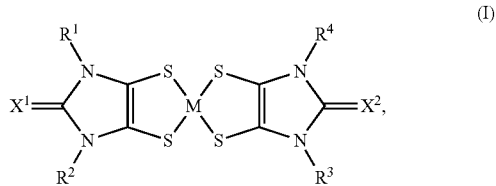

wherein
M is Ni, Pd, or Pt;
$X^1$ and $X^2$ are each independently sulfur or oxygen;
at least one of the substituents $R^1$, $R^2$, $R^3$ and $R^4$ is a group $R_f$ having a formula— —(CH$_2$)$_n$—(CF$_2$)$_m$—F,
the substituents $R^1$, $R^2$, $R^3$ and $R^4$ are each independently the group $R_f$, an unsubstituted or substituted alkyl group, or an unsubstituted or substituted aryl group,

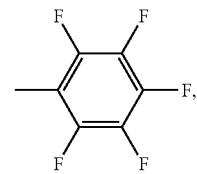

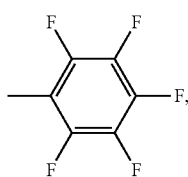

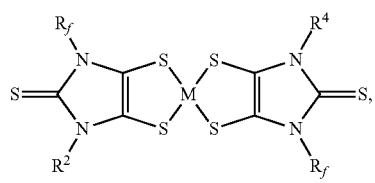
(Ib)

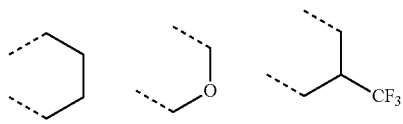

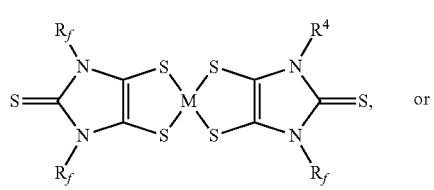
(Ic) or

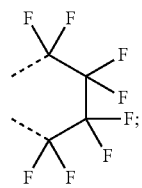

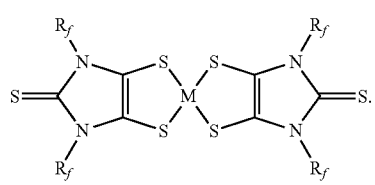
(Id)

m+n is an integer of 4 to 10,
n is an integer of 1 or 2, and
m is an integer of 3 to 8.

2. The metal dithiolene complex of claim 1, having a formula (Ia), (Ib), (Ic) or (Id)

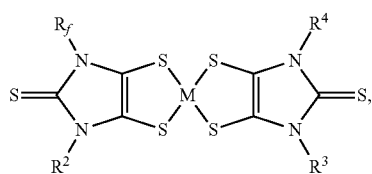
(Ia)

3. The metal dithiolene complex of claim 1, wherein two of the substituents $R^1$, $R^2$, $R^3$ and $R^4$ are the group R and the other two of the substituents $R^1$, $R^2$, $R^3$ and $R^4$ are substituted or unsubstituted straight-chain, branched or cyclic $C_1$-$C_{18}$ alkyl radicals; or all of the substituents $R^1$, $R^2$, $R^3$ and $R^4$ are the group $R_f$.

4. The metal dithiolene complex of claim 1, wherein M is Ni.

5. The metal dithiolene complex of claim 1, having a formula selected from the group consisting of (A-1) to (A-57)

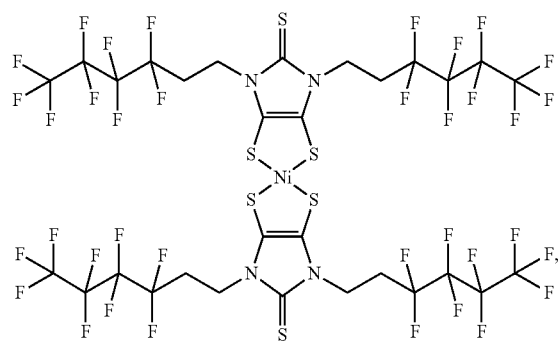
(A-1)

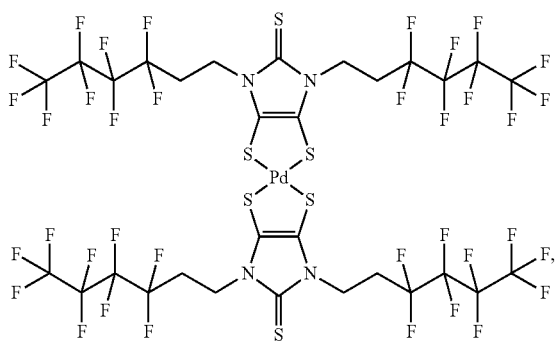
(A-2)

(A-3) 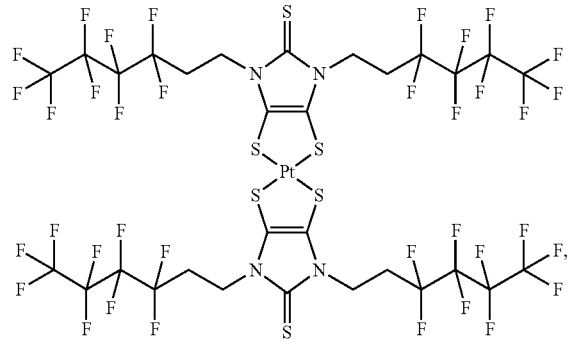
(A-4) 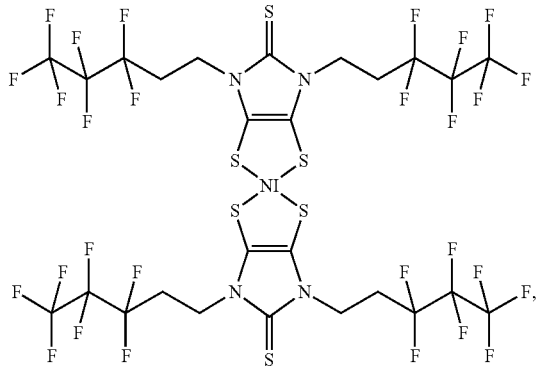
(A-5) 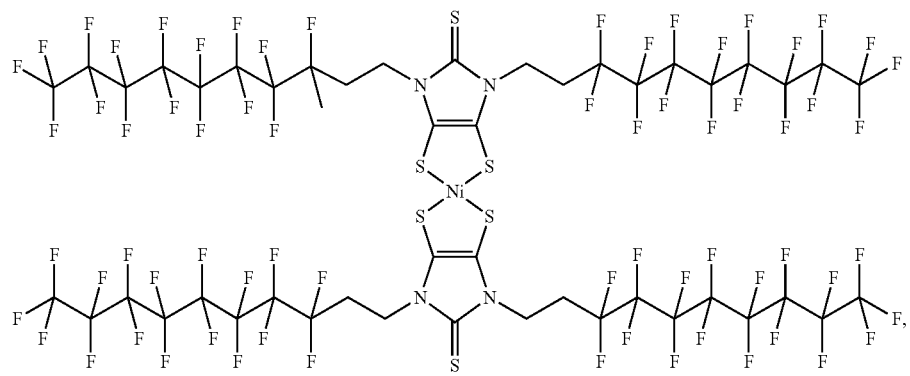
(A-6) 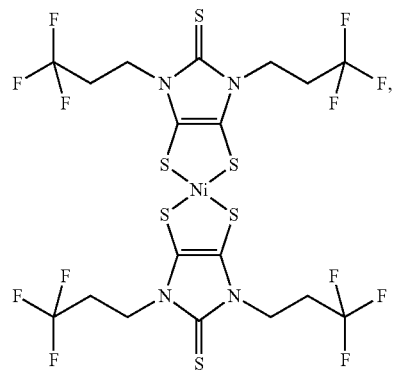
(A-7) 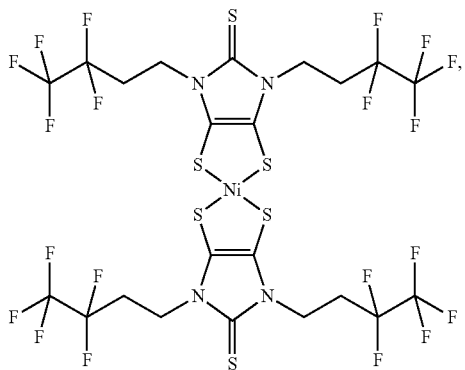
(A-8) 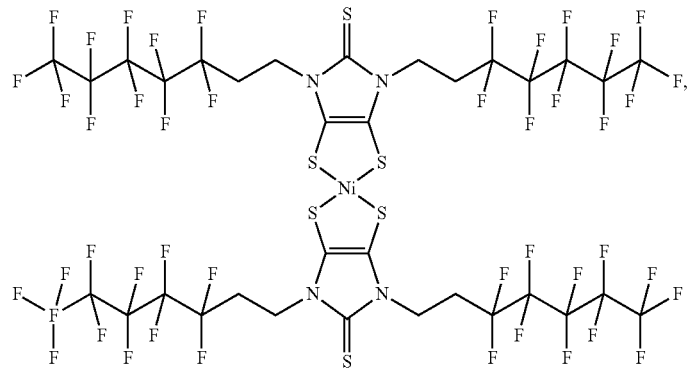

(A-9)
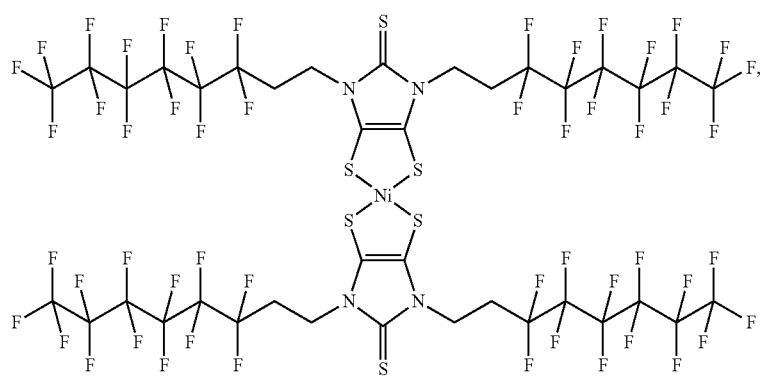
(A-10)
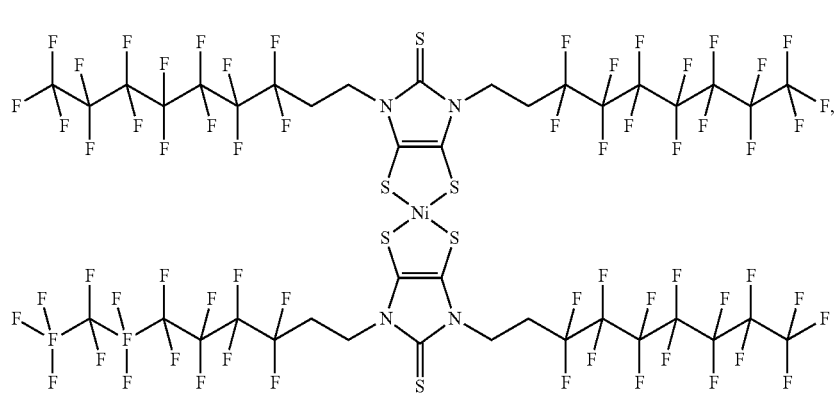
(A-11)
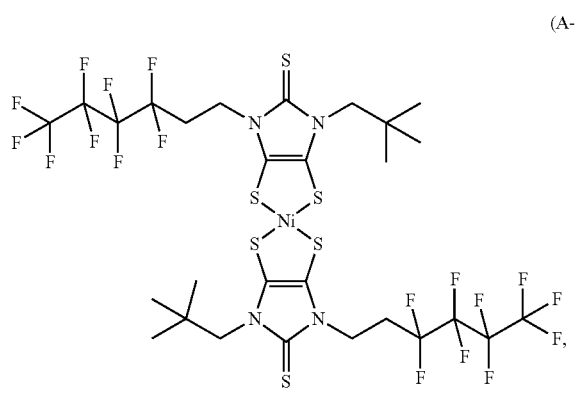
(A-12)
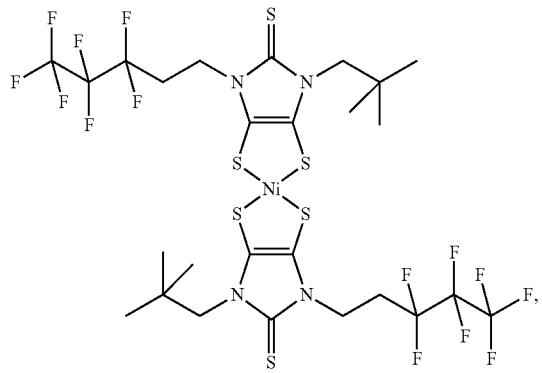
(A-13)
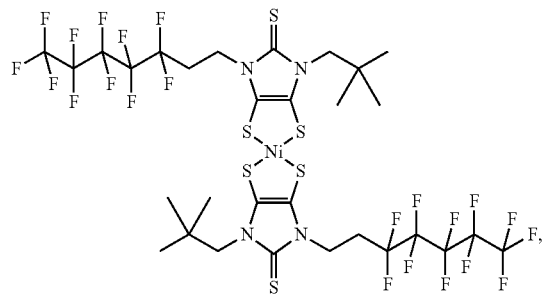
(A-14)
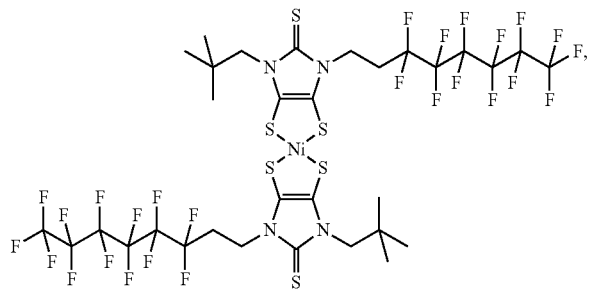

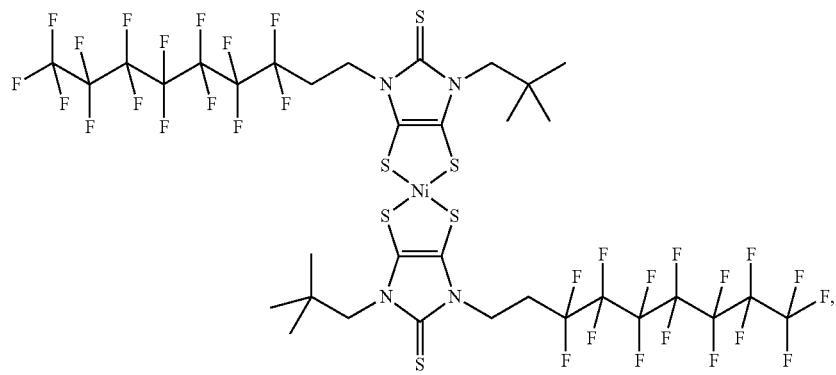
(A-15)
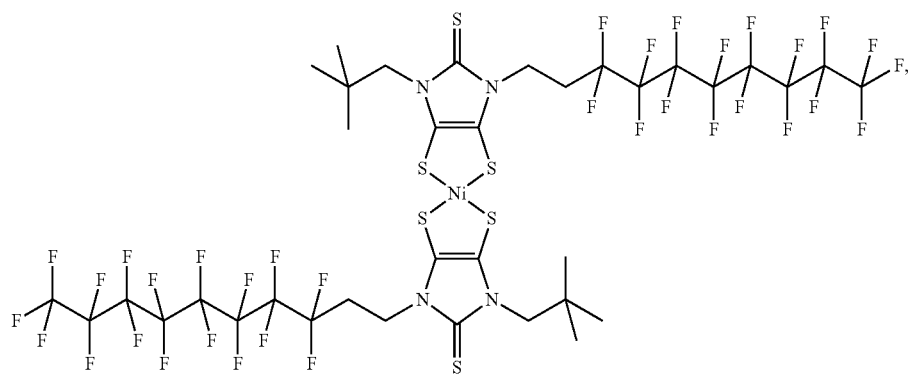
(A-16)
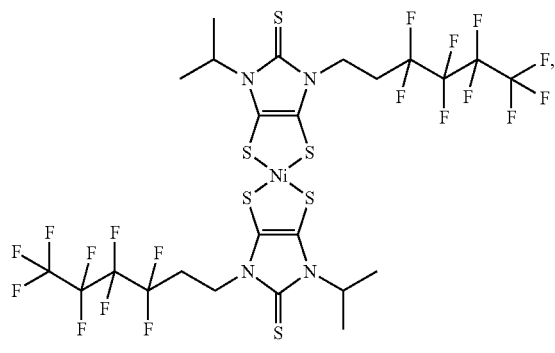
(A-17)
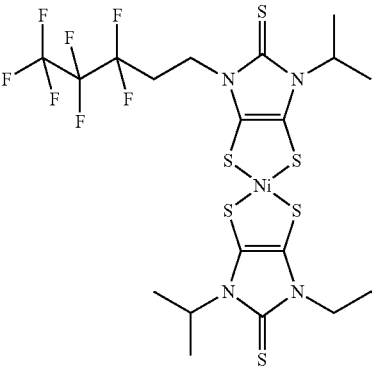
(A-18)
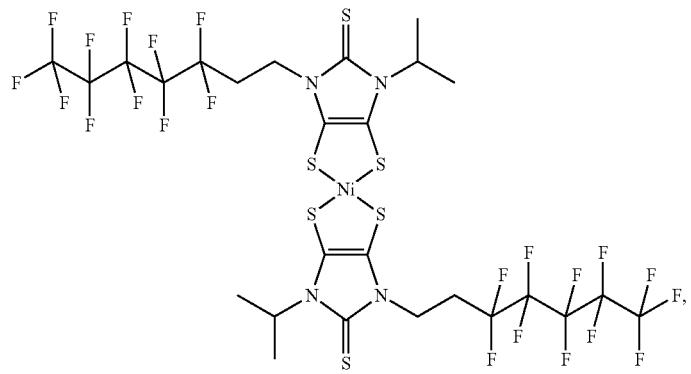
(A-19)

-continued
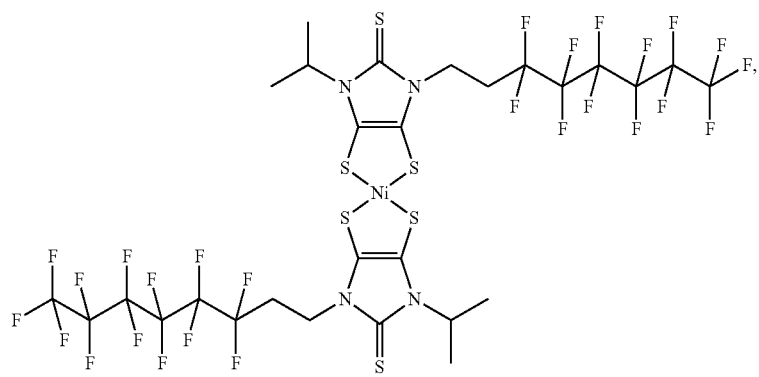
(A-20)
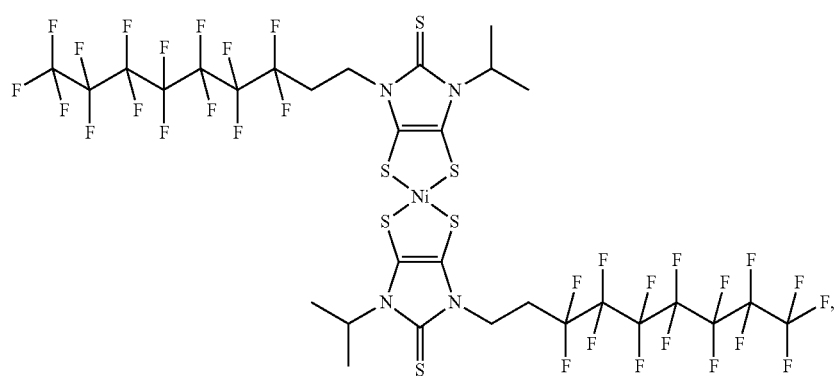
(A-21)
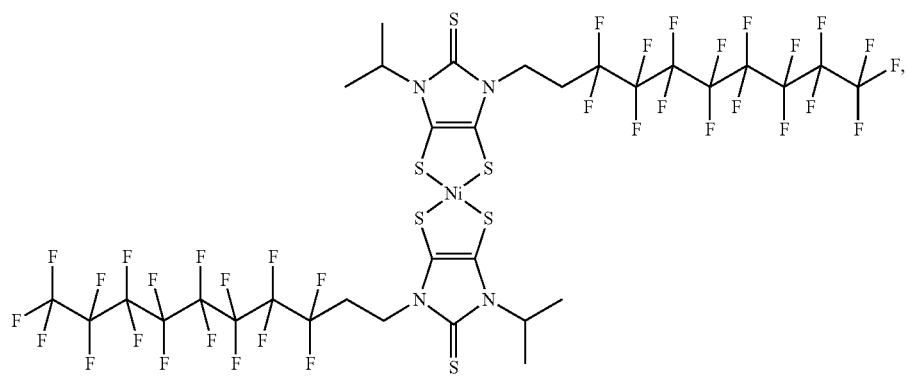
(A-22)
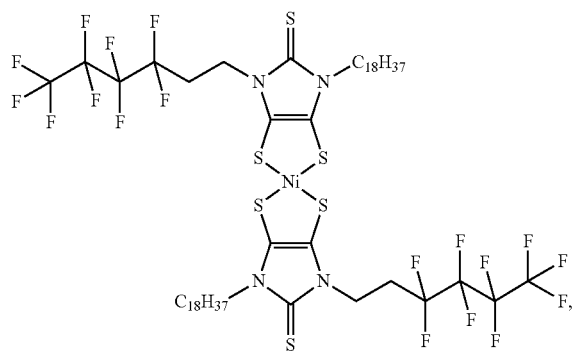
(A-23)
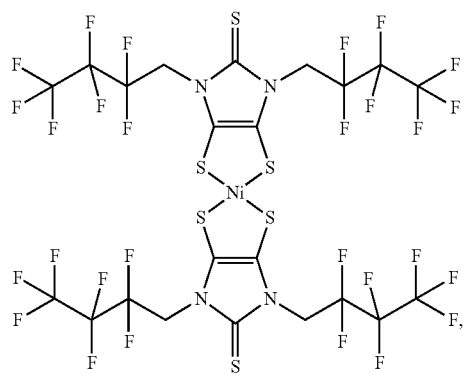
(A-24)

-continued
(A-25)
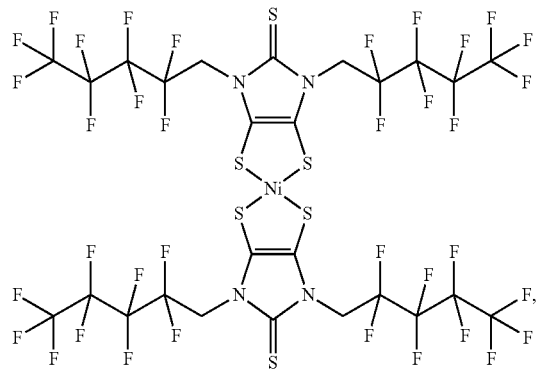
(A-26)
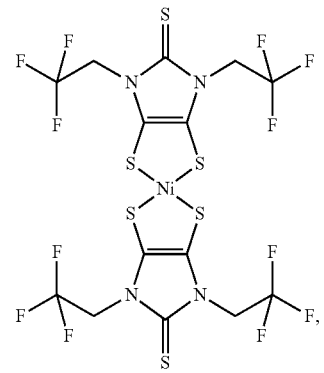
(A-27)
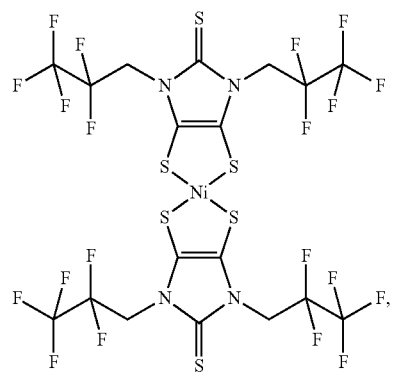
(A-28)
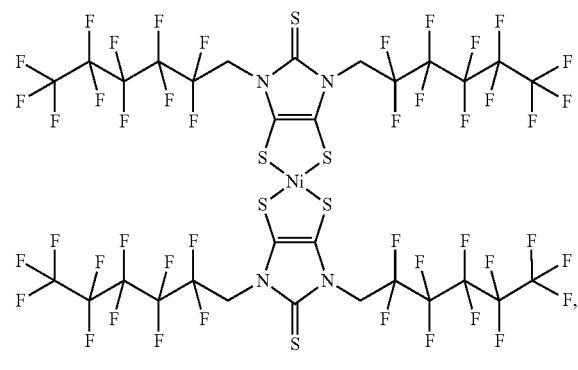
(A-29)
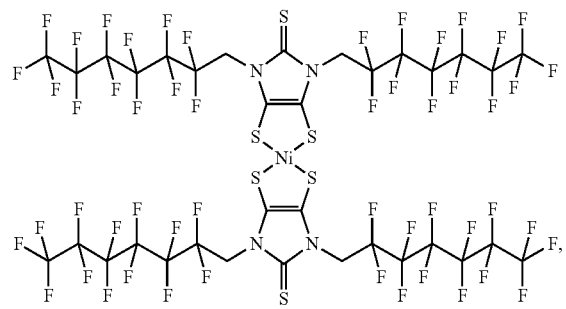
(A-30)
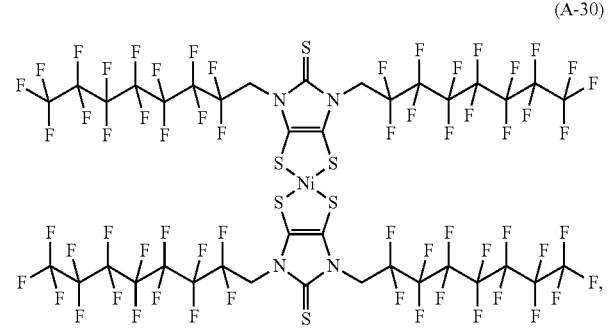
(A-31)
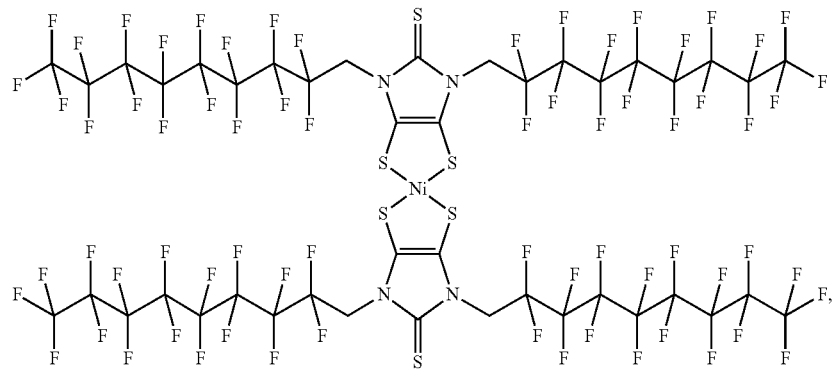

-continued
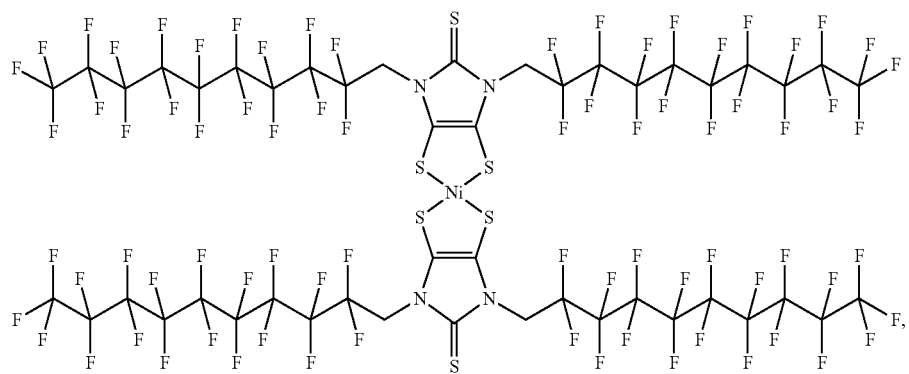
(A-32)
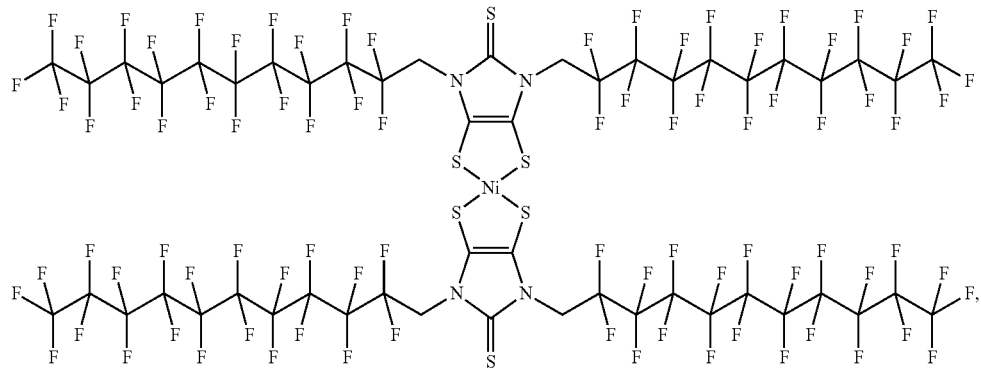
(A-33)
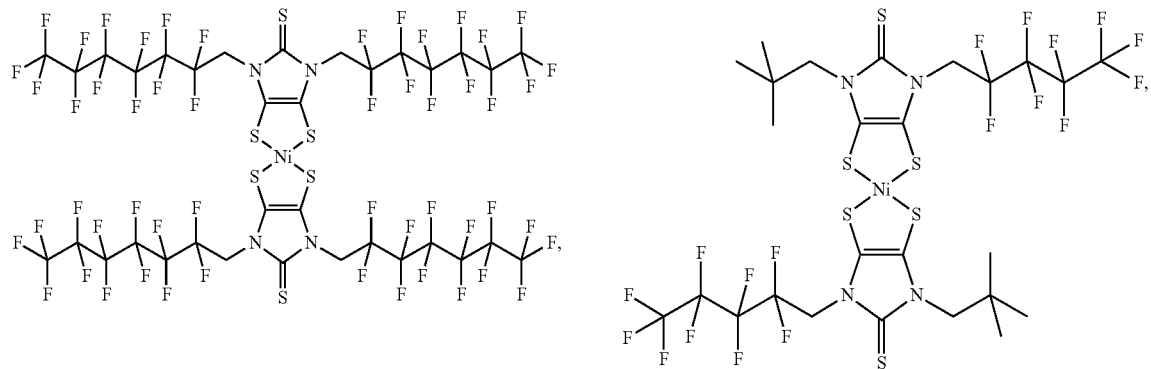
(A-34) (A-35)
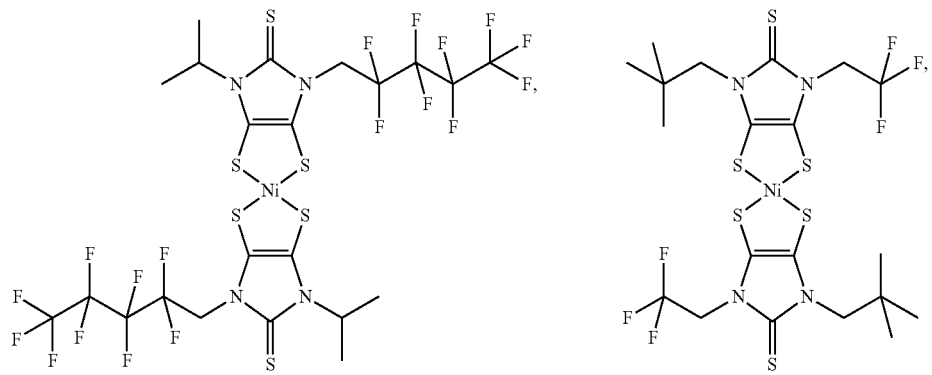
(A-36) (A-37)

-continued
(A-38)
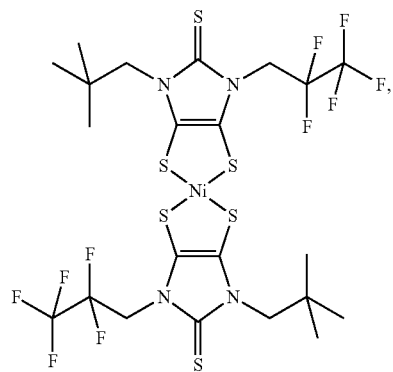
(A-39)
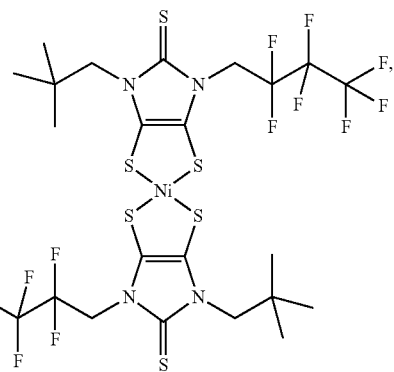
(A-40)
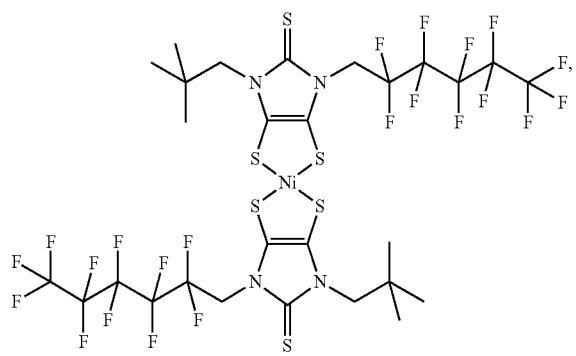
(A-41)
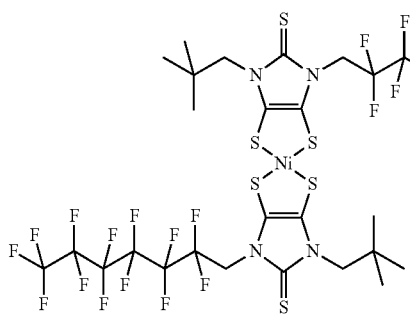
(A-42)
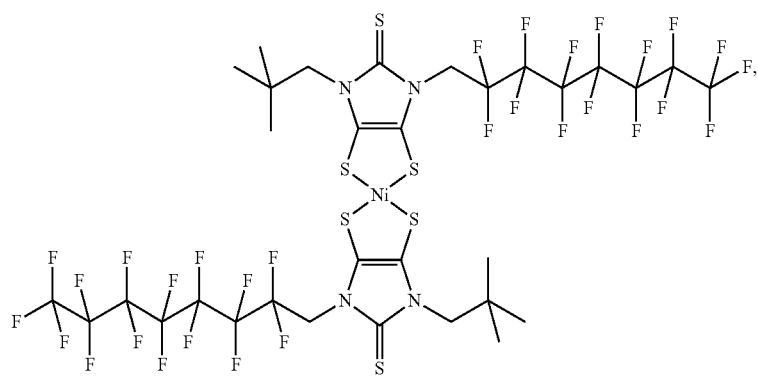
(A-43)
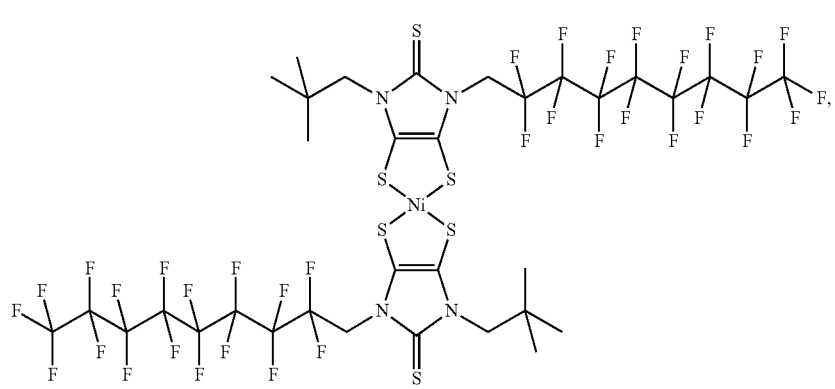

-continued
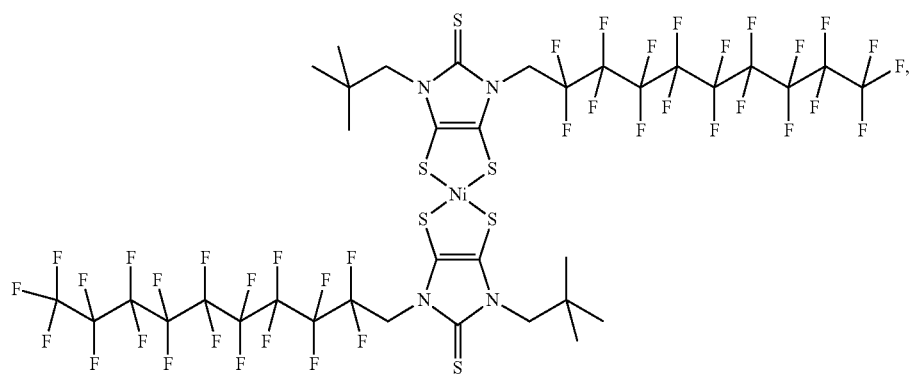
(A-44)
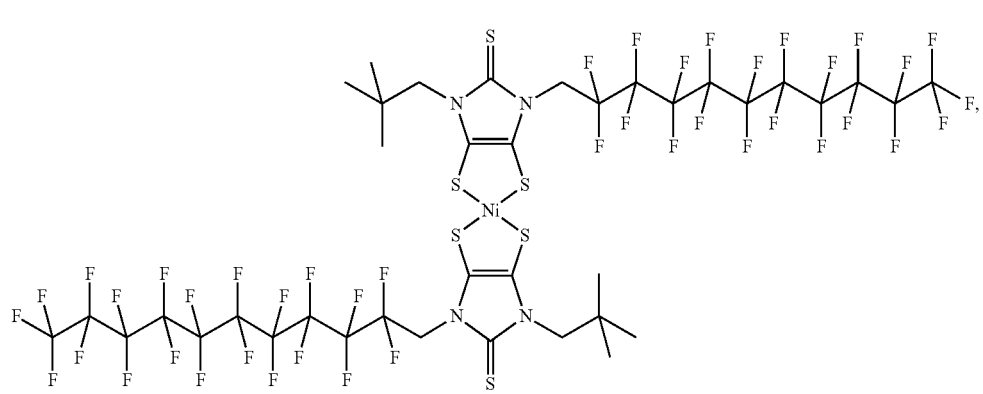
(A-45)
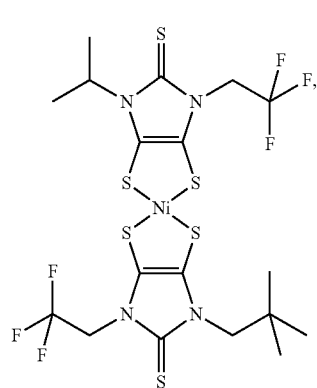
(A-46)
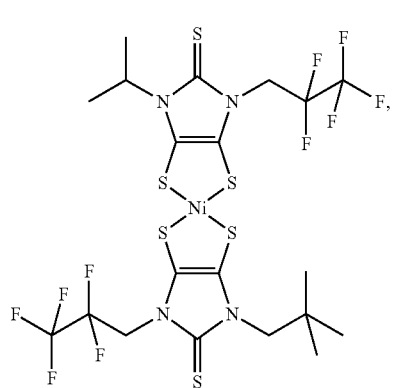
(A-47)
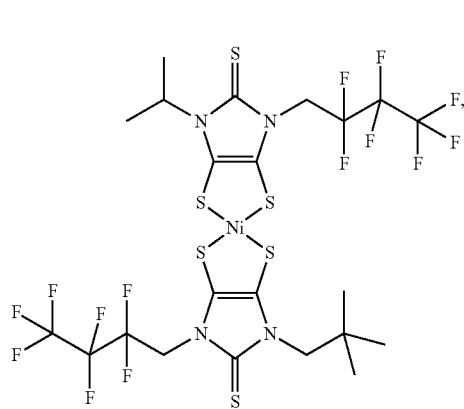
(A-48)
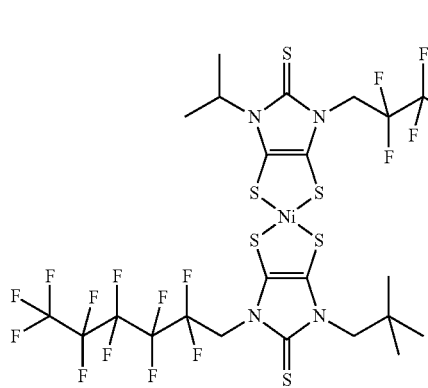
(A-49)

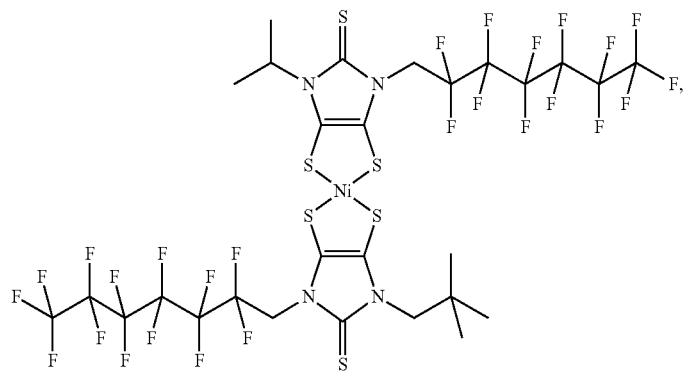
(A-50)
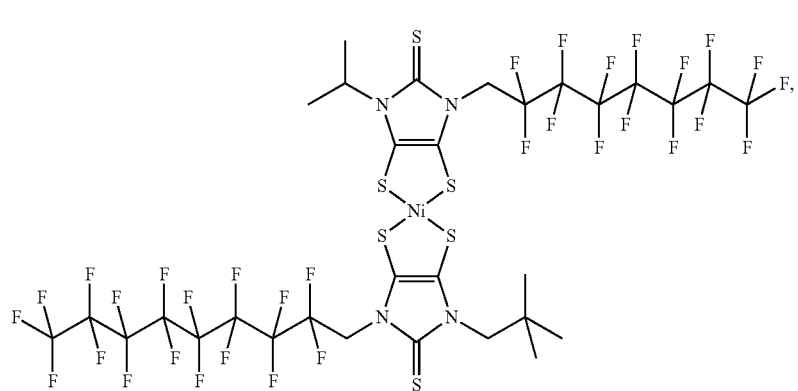
(A-51)
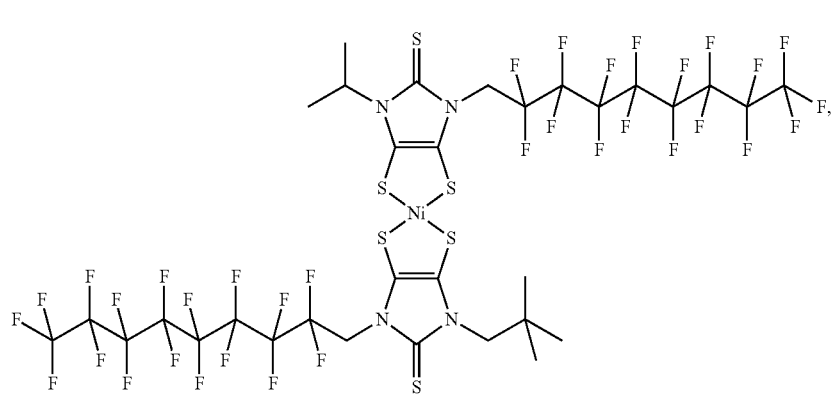
(A-52)
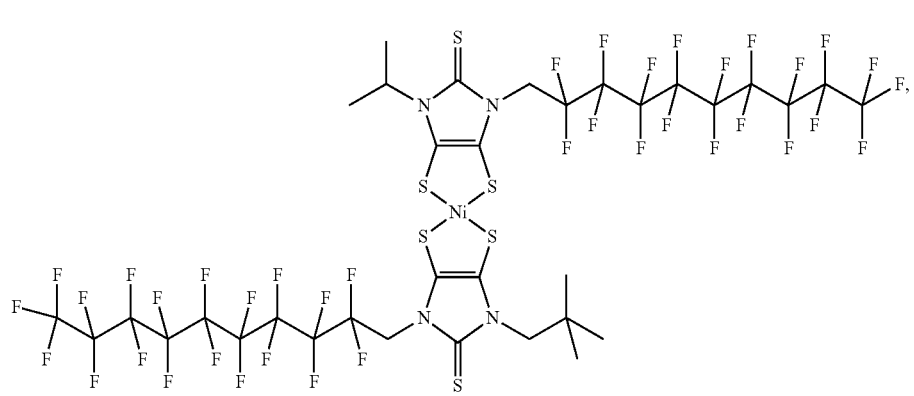
(A-53)

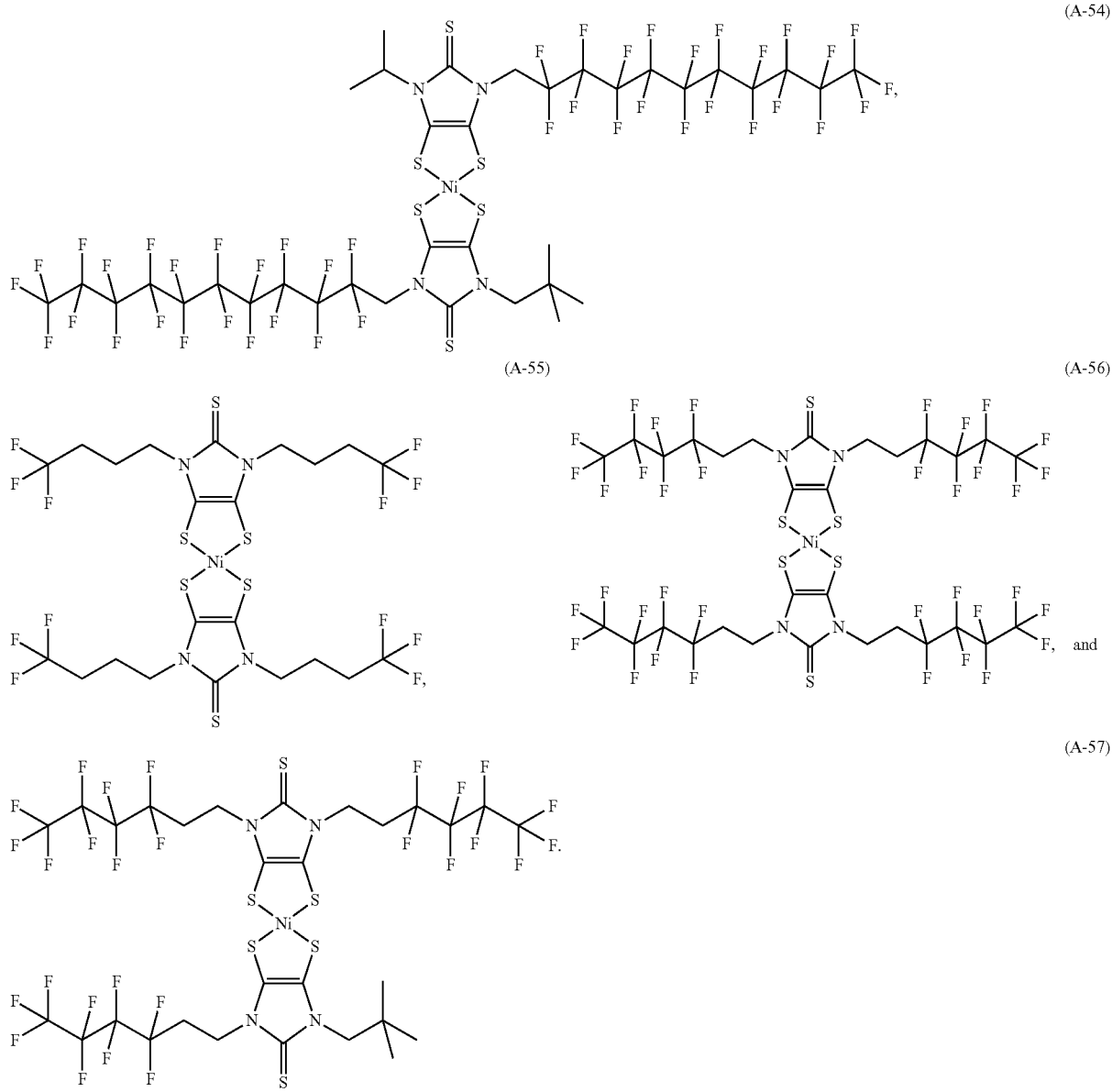

6. A method of printing, comprising contacting the metal dithiolene complex of claim 1 with a substrate, to obtain a printed document.

7. The method of claim 6, wherein the metal dithiolene complex is present in a printing ink formulation that improves a fastness property of a printed security document.

8. A printing ink formulation, comprising
a) the metal dithiolene complex of claim 1,
b) a polymeric binder,
c) a solvent,
d) optionally a colorant, and
e) optionally a further additive.

9. The printing ink formulation of claim 8, comprising
a) 0.0001 to 25% by weight of the metal dithiolene complex of claims 1,
b) 5 to 74% by weight of the polymeric binder,
c) 1 to 94.9999% by weight of the solvent,
d) 0 to 25% by weight of the colorant, and
e) 0 to 25 % by weight of the further additive,
wherein the sum of components a) to e) adds up to 100%.

10. A security document, comprising a substrate and the metal dithiolene complex of claim 1.

11. A security document, comprising the printing ink formulation of claim 8.

12. The security document of claim 10, which is selected from the group consisting of a bank note, a passport, a cheek, a voucher, an ID card, a transaction card, a stamp and a tax label.

13. A colorless IR absorber comprising the metal dithiolene complex of claim 1.

14. A cosmetic preparation, comprising the metal dithiolene complex of claim 1.

15. A process for preparing the metal dithiolene complex of claim 2 having the formula (Ib)

(Ib)
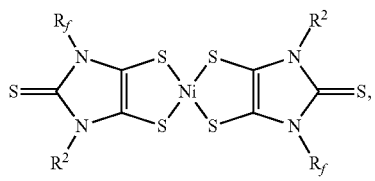
the process comprising reacting a compound of formula (II)
(II)
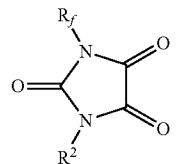
with metallic nickel and a Lawesson's reagent
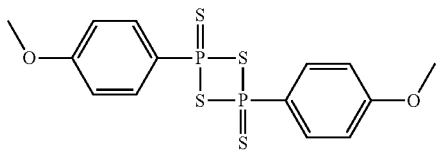
in a solvent.
16. The metal dithiolene complex of claim 1, wherein M is Pd.
17. The metal dithiolene complex of claim 1, wherein M is Pt.
* * * * *